(12) United States Patent
Kahne et al.

(10) Patent No.: US 9,902,985 B2
(45) Date of Patent: Feb. 27, 2018

(54) CHEMOENZYMATIC METHODS FOR SYNTHESIZING MOENOMYCIN ANALOGS

(71) Applicant: President and Fellows of Harvard College, Cambridge, MA (US)

(72) Inventors: Daniel Evan Kahne, Brookline, MA (US); Suzanne Walker Kahne, Brookline, MA (US); Emma Doud, Chicago, IL (US); Christian M. Gampe, Brighton, MA (US); Hirokazu Tsukamoto, Sendai (JP)

(73) Assignee: President and Fellows of Harvard College, Cambridge, MA (US)

( * ) Notice: Subject to any disclaimer, the term of this patent is extended or adjusted under 35 U.S.C. 154(b) by 387 days.

(21) Appl. No.: 14/390,871

(22) PCT Filed: Apr. 5, 2013

(86) PCT No.: PCT/US2013/035427
§ 371 (c)(1),
(2) Date: Oct. 6, 2014

(87) PCT Pub. No.: WO2013/152279
PCT Pub. Date: Oct. 10, 2013

(65) Prior Publication Data
US 2015/0119561 A1    Apr. 30, 2015

Related U.S. Application Data

(60) Provisional application No. 61/621,186, filed on Apr. 6, 2012.

(51) Int. Cl.
| | | |
|---|---|---|
| C12P 19/44 | (2006.01) |
| C07H 1/00 | (2006.01) |
| C07H 13/00 | (2006.01) |
| C07H 13/04 | (2006.01) |
| C12P 19/18 | (2006.01) |
| C12N 9/12 | (2006.01) |

(52) U.S. Cl.
CPC .............. *C12P 19/44* (2013.01); *C07H 1/00* (2013.01); *C07H 13/00* (2013.01); *C07H 13/04* (2013.01); *C12N 9/1241* (2013.01); *C12P 19/18* (2013.01); *C12Y 207/07012* (2013.01)

(58) Field of Classification Search
None
See application file for complete search history.

(56) References Cited

U.S. PATENT DOCUMENTS

| | | |
|---|---|---|
| 3,949,070 A | 4/1976 | Arai et al. |
| 3,992,263 A | 11/1976 | Dietrich et al. |
| 4,270,537 A | 6/1981 | Romaine |
| 4,522,811 A | 6/1985 | Eppstein et al. |
| 4,596,556 A | 6/1986 | Morrow et al. |
| 4,684,626 A | 8/1987 | Welzel et al. |
| 4,790,824 A | 12/1988 | Morrow et al. |
| 4,842,857 A | 6/1989 | Meyers et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,206,405 A | 4/1993 | Aretz et al. |
| 5,260,051 A | 11/1993 | Cho |
| 5,260,206 A | 11/1993 | Aretz et al. |

(Continued)

FOREIGN PATENT DOCUMENTS

| | | |
|---|---|---|
| EP | 0 652 205 A2 | 5/1995 |
| EP | 1 069 130 A1 | 1/2001 |

(Continued)

OTHER PUBLICATIONS

Hanβke, G., et al. (2002) Deficiency of UDP-galactose:N-acetylglucosamine β-1,4-galactosyltransferase I causes the congenital disorder of glycosylation type IId. Journal of Clinical Investigation, vol. 109, No. 6, p. 725-733.*

(Continued)

*Primary Examiner* — Shaojia A Jiang
*Assistant Examiner* — Bahar Craigo
(74) *Attorney, Agent, or Firm* — Wolf, Greenfield & Sacks, P.C.

(57) ABSTRACT

The present invention provides methods of synthesizing moenomycin analogs of Formula (I). The present invention also provides compositions comprising a compound of Formula (I) and kits for synthesizing compounds of Formula (I).

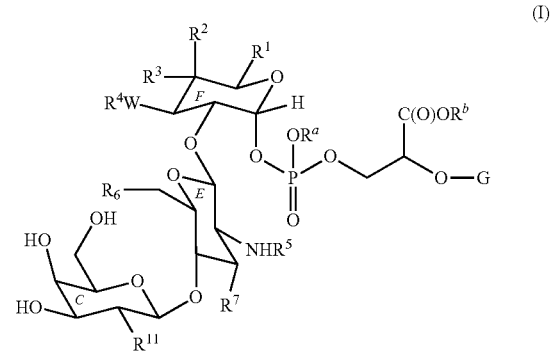

21 Claims, No Drawings

(56) References Cited

U.S. PATENT DOCUMENTS

| | | | |
|---|---|---|---|
| 5,312,335 A | 5/1994 | McKinnon et al. |
| 5,315,038 A | 5/1994 | Aretz et al. |
| 5,316,929 A | 5/1994 | Aretz et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,417,662 A | 5/1995 | Hjertman et al. |
| 5,454,971 A | 10/1995 | Sakai et al. |
| 5,466,220 A | 11/1995 | Brenneman |
| 5,480,381 A | 1/1996 | Weston |
| 5,503,627 A | 4/1996 | McKinnon et al. |
| 5,506,140 A | 4/1996 | Aretz et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,649,912 A | 7/1997 | Peterson |
| 5,704,911 A | 1/1998 | Parsons |
| 5,736,533 A | 4/1998 | Simon et al. |
| 5,888,721 A | 3/1999 | Rothstein et al. |
| 5,893,397 A | 4/1999 | Peterson et al. |
| 5,986,089 A | 11/1999 | Vertesy et al. |
| 5,993,412 A | 11/1999 | Deily et al. |
| 6,077,830 A | 6/2000 | Vertesy et al. |
| 6,114,309 A | 9/2000 | Allanson et al. |
| 6,153,381 A | 11/2000 | Rothstein |
| 6,207,820 B1 | 3/2001 | Allanson et al. |
| 6,242,424 B1 | 6/2001 | Riess et al. |
| 6,274,716 B1 | 8/2001 | Allanson et al. |
| 6,461,829 B1 | 10/2002 | Kahne |
| 6,534,278 B1 | 3/2003 | Rothstein |
| 6,911,318 B2 | 6/2005 | Kahne |
| 6,913,895 B1 | 7/2005 | Goldman et al. |
| 7,129,229 B2 | 10/2006 | Raddatz et al. |
| 7,186,813 B1 | 3/2007 | Schweitzer et al. |
| 8,604,004 B2 | 12/2013 | Kahne et al. |
| 9,115,358 B2 | 8/2015 | Walker et al. |
| 9,273,084 B2 | 3/2016 | Kahne et al. |
| 2003/0108969 A1 | 6/2003 | DeSousa et al. |
| 2003/0129683 A1 | 7/2003 | Kahne |
| 2003/0158093 A1 | 8/2003 | Sun et al. |
| 2004/0018582 A1 | 1/2004 | Eggert et al. |
| 2004/0042981 A1 | 3/2004 | Vertesy et al. |
| 2004/0127403 A1 | 7/2004 | Parenti et al. |
| 2004/0147441 A1 | 7/2004 | Leach et al. |
| 2005/0026214 A1 | 2/2005 | Biton et al. |
| 2005/0106555 A1 | 5/2005 | Desousa |
| 2005/0186653 A1 | 8/2005 | Heimann et al. |
| 2005/0287181 A1 | 12/2005 | Murthy |
| 2005/0287198 A1 | 12/2005 | Murthy |
| 2005/0287200 A1 | 12/2005 | Murthy |
| 2005/0287219 A1 | 12/2005 | Murthy |
| 2005/0287220 A1 | 12/2005 | Murthy |
| 2006/0040891 A1 | 2/2006 | Jiang et al. |
| 2006/0093632 A1 | 5/2006 | Murthy |
| 2006/0094669 A1 | 5/2006 | Murthy |
| 2006/0142217 A1 | 6/2006 | Meutermans et al. |
| 2007/0060506 A1 | 3/2007 | Walsh et al. |
| 2010/0279980 A1 | 11/2010 | Walker et al. |
| 2011/0136759 A1 | 6/2011 | Kahne et al. |
| 2015/0079618 A1 | 3/2015 | Kahne et al. |
| 2015/0119354 A1 | 4/2015 | Kahne et al. |
| 2015/0166594 A1 | 6/2015 | Kahne et al. |
| 2016/0280732 A1 | 9/2016 | Kahne et al. |

FOREIGN PATENT DOCUMENTS

| | | |
|---|---|---|
| WO | WO 97/13537 A1 | 4/1997 |
| WO | WO 97/37705 A1 | 10/1997 |
| WO | WO 99/26956 A1 | 6/1999 |
| WO | WO 99/34850 A1 | 7/1999 |
| WO | WO 00/52035 A1 | 9/2000 |
| WO | WO 00/64915 A1 | 11/2000 |
| WO | WO 03/020962 A2 | 3/2003 |
| WO | WO 2007/023348 A2 | 3/2007 |
| WO | WO 2008/021367 A2 | 2/2008 |
| WO | WO 2009/046314 A2 | 4/2009 |
| WO | WO 2013/151697 A1 | 10/2013 |
| WO | WO 2013/152277 A2 | 10/2013 |
| WO | WO 2013/152279 A1 | 10/2013 |

OTHER PUBLICATIONS

Dube, D. H. et al., Chem. Commun., "Chemical tools to discover and target bacterial glycoproteins", 2011, vol. 47, pp. 87-101.*

Hu, P. et al., FEBS Letters, "Site-specific interplay between O-GlcNAcylation and phosphorylation in cellular regulation", 2010, vol. 584, pp. 2526-2538.*

Schneider et al., Isolation and analysis of moenomycin and its biosynthetic intermediates from Streptomyces ghanaensis (ATCC 14672) wildtype and selected mutants. Z Naturforsch C. Mar.-Apr. 1997;52(3-4):217-26. Abstract Only.

Vogel et al., Moenomycin analogues with long-chain amine lipid parts from reductive aminations. Tetrahedron. 2001;57:4147-60.

Extended European Search Report, dated Jul. 2, 2013, in connection with Application No. EP 08834841.2.

International Search Report and Written Opinion, dated Mar. 10, 2009, in connection with Application No. PCT/US2008/078771.

International Preliminary Report on Patentability dated Apr. 15, 2010, in connection with Application No. PCT/US2008/078771.

Invitation to Pay Additional Fees dated Jun. 10, 2013, in connection with Application No. PCT/US2013/035416.

International Search Report and Written Opinion, dated Oct. 15, 2013, in connection with Application No. PCT/US2013/035416.

International Preliminary Report on Patentability, dated Oct. 16, 2014, in connection with Application No. PCT/US2013/035416.

International Search Report and Written Opinion, dated Jun. 18, 2013, in connection with Application No. PCT/US2013/030800.

International Preliminary Report on Patentability, dated Oct. 16, 2014, in connection with Application No. PCT/US2013/030800.

International Search Report and Written Opinion, dated Sep. 30, 2008, in connection with Application No. PCT/US2007/017999.

International Preliminary Report on Patentability, dated Feb. 26, 2009, in connection with Application No. PCT/US2007/017999.

International Search Report and Written Opinion, dated Jun. 28, 2013, in connection with Application No. PCT/US2013/035427.

International Preliminary Report on Patentability, dated Oct. 16, 2014, in connection with Application No. PCT/US2013/035427.

Genbank Submission; NIH/NCBI, Accession No. AAF24002; Belanger et al.; Jan. 12, 2000.

Genbank Submission; NIH/NCBI, Accession No. AAG34163; Yoo et al.; Mar. 6, 2001.

Genbank Submission; NIH/NCBI, Accession No. AA006921; Rascher et al.; Feb. 21, 2003.

Genbank Submission; NIH/NCBI, Accession No. AAU93096; Ward et al.; Nov. 21, 2011.

Genbank Submission; NIH/NCBI, Accession No. AAX98210; McAlpine et al.; Apr. 25, 2005.

Genbank Submission; NIH/NCBI, Accession No. AY240962; Petricek et al.; Jul. 5, 2006.

Genbank Submission; NIH/NCBI, Accession No. BAC68501; Omura et al.; Dec. 21, 2007.

Genbank Submission; NIH/NCBI, Accession No. BAC68502; Omura et al.; Dec. 21, 2007.

Genbank Submission; NIH/NCBI, Accession No. BAC70368; Omura et al.; Dec. 21, 2007.

Genbank Submission; NIH/NCBI, Accession No. CAA22758; Bentley et al.; Oct. 23, 2008.

Genbank Submission; NIH/NCBBI, Accession No. CAC01594; Bentley et al.; Oct. 23, 2008.

Genbank Submission; NIH/NCBI, Accession No. CAC37544; Bentley et al.; Oct. 23, 2008.

Genbank Submission; NIH/NCBI, Accession No. CAC37545; Bentley et al.; Oct. 23, 2008.

Genbank Submission; NIH/NCBI, Accession No. CAI08539; Rabus et al.; Sep. 11, 2009.

(56) References Cited

OTHER PUBLICATIONS

Genbank Submission; NIH/NCBI, Accession No. EAM38951; Jun. 15, 2005.
Genbank Submission; NIH/NCBI, Accession No. EA007657; Jul. 26, 2005.
Genbank Submission; NIH/NCBI, Accession No. EAS11435; Apr. 9, 2007.
Genbank Submission; NIH/NCBI, Accession No. EAS23724; Mar. 22, 2006.
Genbank Submission; NIH/NCBI, Accession No. EAS99725; Apr. 18, 2006.
Genbank Submission; NIH/NCBI, Accession No. JC7965; Nemoto et al.; Mar. 15, 2004.
Genbank Submission; NIH/NCBI, Accession No. NP_142754; Kawarabayasi et al.; Jan. 19, 2012.
Genbank Submission; NIH/NCBI, Accession No. NP_220145; Griffiths et al.; Sep. 15, 2011.
Genbank Submission; NIH/NCBI, Accession No. NP_630535; Hsiao et al.; Jan. 19, 2012.
Genbank Submission; NIH/NCBI, Accession No. YP_074610; Ueda et al.; Jan. 23, 2012.
Genbank Submission; NIH/NCBI, Accession No. YP_075255; Ueda et al.; Jan. 23, 2012.
Genbank Submission; NIH/NCBI, Accession No. YP_075256; Ueda et al.; Jan. 23, 2012.
Genbank Submission; NIH/NCBI, Accession No. ZP_00616987; Heuts et al.; Jun. 28, 2007.
Adachi et al., Degradation and reconstruction of moenomycin A and derivatives: dissecting the function of the isoprenoid chain. J Am Chem Soc. Nov. 1, 2006;128(43):14012-3.
Arai et al., Pholipomycin, a new member of phosphoglycolipid antibiotics. I. Taxonomy of producing organism and fermentation and isolation of pholipomycin. J Antibiot (Tokyo). Dec. 1977;30(12):1049-54.
Baizman et al., Antibacterial activity of synthetic analogues based on the disaccharide structure of moenomycin, an inhibitor of bacterial transglycosylase. Microbiology. Dec. 2000;146 Pt 12:3129-40.
Banker et al., Modern Pharmacetuics. 3rd ed. Marcel Dekker, New York, 1996, p. 596.
Bardone et al., Teichomycins, new antibiotics from *Actinoplanes teichomyceticus* nov. sp. II. Extraction and chemical characterization. J Antibiot (Tokyo). Mar. 1978;31(3):170-7.
Barrett et al., Kinetic characterization of the glycosyltransferase module of *Staphylococcus aureus* PBP2. J Bacteriol. Mar. 2005;187(6):2215-7.
Belanger et al., Functional analysis of genes responsible for the synthesis of the B-band O antigen of Pseudomonas aeruginosa serotype 06 lipopolysaccharide. Microbiology. Dec. 1999;145 ( Pt 12):3505-21.
Bentley et al., Complete genome sequence of the model actinomycete *Streptomyces coelicolor* A3(2). Nature. May 9, 2002;417(6885):141-7.
Berge et al., Pharmaceutical salts. J Pharm Sci. Jan. 1977;66(1):1-19.
Bibb, Regulation of secondary metabolism in streptomycetes. Curr Opin Microbiol. Apr. 2005;8(2):208-15.
Bierman et al., Plasmid cloning vectors for the conjugal transfer of DNA from *Escherichia coli* to *Streptomyces* spp. Gene. Jul. 1, 1992;116(1):43-9.
Blackman et al., Tetrazine ligation: fast bioconjugation based on inverse-electron-demand Diels-Alder reactivity. J Am Chem Soc. Oct. 15, 2008;130(41):13518-9. Epub Sep. 18, 2008.
Blondelet-Rouault et al., Antibiotic resistance gene cassettes derived from the omega interposon for use in *E. coli* and *Streptomyces*. Gene. May 6, 1997;190(2):315-7.
Castro-Palomino et al., N-Tetrachlorophthaloyl-Protected Trichloroacetimidate of Glucosamine as Glycosyl Donor in Oligosaccharide Synthesis. Tetrahedron Lett. 1995;36:5343-46.

Chaffin et al., CpsK of *Streptococcus agalactiae* exhibits alpha2,3-sialyltransferase activity in Haemophilus ducreyi. Mol Microbiol. Jul. 2002;45(1):109-22.
Chang, Multidrug resistance ABC transporters. FEBS Lett. Nov. 27, 2003;555(1):102-5.
Chater, Streptomyces inside-out: a new perspective on the bacteria that provide us with antibiotics. Philos Trans R Soc Lond B Biol Sci. May 29, 2006;361(1469):761-8.
Chen et al., Vancomycin analogues active against vanA-resistant strains inhibit bacterial transglycosylase without binding substrate. Proc Natl Acad Sci U S A. May 13, 2003;100(10):5658-63. Epub Apr. 24, 2003.
Cheng et al., Domain requirement of moenomycin binding to bifunctional transglycosylases and development of high-throughput discovery of antibiotics. Proc Natl Acad Sci U S A. Jan. 15, 2008;105(2):431-6. Epub Jan. 8, 2008.
Coates et al., Stereoselective Synthesis of Moenocinol and Assignment of Its Carbon-13 Nuclear Magnetic Resonance Spectrum. J Org Chem. 1980;45:2685-97.
Crich et al., Are Glycosyl Triflates Intermediates in the Sulfoxide Glycosylation Method? A Chemical and 1H, 13C, and 19F NMR Spectroscopic Investigation. J Am Chem Soc. 1997;119:11217-23.
Crich et al., Chapter 2. Gylcosylation with Sulfoxides and Sulfinates as Donors or Promoters. Org React. 2004;64:115-251.
Crich et al., Why are the hydroxy groups of partially protected N-acetylglucosamine derivatives such poor glycosyl acceptors, and what can be done about it? A comparative study of the reactivity of N-acetyl-, N-phthalimido-, and 2-azido-2-deoxy-glucosamine derivatives in glycosylation. 2-Picolinyl ethers as reactivity-enhancing replacements for benzyl ethers. J Am Chem Soc. Jul. 18, 2001;123(28):6819-25.
Daghish et al., Tetrafunctional photoaffinity labels based on Nakanishi's m-nitroalkoxy-substituted phenyltrifluoromethyldiazirine. Angew Chem Int Ed Engl. Jul. 2, 2002;41(13):2293-7.
Dairi, Studies on biosynthetic genes and enzymes of isoprenoids produced by actinomycetes. J Antibiot (Tokyo). Apr. 2005;58(4):227-43.
Datsenko et al., One-step inactivation of chromosomal genes in *Escherichia coli* K-12 using PCR products. Proc Natl Acad Sci U S A. Jun. 6, 2000;97(12):6640-5.
Debenham et al., Two New Orthogonal Amine-Protecting Groups That Can Be Cleaved under Mild or Neutral Conditions. J Am Chem Soc. 1995;117:3302-03.
Decker et al., A general approach for cloning and characterizing dNDP-glucose dehydratase genes from actinomycetes. FEMS Microbiol Left. Aug. 1, 1996;141(2-3):195-201.
Dirksen et al., Rapid oxime and hydrazone ligations with aromatic aldehydes for biomolecular labeling. Bioconjug Chem. Dec. 2008;19(12):2543-8.
Du et al., Identification and functional analysis of dTDP-glucose-4,6-dehydratase gene and its linked gene cluster in an aminoglycoside antibiotics producer of *Streptomyces tenebrarius* H6. Curr Microbiol. Aug. 2004;49(2):99-107.
Durr et al., Biosynthesis of the terpene phenalinolactone in *Streptomyces* sp. Tü6071: analysis of the gene cluster and generation of derivatives. Chem Biol. Apr. 2006;13(4):365-77.
Ebenezer, Colabomycin Co-Metabolites. Synthesis of 2880-II, A Metabolite Related to Ferulic Acid. J Synth Commun. 1991;21:351-58.
Eichhorn et al., Characterization of moenomycin antibiotics from medicated chicken feed by ion-trap mass spectrometry with electrospray ionization. Rapid Commun Mass Spectrom. 2005;19(15):2179-86.
El-Abadla et al., Moenomycin A: The Role of the Methyl Group in the Moenuronamide Unit and a General Discussion of Structure-Activity Relationships. Tetrahedron. 1999;55(3):699-722.
Ellervik et al., A High Yielding Chemical Synthesis of Sialyl Lewis x Tetrasaccharide and Lewis x Trisaccharide; Examples of Regio- and Stereodifferentiated Glycosylations. J Org Chem. 1998;63:9314-22.
Fehlhaber et al., Moenomycin A: A Structural Revision and New Structure-Activity Relations. Tetrahedron. 1990;46(5):1557-68.

(56) References Cited

OTHER PUBLICATIONS

Feng et al., Structure of the Shigella dysenteriae 7 O antigen gene cluster and identification of its antigen specific genes. Microb Pathog. Feb. 2004;36(2):109-15.
Flett et al., High efficiency intergeneric conjugal transfer of plasmid DNA from *Escherichia coli* to methyl DNA-restricting streptomycetes. FEMS Microbiol Lett. Oct. 15, 1997;155(2):223-9.
Fuse et al., Functional and Structural Analysis of a Key Region of the Cell Wall Inhibitor Moenomycin. ACS Chem Biol. 2010;5(7):701-711.
Gampe et al., Tuning the moenomycin pharmacophore to enable discovery of bacterial cell wall synthesis inhibitors. J Am Chem Soc. Mar. 13, 2013;135(10):3776-9. doi: 10.1021/ja4000933. Epub Mar. 4, 2013.
Garegg et al., Formation of Internucleotidic Bonds via Phosphonate Intermediates. Chem Scr. 1985;25:280-82.
Garneau et al., Synthesis of mono- and disaccharide analogs of moenomycin and lipid II for inhibition of transglycosylase activity of penicillin-binding protein 1b. Bioorg Med Chem. Dec. 15, 2004;12(24):6473-94.
Gildersleeve et al., Scavenging Byproducts in the Sulfoxide Glycosylation Reaction: Application to the Synthesis of Ciclamycin 0. J Am Chem Soc. 1999;121:6176-82.
Gildersleeve et al., Sulfenate Intermediates in the Sulfoxide Glycosylation Reaction. J Am Chem Soc. 1998;120:5961-69.
Goldman et al., Differential antibacterial activity of moenomycin analogues on gram-positive bacteria. Bioorg Med Chem Lett. Oct. 16, 2000;10(20):2251-4.
Goldman et al., Inhibition of transglycosylation involved in bacterial peptidoglycan synthesis. Curr Med Chem. Aug. 2000;7(8):801-20.
Gromyko et al., Generation of *Streptomyces globisporus* SMY622 strain with increased landomycin E production and it's initial characterization. J Antibiot (Tokyo). Jun. 2004;57(6):383-9.
Gust et al., PCR-targeted *Streptomyces* gene replacement identifies a protein domain needed for biosynthesis of the sesquiterpene soil odor geosmin. Proc Natl Acad Sci U S A. Feb. 18, 2003;100(4):1541-6. Epub Jan. 31, 2003.
Halliday et al., Targeting the forgotten transglycosylases. Biochem Pharmacol. Mar. 30, 2006;71(7):957-67. Epub Nov. 18, 2005.
Hang et al., Probing Glycosyltransferase Activities with the Staudinger Ligation. J Am Chem Soc. 2004;126(1):6-7.
Hang et al., Small molecule inhibitors of mucin-type O-linked glycosylation from a uridine-based library. Chem Biol. Mar. 2004;11(3):337-45.
Hang et al., The chemistry and biology of mucin-type O-linked glycosylation. Bioorg Med Chem. Sep. 1, 2005;13(17):5021-34.
He et al., Isolation and structural elucidation of AC326-alpha, a new member of the moenomycin group. J Antibiot (Tokyo). Feb. 2000;53(2):191-5.
Hebler-Klintz et al., The First Moenomycin Antibiotic Without the Methyl-Branched Uronic Acid Constituent.—Unexpected Structure Activity Relations. Tetrahedron. 1993;35:7667-78.
Hernández-Torres et al., Temperature-controlled regioselectivity in the reductive cleavage of p-methoxybenzylidene acetals. J Org Chem. Oct. 15, 2004;69(21):7206-11.
Hodgson, Primary metabolism and its control in streptomycetes: a most unusual group of bacteria. Adv Microb Physiol. 2000;42:47-238.
Hong et al., A signal transduction system in *Streptomyces coelicolor* that activates the expression of a putative cell wall glycan operon in response to vancomycin and other cell wall-specific antibiotics. Mol Microbiol. Jun. 2002;44(5):1199-1211.
Hong et al., Inactivation of the carbamoyltransferase gene refines post-polyketide synthase modification steps in the biosynthesis of the antitumor agent geldanamycin. J Am Chem Soc. Sep. 15, 2004;126(36):11142-3.
Hopwood, Soil to genomics: the Streptomyces chromosome. Annu Rev Genet. 2006;40:1-23.

Ishikawa et al., FramePlot: a new implementation of the frame analysis for predicting protein-coding regions in bacterial DNA with a high G + C content. FEMS Microbiol Lett. May 15, 1999;174(2):251-3.
Iyobe et al., Sex pili mutants isolated by macarbomycin treatment. Antimicrob Agents Chemother. May 1973;3(5):614-20.
Jabbouri et al., Involvement of nodS in N-methylation and nodU in 6-O-carbamoylation of *Rhizobium* sp. NGR234 nod factors. J Biol Chem. Sep. 29, 1995;270(39):22968-73.
Jansson et al., 2-(Trimethylsilyl)ethyl Glycosides. Synthesis, Anomeric Deblocking, and Transformation into 1,2-Trans 1-O-Acyl Sugars. J Org Chem. 1988;53:5629-47.
Kahne et al., Glycosylation of Unreactive Substrates. J Am Chem Soc. 1989;111:6881-82.
Kaplan et al., Genes involved in the synthesis and degradation of matrix polysaccharide in Actinobacillus actinomycetemcomitans and Actinobacillus pleuropneumoniae biofilms. J Bacteriol. Dec. 2004;186(24):8213-20.
Kartha et al., Iodine: A Versatile Reagent in Carboyhydrate Chemistry III. Efficient Activation of Glycosyl Halides in Combination with DDQ1. Tetrahedron Lett. 1996;37:8807-10.
Kaur, Expression and characterization of DrrA and DrrB proteins of *Streptomyces peucetius* in *Escherichia coli*: DrrA is an ATP binding protein. J Bacteriol. Feb. 1997;179(3):569-75.
Kawasaki et al., Biosynthesis of a natural polyketide-isoprenoid hybrid compound, furaquinocin A: identification and heterologous expression of the gene cluster. J Bacteriol. Feb. 2006;188(4):1236-44.
Kawasaki et al., Interconversion of the product specificity of type I eubacterial farnesyl diphosphate synthase and geranylgeranyl diphosphate synthase through one amino acid substitution. J Biochem. Jan. 2003;133(1):83-91.
Khidekel et al., A chemoenzymatic approach toward the rapid and sensitive detection of O-GlcNAc posttranslational modifications. J Am Chem Soc. Dec. 31, 2003;125(52):16162-3.
Knirel et al., Somatic antigens of Shigella: structure of the O-specific polysaccharide chain of the Shigella dysenteriae type 7 lipopolysaccharide. Carbohydr Res. Aug. 15, 1988;179:51-60.
Kudo et al., A new family of glucose-1-phosphate/glucosamine-1-phosphate nucleotidylyltransferase in the biosynthetic pathways for antibiotics. J Am Chem Soc. Feb. 16, 2005;127(6):1711-8.
Kuiper et al., A Selective and Mild Synthetic Route to Dialkyl Phosphates. Synthesis. 2003;5:695-98.
Lay et al., Synthesis of N-acetylglucosamine containing Lewis A and Lewis X building blocks based on N-tetrachlorophthaloyl protection synthesis of Lewis X pentasaccharide. Carbohydr Res. Aug. 1998;310(3):157-71.
Lehtovaara et al., A new method for random mutagenesis of complete genes: enzymatic generation of mutant libraries in vitro. Protein Eng. Apr. 1988;2(1):63-8.
Leimkuhler et al., Differential inhibition of *Staphylococcus aureus* PBP2 by lycopeptides antibiotics. J Am Chem Soc. Mar. 16, 2005;127(10):3250-1.
Leskiw et al., Accumulation of bldA-specified tRNA is temporally regulated in *Streptomyces coelicolor* A3(2). J Bacteriol. Apr. 1993;175(7):1995-2005.
Leskiw et al., TTA codons in some genes prevent their expression in a class of developmental, antibiotic-negative, Streptomyces mutants. Proc Natl Acad Sci U S A. Mar. 15, 1991;88(6):2461-5.
Lin et al., Sequence analysis and molecular characterization of genes required for the biosynthesis of type 1 capsular polysaccharide in *Staphylococcus aureus*. J Bacteriol. Nov. 1994;176(22):7005-16.
Linnett et al., Additional antibiotic inhibitors of peptidoglycan synthesis. Antimicrob Agents Chemother. Sep. 1973;4(3):231-6.
Liu et al., Acceptor specificity and inhibition of the bacterial cell-wall glycosyltransferase MurG. Chembiochem. Jul. 7, 2003;4(7):603-9.
Lombo et al., The mithramycin gene cluster of *Streptomyces argillaceus* contains a positive regulatory gene and two repeated DNA sequences that are located at both ends of the cluster. J Bacteriol. Jan. 1999;181(2):642-7.

(56) References Cited

OTHER PUBLICATIONS

Lovering et al., Structural insight into the transglycosylation step of bacterial cell-wall biosynthesis. Science. Mar. 9, 2007;315(5817):1402-5.

Luning et al., Moenomycin-Type Transglycosylase Inhibitors: Inhibiting Activity vs. Topology around the Phosphoric Acid Diester Group. Tetrahedron Left. 1994;35(12):1859-62.

Luzhetskii et al., [Interspecies conjugation of *Escherichia coli-Streptomyces globisporus* 1912 using integrative plasmid pSET152 and its derivatives]. Genetika. Oct. 2001;37(10):1340-7. Russian.

Luzhetskyy et al., Iteratively acting glycosyltransferases involved in the hexasaccharide biosynthesis of landomycin A. Chem Biol. Jul. 2005;12(7):725-9.

Marzian et al., Moenomycin A: Reactions at the Lipid Part. New Structure-Activity Relations. Tetrahedron. 1994;50:5299-308.

McAlpine et al., Microbial genomics as a guide to drug discovery and structural elucidation: ECO-02301, a novel antifungal agent, as an example. J Nat Prod. Apr. 2005;68(4):493-6.

McKeegan et al., The structure and function of drug pumps: an update. Trends Microbiol. Jan. 2003;11(1):21-9.

Men et al., Substrate Synthesis and Activity Assay for MurG. J. Am. Chem. Soc. Feb. 1998;120(10):2484-2485.

Mendez et al., The role of ABC transporters in antibiotic-producing organisms: drug secretion and resistance mechanisms. Res Microbiol. Apr.-May 2001;152(3-4):341-50.

Metten et al., The First Enzymatic Degradation Products of the Antibiotic Moenomycin A. Tetrahedron. 1992;48:8401-18.

Meyers et al., The Diumycins. New Members of an Antibiotic Family Having Prolonged In Vivo Activity. J Antibiot. 1969;22:490-93.

Müller et al., Utility of Glycosyl Phosphites as Glycosyl Donors-Fructofuranosyl and 2-Deoxyhexopyranosyl Phosphites in Glycoside Bond Formation. Tetrahedron Lett. 1994;35:4763-66.

Murrell et al., Biochemical characterization of the SgcAl alpha-D-glucopyranosyl-l-phosphate thymidylyltransferase from the enediyne antitumor antibiotic C-1027 biosynthetic pathway and overexpression of sgcAl in *Streptomyces globisporus* to improve C-1027 production. J Nat Prod. Feb. 2004;67(2):206-13.

Muth et al., A vector sytem with temperature-sensitive replication for gene disruption and mutational cloning in streptomycetes. Mol Gen Genet. 1989;219:341-48.

Nakagawa et al., Biosynthesis of asukamycin. Formation of the 2-amino-3-hydroxycyclopent-2-enone-moiety. J Chem Soc Chem Commun. 1985:519-21.

Nemoto et al., Purification and characterization of geranylgeranylglyceryl phosphate synthase from a thermoacidophilic archaeon, Thermoplasma acidophilum. J Biochem. May 2003;133(5):651-7.

Neundorf et al., Evidence for the combined participation of a C10 and a C15 precursor in the biosynthesis of moenocinol, the lipid part of the moenomycin antibiotics. Chembiochem. Nov. 7, 2003;4(11):1201-5.

Oh et al., Denaturation of circular or linear DNA facilitates targeted integrative transformation of *Streptomyces coelicolor* A3(2): possible relevance to other organisms. J Bacteriol. Jan. 1997;179(1):122-7.

Ostash et al., A streamlined metabolic pathway for the biosynthesis of moenomycin A. Chem Biol. Mar. 2007;14(3):257-67.

Ostash et al., Bacterial transglycosylase inhibitors. Curr Opin Chem Biol. Oct. 2005;9(5):459-66.

Ostash et al., Complete characterization of the seventeen step moenomycin biosynthetic pathway. Biochemistry. Sep. 22, 2009;48(37):8830-41.

Pacholec et al., Characterization of the aminocoumarin ligase SimL from the simocyclinone pathway and tandem incubation with NovM,P,N from the novobiocin pathway. Biochemistry. Mar. 29, 2005;44(12):4949-56.

Paton et al., Molecular characterization of the locus encoding biosynthesis of the lipopolysaccharide O antigen of *Escherichia coli* serotype 0113. Infect Immun. Nov. 1999;67(11):5930-7.

Paulsen, Advances in Selective Chemical Syntheses of Complex Oligosaccharides. Angew Chem Int Ed Engl. 1982;21:155-73.

Petricek et al., Occurrence of two 5-aminolevulinate biosynthetic pathways in *Streptomyces nodosus* subsp. Asukaensis is linked with the production of asukamycin. J Bacteriol. Jul. 2006;188(14):5113-23.

Pfaller, Flavophospholipol use in animals: positive implications for antimicrobial resistance based on its microbiologic properties. Diagn Microbiol Infect Dis. Oct. 2006;56(2):115-21. Epub May 15, 2006.

Ramakrishnan et al., alpha-Lactalbumin (LA) stimulates milk beta-1,4-galactosyltransferase I (beta 4Gal-T1) to transfer glucose from UDP-glucose to N-acetylglucosamine. Crystal structure of beta 4Gal-T1 x LA complex with UDP-Glc. J Biol Chem. Oct. 5, 2001;276(40):37665-71. Epub Aug. 2, 2001.

Ramakrishnan et al., Structure-based design of beta 1,4-galactosyltransferase I (beta 4Gal-T1) with equally efficient N-acetylgalactosaminyltransferase activity: point mutation broadens beta 4Gal-T1 donor specificity. J Biol Chem. Jun. 7, 2002;277(23):20833-9. Epub Mar. 26, 2002.

Rascher et al., Cloning and characterization of a gene cluster for geldanamycin production in *Streptomyces hygroscopicus* NRRL 3602. FEMS Microbiol Lett. Jan. 28, 2003;218(2):223-30.

Rebets et al., Expression of the regulatory protein LndI for landomycin E production in *Streptomyces globisporus* 1912 is controlled by the availability of tRNA for the rare UUA codon. FEMS Microbiol Left. Mar. 2006;256(1):30-7.

Redenbach et al., The *Streptomyces lividans* 66 chromosome contains a 1 MB deletogenic region flanked by two amplifiable regions. Mol Gen Genet. Nov. 1993;241(3-4):255-62.

Riedel et al., Synthesis and Transglycosylase-Inhibiting Properties of a Disaccharide Analogue of Moenomycin A Lacking Substitution at C-4 of Unit f. Tetrahedron. 1999;55(7):1921-36.

Riedl et al., Impact of flavophospholipol and vancomycin on conjugational transfer of vancomycin resistance plasmids. Antimicrob Agents Chemother. Nov. 2000;44(11):3189-92.

Ritzeler et al., Search for new moenomycin structure-activity relationships Synthesis of a trisaccharide precursor of a moenomycin analogue. Tetrahedron. 1997;53:1665-74.

Rose et al., Consensus-degenerate hybrid oligonucleotide primers for amplification of distantly related sequences. Nucleic Acids Res. Apr. 1, 1998;26(7):1628-35.

Rühl et al., A trifunctional reagent for photoaffinity labeling. Tetrahedron Lett. 2000;41(23):4555-58.

Schmidt et al., Nitriles as Solvents in Glycosylation Reactions: Highly Selective β-Glycoside Synthesis. Synlett. 1990;11:694-96.

Schurer et al., Fluorescence correlation spectroscopy as a new method for the investigation of aptamer/target interactions. Biol Chem. Mar. 2001;382(3):479-81.

Schuricht et al., Studies on the Biosynthesis of the Antibiotic Moenomycin A. J Prakt Chem. 2000;342(8):761-72.

Schuricht et al., The Biosynthesis of Moenocinol, the Lipid Part of the Moenomycin Antibiotics. Tetrahedron Lett. 2001;42:3835-37.

Sekurova et al., In vivo analysis of the regulatory genes in the nystatin biosynthetic gene cluster of *Streptomyces noursei* ATCC 11455 reveals their differential control over antibiotic biosynthesis. J Bacteriol. Mar. 2004;186(5):1345-54.

Shin et al., Total synthesis and structure of the ramoplanin Al and A3 aglycons: two minor components of the ramoplanin complex. Proc Natl Acad Sci U S A. Aug. 17, 2004;101(33):11977-9. Epub Jun. 2, 2004.

Sletten et al., A bioorthogonal quadricyclane ligation. J Am Chem Soc. Nov. 9, 2011;133(44):17570-3. Epub Oct. 17, 2011.

Slusarchyk et al., The Structure of a Novel Lipid from the Antibiotic Diumycin. J Am Chem Soc. 1970;92:4486-88.

Slusarchyk et al., The structure of the lipid portion of the antibiotic prasinomycin. Tetrahedron Left. Feb. 1969;8:659-62.

Smith et al., The cps genes of *Streptococcus suis* serotypes 1, 2, and 9: development of rapid serotype-specific PCR assays. J Clin Microbiol. Oct. 1999;37(10):3146-52.

(56) References Cited

OTHER PUBLICATIONS

Soderberg et al., Geranylgeranylglyceryl phosphate synthase. Characterization of the recombinant enzyme from Methanobacterium thermoautotrophicum. Biochemistry. Dec. 11, 2001;40(49):14847-54.

Sosio et al., The gene cluster for the biosynthesis of the glycopeptide antibiotic A40926 by nonomuraea species. Chem Biol. Jun. 2003;10(6):541-9.

Srivastava et al., Combined chemical-enzymic synthesis of deoxygenated oligosaccharide analogs: transfer of deoxygenated D-GlcpNAc residues from their UDP-GlcpNAc derivatives using N-acetylglucosaminyltransferase I. Carbohydr Res. Oct. 25, 1990;207(2):259-76.

Stawinski, Chapter 8. Some Aspects of H-Phosphonate Chemistry. In: Handbook of Organophosphorus Chemistry. R. Engel ed. Marcel Dekker, New York. 1992:377-434.

Stumpp et al., Synthesis of Moenocinol. Tetrahedron. 1986;42:5941-48.

Subramaniam-Niehaus et al., Isolation and analysis of moenomycin and its biosynthetic intermediates from *Streptomyces ghanaensis* (ATCC 14672) wildtype and selected mutants. Z Naturforsch C. Mar.-Apr. 1997;52(3-4):217-26.

Tachibana et al., Novel prenyltransferase gene encoding farnesylgeranyl diphosphate synthase from a hyperthermophilic archaeon, Aeropyrum pernix. Molecular evolution with alteration in product specificity. Eur J Biochem. Jan. 2000;267(2):321-8.

Tahlan et al., Three unlinked gene clusters are involved in clavam metabolite biosynthesis in *Streptomyces clavuligerus*. Can J Microbiol. Oct. 2004;50(10):803-10.

Tai et al., Parallel identification of O-GlcNAc-modified proteins from cell lysates. J Am Chem Soc. Sep. 1, 2004;126(34):10500-1.

Takahashi et al., A two-stage one-pot enzymatic synthesis of TDP-L-mycarose from thymidine and glucose-1-phosphate. J Am Chem Soc. Feb. 8, 2006;128(5):1432-3.

Takahashi et al., Macarbomycin, a new antibiotic containing phosphorus. J Antibiot (Tokyo). Jan. 1970;23(1):48-50.

Taylor et al., The total synthesis of moenomycin A. J Am Chem Soc. Nov. 29, 2006;128(47):15084-5.

Thuy et al., Functional characterizations of novWUS involved in novobiocin biosynthesis from *Streptomyces spheroides*. Arch Biochem Biophys. Apr. 1, 2005;436(1):161-7.

Tirado et al., Stereochemistry of the Iodocarbonation of cis- and trans-3-Methyl-4-pentene-1,2-diols: The Unusual Formation of Several Anti Iodo Carbonates. J Org Chem. 1993;58:5666-73.

Trepanier et al., The positive activator of cephamycin C and clavulanic acid production in *Streptomyces clavuligerus* is mistranslated in a bldA mutant. Microbiology. Mar. 2002;148(Pt 3):64356.

Tschesche et al., Uber den Lipoidteil Moenocinol des Antibiotikums Moenomycin. Tetrahedron Letters. 1968;24:2905-09.

Van Heijenoort, Formation of the glycan chains in the synthesis of bacterial peptidoglycan. Glycobiology. Mar. 2001;11(3):25R-36R.

Vocadlo et al., A chemical approach for identifying O-GlcNAc-modified proteins in cells. Proc Natl Acad Sci U S A. Aug. 5, 2003;100(16):9116-21. Epub Jul. 21, 2003.

Vocadlo et al., A strategy for functional proteomic analysis of glycosidase activity from cell lysates. Angew Chem Int Ed Engl. Oct. 11, 2004;43(40):5338-42.

Vogel et al. Moenomycin analogues with modified lipid side chains from indium-mediated Barbier-type reaction. Tetrahedron. 2001;57:4139-46.

Vogel et al., Some selective reactions of moenomycin A. Bioorg Med Chem Lett. Sep. 4, 2000;10(17):1963-5.

Volke et al., Characterisation of antibiotic moenomycin A interaction with phospholipid model membranes. Chem Phys Lipids. Feb. 28, 1997;85(2):115-23.

Volke et al., On Penicillin-Binding Protein 1b Affinity-Labeling Reagents. Helvetica Chimica Acta. 2003;86(12):4214-32.

Wallhausser et al., Moenomycin, a new antibiotic. I. Fermentation and isolation. Antimicrob Agents Chemother (Bethesda). 1965;5:734-6.

Wang et al., The pgaABCD locus of *Escherichia coli* promotes the synthesis of a polysaccharide adhesin required for biofilm formation. J Bacteriol. May 2004;186(9):2724-34.

Wang et al., Primer preactivation of peptidoglycan polymerases. J Am Chem Soc. Jun. 8, 2011;133(22):8528-30. doi: 10.1021/ja2028712. Epub May 17, 2011.

Weber et al., Exploiting the genetic potential of polyketide producing streptomycetes. J Biotechnol. Dec. 19, 2003;106(2-3):221-32.

Weisenborn et al., The prasinomycins: antibiotics containing phosphorus. Nature. Mar. 18, 1967;213(5081):1092-4.

Welzel et al., [Moenomycin A: Spaltung Des Antibiotikums Mit Trifluoressigsaure/2-Propanol Und Bestimmung Der Verknupfung Von D-Glucose Und 2-Acetamido-2-Desoxy-D-Glucose.] Tetrahedron. 1981;37:97-104. German.

Welzel et al., [Zur Struktur Eines 2-Amino-Cyclopentandion-1,3, Galakturonsaure and Chinovos-Amin Enthaltenden Hydrolyseruchstucks Des Antibiotikums Moenomycin A.] Tetrahedron Lett. 1973;3:227-30. German.

Welzel et al., Moenomycin A: Minimum Structural Requirements for Biological Activity. Tetrahedron. 1987;43:585-98.

Welzel, Syntheses around the transglycosylation step in peptidoglycan biosynthesis. Chem Rev. Dec. 2005;105(12):4610-60.

Welzel, Transglycosylase Inhibition. In: Antibiotics and antiviral compounds- chemical synthesis and modification. Krohn et al., eds. Weinheim, Germany. 1993:373-78.

Westerduin et al., Synthesis of the Fragment GlcNAc-α(1-P-6)-GlcNac of the Cell Wall Polymer of *Staphylococcus Lactis* Having Repeating N-Acetyl-D-Glucosamine Phosphate Units. Tetrahedron Lett. 1986;27:6271-74.

Westrich et al., Cloning and characterization of a gene cluster from *Streptomyces cyanogenus* S136 probably involved in landomycin biosynthesis. FEMS Microbiol Lett. Jan. 15, 1999;170(2):381-7.

White et al., New oligomeric catalyst for the hydrolytic kinetic resolution of terminal epoxides under solvent-free conditions. Tetrahedron Asymm. 2003;14:3633-38.

Wilen et al., Strategies in Optical Resolutions. Tetrahedron. 1977;33:2725-36.

Wilen, Tables of Resolving Agents and Optical Resolutions. E.L. Eliel, ed. Universtify of Notre Dame Press, Notre Dame, IN. 1972:268-98.

Wilson et al., Molecular analysis of tlrB, an antibiotic-resistance gene from tylosin-producing *Streptomyces fradiae*, and discovery of a novel resistance mechanism. J Antibiot (Tokyo). Mar. 1999;52(3):288-96.

Wolff, Burger's Medicinal Chemistry. 5th ed., Part 1. John Wiley & Sons, 1995, pp. 975-977.

Xiang et al., The crystal structure of *Escherichia coli* MoeA and its relationship to the multifunctional protein gephyrin. Structure. Apr. 4, 2001;9(4):299-310.

Ye et al., Better substrates for bacterial transglycosylases. J Am Chem Soc. Apr. 4, 2001;123(13):3155-6.

Yu et al., The biosynthetic gene cluster of the maytansinoid antitumor agent ansamitocin from *Actinosynnema pretiosum*. Proc Natl Acad Sci U S A. Jun. 11, 2002;99(12):7968-73.

Yuan et al., Crystal structure of a peptidoglycan glycosyltransferase suggests a model for processive glycan chain synthesis. Proc Natl Acad Sci U S A. Mar. 27, 2007;104(13):5348-53. Epub Mar. 8, 2007.

Zalkin et al., Enzymes utilizing glutamine as an amide donor. Adv Enzymol Relat Areas Mol Biol. 1998;72:87-144.

Zehl et al., Characterization of moenomycin antibiotic complex by multistage MALDI-IT/RTOF-MS and ESI-IT-MS. J Am Soc Mass Spectrom. Aug. 2006;17(8):1081-90. Epub May 30, 2006.

Zhang et al., A Simple Statistical Parameter for Use in Evaluation and Validation of High Throughput Screening Assays. J Biomol Screen. 1999;4(2):67-73.

(56) References Cited

OTHER PUBLICATIONS

Zhang et al., Molecular and chemical characterization of the lipopolysaccharide O-antigen and its role in the virulence of *Yersinia enterocolitica* serotype O:8. Mol Microbiol. Jan. 1997;23(1):63-76.

Zhu et al., Identification of the function of gene lndM2 encoding a bifunctional oxygenase-reductase involved in the biosynthesis of the antitumor antibiotic landomycin E by *Streptomyces globisporus* 1912 supports the originally assigned structure for landomycinone. J Org Chem. Jan. 21, 2005;70(2):631-8.

Ferse et al., Acceptor Site Recognition of Transglycosylase Inhibitors A beta-D-glucopyranosyl-(1->2)-alpha-D-glucopyranuronamide-derived Moenomycin Analogue. Tetrahedron. 1999;55:3749-3766.

Havel et al., Isopentenoid synthesis in isolated embryonic Drosophila cells. Possible regulation of 3-hydroxy-3-methylglutaryl coenzyme a reductase activity by shunted mevalonate carbon. J Biol Chem. Aug. 5, 1986;261(22):10150-6.

Ostash et al., Moenomycin family antibiotics: chemical synthesis, biosynthesis, and biological activity. Nat Prod Rep. Nov. 2010;27(11):1594-617. doi: 10.1039/c001461n. Epub Aug. 23, 2010.

Trofimenko et al., Two tests for detecting nitrile and amides. Anal Chem. 1958;30(8):1432-34.

\* cited by examiner

CHEMOENZYMATIC METHODS FOR SYNTHESIZING MOENOMYCIN ANALOGS

RELATED APPLICATIONS

The present application is a national stage filing under 35 U.S.C. § 371 of international PCT application, PCT/US2013/035427, filed Apr. 5, 2013, which claims priority under 35 U.S.C. § 119(e) to U.S. provisional patent application, U.S. Ser. No. 61/621,186, filed Apr. 6, 2012, each of which is incorporated herein by reference.

GOVERNMENT FUNDING

This invention was made with U.S. Government support under GM066174, GM076710, and AI083214 awarded by National Institutes of Health. The U.S. Government has certain rights in the invention.

BACKGROUND OF THE INVENTION

Bacteria have the ability to generate resistance to antibiotics through lateral gene transfer, mutation of enzymes, or the expression of enzymes which actively pump the antibiotic out of the cell or break it down. Over the past 10 years, resistance to existing antibiotics has become a significant problem in many countries. Vancomycin is currently the drug of last resort to combat multidrug-resistant Gram-positive bacteria. In many places vancomycin-resistant *Staphylococcus aureus* and *Enterococci* (VRE) have been discovered. There is thus a desperate need for a new antibiotic drug to replace this drug of last resort.

There are a host of cytoplasmic targets for the development of new antibacterials, such as gyrase inhibitors, protein synthesis inhibitors, muramyl cascade inhibitors, and many more. The major hurdle in designing such drugs is that in addition to enzyme based activity these drugs need to cross the bacterial cell wall to exert their antibacterial effect. On the other hand, enzymes involved in synthesis of the bacterial cell wall exist on the cell wall exterior, and therefore drugs inhibiting these enzymes can exert their bactericidal or bacteriostatic effect without having to cross the cell wall. For example, penicillins, cephalosporins, vancomycin, and moenomycin are antibiotics that interact with bacterial transpeptidase enzymes.

Moenomycin is the only known natural product that directly inhibits the synthesis of bacterial peptidoglycan (PG). The biological activity of moenomycin is remarkable compared with that of most other natural antibiotics: it is 10-1000 times more potent than vancomycin against Gram-positive organisms. See, e.g., Ostash and Walker, *Curr. Opin. Chem. Biol.* (2005) 9:459-466; Goldman et al., *Curr. Med. Chem.* (2000) 7:801-820. Structure-activity relationship studies of Moneomycin analogs conducted on the saccharide portion of the molecule have revealed that moenomycins with at least three carbohydrate units (C, E, and F) are active in vivo against Grampositive bacteria. See, e.g., Garneau et al., *Bioorganic & Medicinal Chemistry* (2004) 12:6473-6494. Furthermore, while the phosporyl group and the carboxylate group of the phosphoglycerate linker are now considered important for bioactivity, the moenocinol chain is also considered to be an important structural component of the molecule and probably contributes to target binding both by direct interactions with the hydrophobic funnel that leads to the membrane and by membrane anchoring. See, e.g., Fuse et al., *Chemical Biology* (2010) 5:701-711. However, at the same time, the moenocinol chain is also credited with poor pharmacokinetic properties and high serum binding of meonomycin, e.g., its absorption upon oral administration is relatively poor. See, e.g., van Heijenoort, *Glycobiology* (2001) 11:25R-36R.

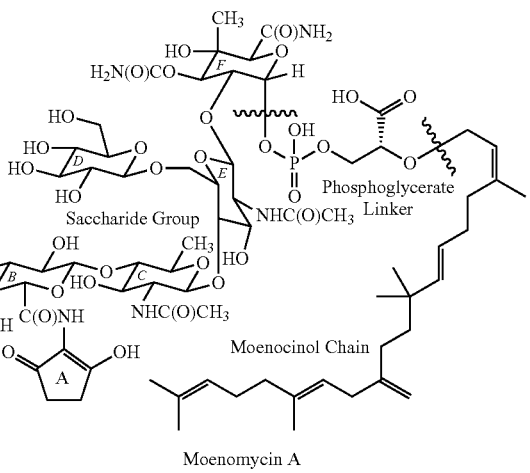

Moenomycin A

SUMMARY OF THE INVENTION

Previous work established that, although $C_{10}$ analogues of the moenocinol chain are too short to retain biological activity, the $C_{25}$ moenocinol chain of Moenomycin A is longer than required for activity. See, e.g., Ostash et al., *Biochemistry* (2009) 48:8830-8841. Moenomycin A and related compounds are potent inhibitors of glycosyltransferase enzymes in bacteria (Ostash et al. *Curr. Opin. Chem. Biol.* 9:459-466 (2005)). The present invention provides methods of synthesizing moenomycin analogs.

In one aspect, the present invention provides methods of synthesizing a compound of Formula (I):

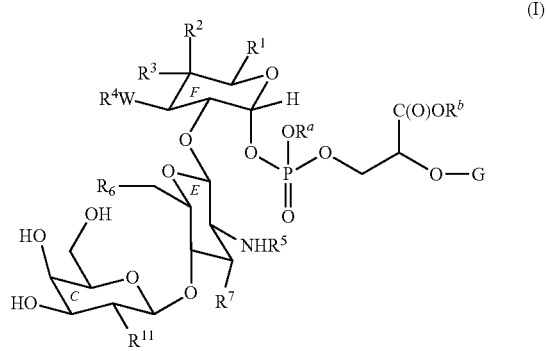

wherein $R^1$, $R^2$, $R^3$, $R^4$, $R^5$, $R^6$, $R^7$, $R^{11}$, $R^a$, $R^b$, W, W and G are as described herein; comprising:

(i) providing a compound of Formula (II):

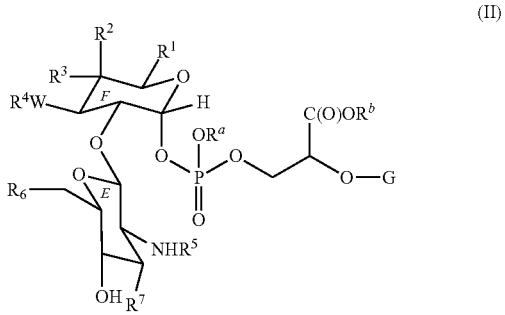

(II)

wherein $R^1$, $R^2$, $R^3$, $R^4$, $R^5$, $R^6$, $R^7$, $R^a$, $R^b$, W, and G are as described herein; and (ii) treating the compound of Formula (II) in the presence of the enzyme GalT with a compound of Formula (III):

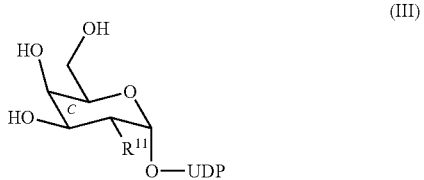

(III)

wherein $R^{11}$ is as described herein;
to yield a compound of Formula (I).

In another aspect, the present invention provides kits and compositions comprising a GalT enzyme.

This and other aspects of the invention will be described in further detail in connection with the detailed description of the invention.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The compounds of the present invention may exist in particular geometric or stereoisomeric forms. The present invention contemplates all such compounds, including cis and trans-isomers, R- and S-enantiomers, diastereomers, (D)-isomers, (L)-isomers, the racemic mixtures thereof, and other mixtures thereof, as falling within the scope of the invention.

Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

When a range of values is listed, it is intended to encompass each value and subrange within the range. For example, an "alkyl group having from 1 to 6 carbons" (also referred to herein as "$C_{1-6}$ alkyl") is intended to encompass 1 ($C_1$ alkyl), 2 ($C_2$ alkyl), 3 ($C_3$ alkyl), 4 ($C_4$ alkyl), 5 ($C_5$ alkyl) and 6 ($C_6$ alkyl) carbons, and a range of 1 to 6 ($C_{1-6}$ alkyl), 1 to 5 ($C_{1-5}$ alkyl), 1 to 4 ($C_{1-4}$ alkyl), 1 to 3 ($C_{1-3}$ alkyl), 1 to 2 ($C_{1-2}$ alkyl), 2 to 6 ($C_{2-6}$ alkyl), 2 to 5 ($C_{2-5}$ alkyl), 2 to 4 ($C_{2-4}$ alkyl), 2 to 3 ($C_{2-3}$ alkyl), 3 to 6 ($C_{3-6}$ alkyl), 3 to 5 ($C_{3-5}$ alkyl), 3 to 4 ($C_{3-4}$ alkyl), 4 to 6 ($C_{4-6}$ alkyl), 4 to 5 ($C_{4-5}$ alkyl), and 5 to 6 ($C_{5-6}$ alkyl) carbons.

The term "aliphatic," as used herein, refers to a monoradical of a non-aromatic, saturated or unsaturated, unbranched ("straight-chain") or branched, substituted or unsubstituted, acyclic hydrocarbon having 1-50 carbon atoms (i.e., $C_{1-50}$ aliphatic). Thus, as used herein, the term "aliphatic" encompasses the groups "alkyl", "alkynyl", and "alkenyl" as defined herein. In certain embodiments, aliphatic refers to a $C_2$-$C_{30}$ aliphatic group. In certain embodiments, aliphatic refers to a $C_5$-$C_{25}$ aliphatic group. In certain embodiments, aliphatic refers to a $C_1$-$C_{10}$ aliphatic group. In certain embodiments, aliphatic refers to a $C_{10}$-$C_{20}$ aliphatic group. In certain embodiments, aliphatic refers to a $C_{11}$-$C_{15}$ aliphatic group. Unless otherwise specified, each instance of aliphatic is independently unsubstituted ("unsubstituted aliphatic") or substituted ("substituted aliphatic") with 1, 2, 3, 4, 5, 6, 7, 8, 9, 10, or more substituents as described herein. Aliphatic group substituents include, but are not limited to, any of the monovalent or divalent substituents described herein, that result in the formation of a stable moiety.

The term "alkyl," as used herein, refers to a monoradical of a non-aromatic, saturated, unbranched ("straight-chain") or branched, substituted or unsubstituted, acyclic hydrocarbon having 1-50 carbon atoms (i.e., $C_{1-50}$ alkyl). In certain embodiments, alkyl refers to a $C_2$-$C_{30}$ alkyl group. In certain embodiments, alkyl refers to a $C_5$-$C_{25}$ alkyl group. In certain embodiments, alkyl refers to a $C_{10}$-$C_{20}$ alkyl group. In certain embodiments, alkyl refers to a $C_1$-$C_{10}$ alkyl group. In certain embodiments, alkyl refers to a $C_{11}$-$C_{15}$ alkyl group. Exemplary alkyl groups include, without limitation, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, tridecyl, tetradecyl, pentadecyl, hexadecyl, heptadecyl, octadecyl, nonadecyl, eicosyl, and the like, which may bear one or more substitutents. Unless otherwise specified, each instance of alkyl is independently unsubstituted ("unsubstituted alkyl") or substituted ("substituted alkyl") with 1, 2, 3, 4, 5, 6, 7, 8, 9, 10, or more substituents as described herein. Alkyl group substituents include, but are not limited to, any of the monovalent or divalent substituents described herein, that result in the formation of a stable moiety.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene," a bivalent aryl ring is "arylene," a bivalent benzene ring is "phenylene," a bivalent heterocycle is "heterocyclylene," a bivalent heteroaryl ring is "heteroarylene," a bivalent alkyl chain is "alkylene," a bivalent cycloalkyl group is "cycloalkylene," a bivalent alkenyl chain is "alkenylene," a bivalent alkynyl chain is "alkynylene," a bivalent heteroalkyl chain is "heteroalkylene," a bivalent heteroalkenyl chain is "heteroalkenylene," a bivalent heteroalkynyl chain is "heteroalkynylene," and so forth. The term "fluoroalkyl," as used herein, refers to an alkyl group having from 1 to 50 carbon atoms wherein at least one hydrogen is replaced with a fluorine atom ("$C_{1-50}$ fluoroalkyl"). In certain embodiments, the fluoroalkyl group has 1 to 8 carbon atoms ("$C_{1-8}$ fluoroalkyl"). In certain embodiments, the fluoroalkyl group has 1 to 6 carbon atoms ("$C_{1-6}$ fluoroalkyl"). In certain embodiments, the fluoroalkyl group has 1 to 4 carbon atoms ("$C_{1-4}$ fluoroalkyl"). In certain embodiments, the fluoroalkyl group has 1 to 3 carbon atoms ("$C_{1-3}$ fluoroalkyl"). In certain embodiments, the fluoroalkyl group has 1 to 2 carbon atoms ("$C_{1-2}$ fluoroalkyl"). In certain embodiments, one hydrogen atom is replaced with a fluorine atom. In certain embodiments, two hydrogen atoms are replaced with fluorine atoms. In certain embodiments, three hydrogen atoms are replaced with fluorine atoms. In certain embodiments, four hydrogen atoms are replaced with fluorine atoms. In certain embodiments, five hydrogen atoms are replaced with fluorine atoms. In certain embodiments, all of the hydrogen atoms are replaced with fluorine atoms (also referred to as a "perfluoroalkyl" group). Exemplary fluoroalkyl groups include, but are not limited to, —$CH_2F$, —$CF_2H$, —$CF_3$, —$CH_2CF_3$, —$CF_2CF_3$, —$CH_2CH_2CF_3$, —$CH_2CF_2CF_3$, —$CF_2CF_2CF_3$, and the like.

The term "alkenyl," as used herein, refers to a monoradical of a non-aromatic, unbranched ("straight-chain") or branched, substituted or unsubstituted, acyclic hydrocarbon having at least one carbon-carbon double bond, having zero carbon-carbon triple bonds, and having 2-50 carbon atoms (i.e., $C_{2-50}$ alkenyl). In certain embodiments, alkenyl refers to a $C_5$-$C_{25}$ alkenyl group. In certain embodiments, alkenyl refers to a $C_{10}$-$C_{20}$ alkenyl group. In certain embodiments, alkenyl refers to a $C_2$-$C_{10}$ alkenyl group. In certain embodiments, alkenyl refers to a $C_{11}$-$C_{15}$ alkenyl group. Exemplary alkenyl groups include, without limitation, ethenyl, propenyl, butenyl, 1-methyl-2-buten-1-yl, and the like, which may bear one or more substituents. Unless otherwise specified, each instance of alkenyl is independently unsubstituted ("unsubstituted alkenyl") or substituted ("substituted alkenyl") with 1, 2, 3, 4, 5, 6, 7, 8, 9, 10, or more substituents as described herein. Alkenyl group substituents include, but are not limited to, any of the monovalent or divalent substituents described herein, that result in the formation of a stable moiety.

The term "alkynyl," as used herein, refers to a monoradical of a non-aromatic, unbranched ("straight-chain") or branched, substituted or unsubstituted, acyclic hydrocarbon having at least one carbon-carbon triple bond, optionally containing one or more carbon-carbon double bonds, and having 2-50 carbon atoms (i.e., $C_{2-50}$ alkynyl). In certain embodiments, alkynyl refers to a $C_5$-$C_{25}$ alkynyl group. In certain embodiments, alkynyl refers to a $C_2$-$C_{10}$ alkynyl group. In certain embodiments, alkynyl refers to a $C_{10}$-$C_{20}$ alkynyl group. In certain embodiments, alkynyl refers to a $C_{11}$-$C_{15}$ alkynyl group. Exemplary alkynyl groups include, without limitation, ethynyl, 2-propynyl (propargyl), 1-propynyl, and the like, which may bear one or more substituents. Unless otherwise specified, each instance of alkynyl is independently unsubstituted ("unsubstituted alkynyl") or substituted ("substituted alkynyl") with 1, 2, 3, 4, 5, 6, 7, 8, 9, 10, or more substituents as described herein. Alkynyl group substituents include, but are not limited to, any of the monovalent or divalent substituents described herein, that result in the formation of a stable moiety.

The term "heteroaliphatic," as used herein, refers to a $C_{1-50}$ aliphatic group wherein one, two or three methylene units of the hydrocarbon chain are independently replaced with one or more oxygen, sulfur or nitrogen atoms. Thus, as used herein, the term "heteroaliphatic" encompasses the groups "heteroalkyl", "heteroalkynyl", and "heteroalkenyl" as defined herein. Unless otherwise specified, each instance of heteroaliphatic is independently unsubstituted ("unsubstituted heteroaliphatic") or substituted ("substituted heteroaliphatic") with 1, 2, 3, 4, 5, 6, 7, 8, 9, 10, or more substituents as described herein. Heteroaliphatic group substituents include, but are not limited to, any of the monovalent or divalent substituents described herein, that result in the formation of a stable moiety.

The term "heteroalkyl," as used herein, refers to a $C_{1-50}$ alkyl group wherein one, two or three methylene units of the hydrocarbon chain are independently replaced with one or more oxygen, sulfur or nitrogen atoms. Unless otherwise specified, each instance of heteroalkyl is independently unsubstituted ("unsubstituted heteroalkyl") or substituted ("substituted heteroalkyl") with 1, 2, 3, 4, 5, 6, 7, 8, 9, 10, or more substituents as described herein. Heteroalkyl group substituents include, but are not limited to, any of the monovalent or divalent substituents described herein, that result in the formation of a stable moiety.

The term "heteroalkenyl," as used herein, refers to a $C_{2-50}$ alkenyl group wherein one, two or three methylene units of the hydrocarbon chain are independently replaced with one or more oxygen, sulfur or nitrogen atoms. Unless otherwise specified, each instance of heteroalkenyl is independently unsubstituted ("unsubstituted heteroalkenyl") or substituted ("substituted heteroalkenyl") with 1, 2, 3, 4, 5, 6, 7, 8, 9, 10, or more substituents as described herein. Heteroalkenyl group substituents include, but are not limited to, any of the monovalent or divalent substituents described herein, that result in the formation of a stable moiety.

The term "heteroalkynyl," as used herein, refers to a $C_{2-50}$ alkynyl group wherein one, two or three methylene units of the hydrocarbon chain are independently replaced with one or more oxygen, sulfur or nitrogen atoms. Unless otherwise specified, each instance of heteroalkynyl is independently unsubstituted ("unsubstituted heteroalkynyl") or substituted ("substituted heteroalkynyl") with 1, 2, 3, 4, 5, 6, 7, 8, 9, 10, or more substituents as described herein. Heteroalkynyl group substituents include, but are not limited to, any of the monovalent or divalent substituents described herein, that result in the formation of a stable moiety.

The terms "carbocyclic" or "carbocyclyl," as used herein, refer to a monoradical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$) and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$) and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups, as defined herein, wherein the point of attachment is on the carbocyclyl ring; in such instances, the number of carbons continues to designate the number of carbons in the carbocyclic ring system. Unless otherwise specified, each instance of a carbocyclyl group is independently unsubstituted ("unsubstituted carbocyclyl") or substituted ("substituted carbocyclyl") with 1, 2, 3, 4, 5, 6, 7, 8, 9, 10, or more substituents as described herein. Carbocyclyl group substituents include, but are not limited to, any of the monovalent or divalent substituents described herein, that result in the formation of a stable moiety.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Exemplary $C_{5-6}$ cycloalkyl groups include, without limitation, cyclopentyl ($C_5$) and cyclohexyl ($C_5$). Exemplary $C_{3-6}$ cycloalkyl groups include, without limitation, the aforementioned $C_{5-6}$ cycloalkyl groups as well as cyclopropyl ($C_3$) and cyclobutyl ($C_4$). Exemplary $C_{3-8}$ cycloalkyl groups include, without limitation, the aforementioned $C_{3-6}$ cycloalkyl groups as well as cycloheptyl ($C_7$) and cyclooctyl ($C_8$). Unless otherwise specified, each instance of a cycloalkyl group is independently unsubstituted ("unsubstituted cycloalkyl") or substituted ("substituted cycloalkyl") with 1, 2, 3, 4, 5, 6, 7, 8, 9, 10, or more substituents as described herein. Cycloalkyl group substituents include, but are not limited to, any of the monovalent or divalent substituents described herein, that result in the formation of a stable moiety.

The terms "heterocyclic" or "heterocyclyl," as used herein, refer to a radical of a 3- to 14-membered non-aromatic ring system having ring carbon atoms and 1 to 4 ring heteroatoms, wherein each heteroatom is independently selected from the group consisting of nitrogen, oxygen and sulfur ("3-14-membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" includes ring systems wherein the heterocyyl ring, as defined above, is fused with one or more carbocycyl groups wherein the point of attachment is either on the carbocycyl or heterocyclyl ring; in such instances, the number of ring members continues to designate the number of ring members in the heterocyclyl ring system. Heterocycyl also includes ring systems wherein the heterocyclyl ring, as defined above, is fused with one or more aryl or heteroaryl groups, wherein the point of attachment is on the heterocyclyl ring; in such instances, the number of ring members continues to designate the number of ring members in the heterocyclyl ring system. In some embodiments, a heterocyclyl group is a 5-10-membered non-aromatic ring system having ring carbon atoms and 1-4 ring heteroatoms, wherein each heteroatom is independently selected from the group consisting of nitrogen, oxygen and sulfur ("5-10-membered heterocyclyl"). In some embodiments, a heterocyclyl group is a 5-8-membered non-aromatic ring system having ring carbon atoms and 1-4 ring heteroatoms, wherein each heteroatom is independently selected from the group consisting of nitrogen, oxygen and sulfur ("5-8-membered heterocyclyl"). In some embodiments, a heterocyclyl group is a 5-6-membered non-aromatic ring system having ring carbon atoms and 1-4 ring heteroatoms, wherein each heteroatom is independently selected from the group consisting of nitrogen, oxygen and sulfur ("5-6-membered heterocyclyl"). In some embodiments, the 5-6-membered heterocyclyl has 1-3 ring heteroatoms selected from the group consisting of nitrogen, oxygen and sulfur. In some embodiments, the 5-6-membered heterocyclyl has 1-2 ring heteroatoms selected from the group consisting of nitrogen, oxygen and sulfur. In some embodiments, the 5-6-membered heterocyclyl has 1 ring heteroatom selected from the group consisting of nitrogen, oxygen and sulfur. Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like. Unless otherwise specified, each instance of heterocyclyl is independently unsubstituted ("unsubstituted heterocyclyl") or substituted ("substituted heterocyclyl") with 1, 2, 3, 4, 5, 6, 7, 8, 9, 10, or more substituents as described herein. Heterocyclyl group substituents include, but are not limited to, any of the monovalent or divalent substituents described herein, that result in the formation of a stable moiety.

The term "aryl," as used herein, refers to a radical of a monocyclic or polycyclic (e.g., bicyclic or tricyclic) aromatic ring system (e.g., having 6, 10 or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring; in such instances, the number of carbon atoms continues to designate the number of carbon atoms in the aryl ring system. Unless otherwise specified, each instance of an aryl group is independently unsubstituted ("unsubstituted aryl") or substituted ("substituted aryl") with 1, 2, 3, 4, 5, 6, 7, 8, 9, 10, or more substituents as described herein. Aryl group substituents include, but are not limited to, any of the monovalent substituents described herein, that result in the formation of a stable moiety.

The term "heteroaryl," as used herein, refers to a radical of a 5-14 membered monocyclic or polycyclic (e.g., bicyclic or tricyclic) aromatic ring system (e.g., having 6, 10 or 14 π electrons shared in a cyclic array) having ring carbon atoms and 1-4 ring heteroatoms provided in the aromatic ring system, wherein each heteroatom is independently selected from the group consisting of nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocycyl or heterocycyl groups wherein the point of attachment is on the heteroaryl ring; in such instances, the number of ring members continues to designate the number of ring members in the heteroaryl ring system. "Heteroaryl" also includes ring systems wherein the heteroaryl ring, as defined above, is fused with one or more aryl groups wherein the point of attachment is either on the aryl or on the heteroaryl ring; in such instances, the number of ring members designates the number of ring members in the fused polycyclic (aryl/heteroaryl) ring system. For example, polycyclic heteroaryl groups wherein one ring does not contain a heteroatom (e.g., indolyl, quinolinyl, carbazolyl and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from the group consisting of nitrogen, oxygen and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from the group consisting of nitrogen, oxygen and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from the group consisting of nitrogen, oxygen and sulfur ("5-6 membered heteroaryl"). In some embodiments, the 5-6 membered heteroaryl has 1-3 ring heteroatoms selected from the group consisting of nitrogen, oxygen and sulfur. In some embodiments, the 5-6 membered heteroaryl has 1-2 ring heteroatoms selected from the group consisting of nitrogen, oxygen and sulfur. In some embodiments, the 5-6 membered heteroaryl has 1 ring heteroatom selected from the group consisting of nitrogen, oxygen and sulfur. Exemplary 5-membered heteroaryls containing 1 heteroatom include, without limitation, pyrrolyl, furanyl and thiophenyl. Exemplary 5-membered heteroaryls containing 2 heteroatoms include, without limitation, imidazolyl, pyrazolyl, oxazolyl, isoxazolyl, thiazolyl, and isothiazolyl. Exemplary 5-membered heteroaryls containing 3 heteroatoms include, without limitation, triazolyl, oxadiazolyl, thiadiazolyl. Exemplary 5-membered heteroaryls containing 4 heteroatoms include, without limitation, tetrazolyl. Exemplary 6-membered heteroaryls containing 1 heteroatom include, without limitation, pyridinyl. Exemplary 6-membered heteroaryls containing 2 heteroatoms include, without limitation, pyridazinyl, pyrimidinyl and pyrazinyl. Exemplary 6-membered heteroaryls containing 3 or 4 heteroatoms include, without limitation, triazinyl and tetrazinyl, respectively. Exemplary 7 membered heteroaryls containing 1 heteroatom include, without limitation, azepinyl, oxepinyl and thiepinyl. Exemplary 5,6-bicyclic heteroaryls include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryls include, without limitation, naphthyridinyl, pteridinyl, quinolinyl, isoquinolinyl, cinnolinyl, quinoxalinyl, phthalazinyl and quinazolinyl. Exemplary tricyclic heteroaryls include, without limitation, phenanthridinyl, dibenzofuranyl, carbazolyl, acridinyl, phenothiazinyl, phenoxazinyl and phenazinyl. Unless otherwise specified, each instance of a heteroaryl group is independently unsubstituted ("unsubstituted heteroaryl") or substituted ("substituted heteroaryl") 1, 2, 3, 4, 5, 6, 7, 8, 9, 10, or more substituents as described herein. Heteroaryl group substituents include, but are not limited to, any of the monovalent substituents described herein, that result in the formation of a stable moiety.

In some embodiments, aliphatic (e.g., alkyl, alkenyl, alkynyl), heteroaliphatic (e.g., heteroalkyl, heteroalkenyl, heteroalkynyl), carbocyclyl, heterocyclyl, aryl and heteroaryl groups, as defined herein, are optionally substituted (e.g., "substituted" or "unsubstituted" aliphatic, "substituted" or "unsubstituted" alkyl, "substituted" or "unsubstituted" alkenyl, "substituted" or "unsubstituted" alkynyl, "substituted" or "unsubstituted" heteroaliphatic, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl, or "substituted" or "unsubstituted" heteroaryl group). In general, the term "substituted" means that at least one hydrogen present on a group (e.g., a carbon or nitrogen atom etc.) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Exemplary monovalent carbon atoms substituents include, but are not limited to, halo/halogen (i.e., —F, —Br, —Cl, —I), —NC, —CN, —NO$_2$, —N$_3$, —CO$_2$H, —CHO, —SO$_2$H, —SO$_3$H, —S(=O)OH, acyl (e.g., —C(=O)R$^A$, —CO$_2$R$^A$, —C(=O)—O—C(=O)R$^A$, —C(=O)SR$^A$, —C(=O)N(R$^B$)$_2$, —C(=O)NR$^B$SO$_2$R$^A$, —C(=NR$^B$)R$^A$, —C(=NR$^B$)OR$^A$, —C(=NR$^B$)N(R$^B$)$_2$, —C(=S)R$^A$, —C(=S)N(R$^A$)$_2$, —C(=S)SR$^A$), amino (e.g., —NH$_2$, —N(OR$^B$)R$^B$, —N(R$^B$)$_2$, —NR$^B$SO$_2$R$^A$, —NR$^B$C(=O)R$^A$, —NR$^B$CO$_2$R$^A$, —NR$^B$C(=O)N(R$^B$)$_2$, —NR$^B$C(=NR$^B$)N(R$^B$)$_2$), thio (e.g., —SH, —SR$^A$, —SSR$^B$), oxy (e.g., —OH, —OR$^A$, —ON(R$^B$)$_2$, —OSO$_2$R$^A$, —OS(=O)R$^A$, —OC(=O)R$^A$, —OCO$_2$R$^A$, —OC(=O)N(R$^B$)$_2$, —OC(=NR$^B$)R$^A$, —OC(=NR$^B$)OR$^A$, —OC(=NR$^B$)N(R$^B$)$_2$), sulfonyl (e.g., —SO$_2$R$^A$, —SO$_2$OR$^A$, —SO$_2$N(R$^B$)$_2$), sulfinyl (e.g., —S(=O)R$^A$), silyl (e.g., —Si(R$^A$)$_3$), C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each aliphatic, heteroaliphatic, carbocyclyl, heterocyclyl, aryl, and heteroaryl is independently substituted with 0, 1, 2, 3, 4, or 5 R$^D$ groups;

each instance of R$^A$ is, independently, selected from the group consisting of C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each aliphatic, heteroaliphatic, carbocyclyl, heterocyclyl, aryl, and heteroaryl is independently substituted with 0, 1, 2, 3, 4, or 5 R$^D$ groups;

each instance of R$^B$ is, independently, selected from the group consisting of hydrogen, —OH, —OR$^A$, —N(R$^C$)$_2$, —CN, —C(=O)R$^A$, —C(=O)N(R$^C$)$_2$, —CO$_2$R$^A$, —SO$_2$R$^A$, —C(=NR$^C$)OR$^A$, —C(=NR$^C$)N(R$^C$)$_2$, —SO$_2$N(R$^C$)$_2$, —SO$_2$R$^C$, —SO$_2$OR$^C$, —SOR$^A$, —C(=S)N(R$^C$)$_2$, —C(=O)SR$^C$, —C(=S)SR$^C$, C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^B$ groups attached to an N atom are joined to form a 3-14 membered heterocyclyl or 5-14 membered heteroaryl ring, wherein each aliphatic, heteroaliphatic, carbocyclyl, heterocyclyl, aryl, and heteroaryl is independently substituted with 0, 1, 2, 3, 4, or 5 R$^D$ groups;

each instance of R$^C$ is, independently, selected from the group consisting of hydrogen, C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^C$ groups attached to an N atom are joined to form a 3-14 membered heterocyclyl or 5-14 membered heteroaryl ring, wherein each aliphatic, heteroaliphatic, carbocyclyl, heterocyclyl, aryl, and heteroaryl is independently substituted with 0, 1, 2, 3, 4, or 5 R$^D$ groups; and each instance of R$^D$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$alkyl), —OC(=NH)OC$_{1-6}$alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —S(=O)C$_{1-6}$ alkyl, C$_{1-6}$ alkyl, C$_{1-6}$ fluoroalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^D$ substituents are joined to form =O, =S or =NR$^B$.

Exemplary divalent carbon atom substituents include, but are not limited to =O, =S, and =NR$^B$, wherein R$^B$ is as defined herein.

Nitrogen atoms can be substituted or unsubstituted as valency permits, and include primary, secondary, tertiary and quarternary nitrogen atoms. Exemplary nitrogen atom substitutents include, but are not limited to, =NR$^B$, —CHO, —C(=O)R$^A$, —CO$_2$R$^A$, —C(=O)SR$^A$, —C(=O)N(R$^B$)$_2$, —C(=O)NR$^B$SO$_2$R$^A$, —C(=NR$^B$)R$^A$, —C(=NR$^B$)OR$^A$, —C(=NR$^B$)N(R$^B$)$_2$, —C(=S)R$^A$, —C(=S)N(R$^A$)$_2$, —C(=S)SR$^A$, —NH$_2$, —N(OR$^B$)R$^B$, —N(R$^B$)$_2$, —NR$^B$SO$_2$R$^A$, —NR$^B$C(=O)R$^A$, —NR$^B$CO$_2$R$^A$, —NR$^B$C(=O)N(R$^B$)$_2$, —NR$^B$C(=NR$^B$)N(R$^B$)$_2$, —OH, —OR$^A$, —SO$_2$R$^A$, —SO$_2$OR$^A$, —SO$_2$N(R$^B$)$_2$, —S(=O)R$^A$, —Si(R$^A$)$_3$, C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^D$ groups.

In certain embodiments, nitrogen atom substituents, as described above, are also referred to as "amino protecting groups" or "nitrogen protecting groups". Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference.

Exemplary amino protecting groups include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Exemplary oxygen substituents include, but are not limited to, —C(=O)R$^A$, CO$_2$R$^A$, —C(=O)—O—C(=O)R$^A$, —C(=O)SR$^A$, —C(=O)N(R$^B$)$_2$, —C(=O)NR$^B$SO$_2$R$^A$, —C(=NR$^B$)R$^A$, —C(=NR$^B$)OR$^A$, —C(=NR$^B$)N(R$^B$)$_2$, —C(=S)R$^A$, —C(=S)N(R$^A$)$_2$, —C(=S)SR$^A$, —SO$_2$R$^A$, —SO$_2$OR$^A$, —SO$_2$N(R$^B$)$_2$, —S(=O)R$^A$, —Si(R$^A$)$_3$, C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^D$ groups.

In certain embodiments, oxygen atom substituents, as described above, are also referred to as "hydroxyl protecting groups" or "oxygen protecting groups". Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference.

Exemplary hydroxyl protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, N,N,N',N'-tetramethylphosphorodiamidate, N-phenylcarbamate, dimethylphosphinothioyl, 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In certain embodiments, a compound of the present invention is provided as a salt. Salts are well known in the art. For example, Berge et al., describe pharmaceutically acceptable salts in detail in *J. Pharmaceutical Sciences*, 1977, 66, 1-19, incorporated herein by reference. Salts of the compounds of this invention include those derived from suitable inorganic and organic acids and bases. Examples include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further salts include, when appropriate, ammonium, quaternary ammonium, and amine cations formed using counterions such as halide, hydroxide, carboxylate, sulfate, phosphate, nitrate, loweralkyl sulfonate and aryl sulfonate. As used herein "inhibition," "inhibiting," and "inhibit", refer to the ability of a compound to reduce, slow, halt or prevent activity of a particular biological process in a cell relative to vehicle. In certain embodiments, the biological process is in vitro (e.g., cellular assay). In certain embodiments, the biological process is in vivo.

The term "independently" is used herein to indicate that the groups can be identical or different.

The term "GalT" as used herein represents a galactosyltransferase protein. In certain embodiments, "GalT" represents bovine GalT as described by Ramakrishnan et al. *J. Biol. Chem.* 2002, 277(23): 20833. In certain embodiments, GalT is wild type bovine GalT. In certain embodiments, GalT is mutant bovine GalT. In certain embodiments, GalT is the truncated mutant Y289L GalT.

DETAILED DESCRIPTION OF CERTAIN EMBODIMENTS

The present invention provides methods of synthesizing moenomycin analogs and compositions and kits useful in the inventive methods. The present invention uses the enzyme GalT from for adding a sugar moiety to the polysaccharide moiety of moenomycin analogs. In certain embodiments, the present invention employs a mutant (Y289L) of the bovine enzyme GaT (Ramakrishnan et al. *J. Biol. Chem.* 2002, 277: 20833). The present invention is particularly useful in the preparation of moenomycin analogs where the polysaccharide moiety is modified as compared to the natural product.

Moenomycin A is a natural product that inhibits peptidoglycan biosynthesis by binding to bacterial transglycosylases. Moenomycin A is a thousand times more potent than the antibiotic vancomycin, but poor pharmacokinetic properties related to the lipid side chain have prevented its use in humans. Removal of the natural lipid side chain completely abolishes biological activities. A comprehensive study of the effect of different side chains, optionally in combination with different sugar portions, on the anti-bacterial activity compared to natural moenomycin A, has been limited as most synthetic transformations employed in the removal of the natural lipid side chain and in the addition of other different side chains have also altered other structural features of the molecule. Recently, biosynthetic and semi-synthetic methodologies were disclosed which enabled SAR study of new moenomycins; e.g., see PCT Application Publication Nos. WO 2008/021367 and WO 2009/046314, incorporated herein by reference. In the '314 publication, the inventors explored groups of intermediate length and hydrophobicity, e.g., $C_{15}$-farnesyl, in an effort to explore the optimal length for activity and bioavailability. The inventors have also found that groups with lengths greater than $C_{15}$-farnesyl, chains substituted with halogen atoms, and chains comprising multiple aryl moieties, provide potent anti-bacterial compounds; see International PCT Application entitled "Moenomycin Analogs, Methods of Synthesis, and Uses Thereof," filed on Apr. 5, 2013, which is incorporated by reference. The inventors have also designed probe compounds based on moenomycin analogs for use in screening compounds that bind to bacterial glycosyltransferases; see International PCT Application PCT/US2013/030800 entitled "Methods and Compounds for Identifying Glycosyltransferase Inhibitors," filed on Mar. 13, 2013, which is incorporated by reference.

Methods of Synthesis

The present invention provides methods of synthesizing moenomycin analogs including a enzymatic step to attach the C ring to the E ring using GalT. In certain embodiments, the GalT is GalT Y289L. Thus in certain embodiments, the present invention provides a method of synthesizing a compound of Formula (I):

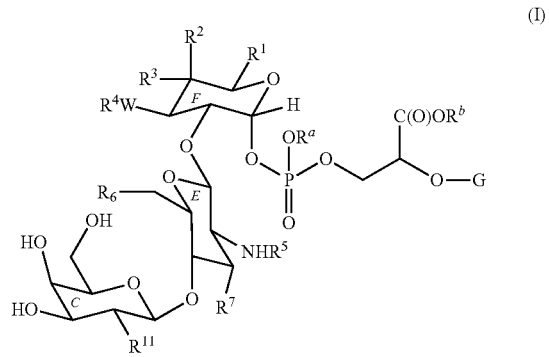

wherein $R^1$ is —C(O)NHR$^8$, —CH$_2$OR$^9$, or —C(O)OR$^9$;

$R^2$ and $R^3$ are independently hydrogen, optionally substituted aliphatic, —OR$^9$, —N(R$^8$)$_2$, or —C(O)NHR$^8$;

W is —O— or —NH—;

$R^4$ is hydrogen, a hydroxyl protecting group, optionally substituted aliphatic, —C(O)R$^{10}$, —C(O)NHR$^8$, —C(=NR$^8$)NHR$^8$, or —C(O)OR$^9$;

$R^5$ is hydrogen, an amino protecting group, optionally substituted aliphatic, or —C(O)R$^{10}$;

$R^6$ is hydrogen, —OR$^9$, or —OR$^{CX}$; wherein $R^{CX}$ is a carbohydrate moiety;

$R^7$ is —OR$^9$ or —N(R$^8$)$_2$;

$R^8$ is hydrogen, an amino protecting group, —C(O)R$^{10}$, optionally substituted aliphatic, optionally substituted aryl, optionally substituted heterocyclyl, or optionally substituted heteroaryl, or two $R^8$ groups on the same nitrogen may be taken together to form an optionally substituted heterocyclyl;

$R^9$ is hydrogen, a hydroxyl protecting group, —C(O)R$^{10}$, optionally substituted aliphatic, optionally substituted aryl, optionally substituted heterocyclyl, or optionally substituted heteroaryl;

$R^{10}$ is optionally substituted aliphatic, optionally substituted heterocyclyl, optionally substituted aryl, or optionally substituted heteroaryl;

$R^{11}$ is optionally substituted aliphatic, —(CH$_2$)$_q$—C(O)R$^{10}$, —N(R$^8$)$_2$, or —OR$^9$;

q is 0, 1, 2, 3, 4, 5, or 6;

$R^a$ and $R^b$ are independently hydrogen or a hydroxyl protecting group;

G is an optionally substituted $C_{1-30}$ aliphatic group, wherein 0 to 10 methylene units are optionally replaced with —O—, —NR$^x$—, —S—, —C(O)—, —C(=NR$^x$), —S(O)—, —SO$_2$—, —N=N—, —C=N—, —N—O—, an optionally substituted arylene, an optionally substituted heterocyclylene, or an optionally substituted heteroarylene; or G is a group of Formula (a), (b), or (c):

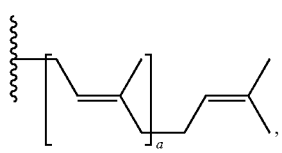

wherein a is 3, 4, or 5;

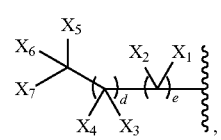

wherein $X_1$, $X_2$, $X_3$, $X_4$, $X_5$, $X_6$, and $X_7$ are each independently hydrogen or halogen;

d is an integer between 1 and 25, inclusive; and e is an integer of between 2 and 25, inclusive;

provided the sum of d and e is greater than 16; or

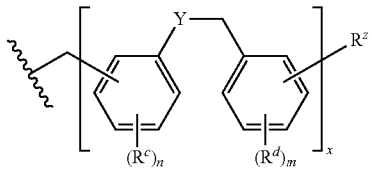

wherein

Y is —O—, —S—, —NR$^Y$—, or an optionally substituted methylene group, wherein R$^Y$ is hydrogen, optionally substituted aliphatic, or an amino protecting group;

each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, or —N(R$^e$)$_2$, wherein each instance of R$^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^e$ groups are joined to form a 5- to 6-membered optionally substituted heterocycyl or optionally substituted heteroaryl ring;

each instance of R$^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^f$, —SR$^f$, —NHR$^f$, or —N(R$^f$)$_2$, wherein each instance of R$^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^f$ groups are joined to form a 5- to 6-membered optionally substituted heterocycyl or optionally substituted heteroaryl ring;

R$^z$ is hydrogen, —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^g$, —SR$^g$, —NHR$^g$, or —N(R$^g$)$_2$, wherein each instance of R$^g$ is independently hydrogen, optionally substituted aliphatic, optionally substituted heteroaliphatic, optionally substituted carbocyclyl, optionally substituted heterocyclyl, optionally substituted aryl, or optionally substituted heteroaryl or two R$^g$ groups are joined to form a 5- to 6-membered optionally substituted heterocycyl or optionally substituted heteroaryl ring;

each instance of n is, independently, 0, 1, 2, 3, or 4;

each instance of m is, independently, 0, 1, 2, 3, or 4; and x is 1, 2, 3, 4, 5, or 6;

comprising:

providing a compound of formula (II):

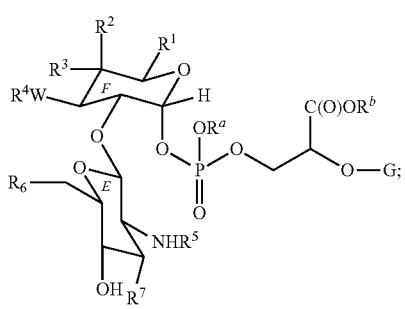

wherein R$^1$, R$^2$, R$^3$, R$^4$, R$^5$, R$^6$, R$^7$, R$^a$, R$^b$, W, and G are as described herein; and reacting the compound of Formula (II) with GalT and a UDP-sugar of formula (III):

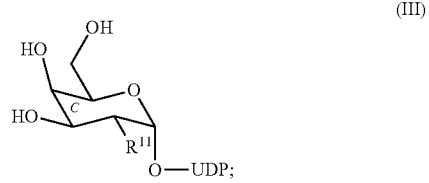

wherein R$^{11}$ is as described herein; to yield a compound of formula (I).

As defined generally above, R$^1$ is —C(O)NHR$^8$, —CH$_2$OR$^9$, or —C(O)OR$^9$; wherein R$^8$ is hydrogen, an amino protecting group, optionally substituted aliphatic, optionally substituted aryl, optionally substituted heterocyclyl, or optionally substituted heteroaryl; and R$^9$ is hydrogen, a hydroxyl protecting group, optionally substituted aliphatic, optionally substituted aryl, optionally substituted heterocyclyl, or optionally substituted heteroaryl. In some embodiments, R$^1$ is —C(O)NHR$^8$. In certain embodiments, R$^1$ is —C(O)NH$_2$. In certain embodiments, R$^1$ is —C(O)NH(alkyl). In some embodiments, R$^1$ is —CH$_2$OR$^9$. In certain embodiments, R$^1$ is —CH$_2$OH. In certain embodiments, R$^1$ is —CH$_2$O(protecting group) or —CH$_2$O(alkyl). In some embodiments, R$^1$ is —C(O)OR$^9$. In certain embodiments, R$^1$ is —CO$_2$H.

As defined generally above, R$^2$ is hydrogen, optionally substituted aliphatic, —OR$^9$, —N(R$^8$)$_2$, or —C(O)NHR$^8$. In some embodiments, R$^2$ is hydrogen. In some embodiments, R$^2$ is optionally substituted aliphatic. In certain embodiments, R$^2$ is C$_{1-6}$ alkyl. In certain embodiments, R$^2$ is methyl. In some embodiments, R$^2$ is —OR$^9$. In certain embodiments, R$^2$ is —OH. In certain embodiments, R$^2$ is —O(alkyl) or —O(protecting group). In some embodiments, R$^2$ is —N(R$^8$)$_2$. In certain embodiments, R$^2$ is —NH$_2$. In certain embodiments, R$^2$ is —NH(alkyl) or —NH (protecting group). In some embodiments, R$^2$ is —C(O) NHR$^8$. In certain embodiments, R$^2$ is —C(O)NH$_2$. In certain embodiments, R$^2$ is —C(O)NH(alkyl).

As defined generally above, R$^3$ is hydrogen, optionally substituted aliphatic, —OR$^9$, —N(R$^8$)$_2$, or —C(O)NHR$^8$. In some embodiments, R$^3$ is hydrogen. In some embodiments, R$^3$ is optionally substituted aliphatic. In certain embodiments, R$^3$ is C$_{1-6}$ alkyl. In certain embodiments, R$^3$ is methyl. In some embodiments, $R^3$ is —$OR^9$. In certain embodiments, $R^3$ is —OH. In certain embodiments, $R^3$ is —O(alkyl) or —O(protecting group). In some embodiments, $R^3$ is —$N(R^8)_2$. In certain embodiments, $R^3$ is —$NH_2$. In certain embodiments, $R^3$ is —NH(alkyl) or —NH(protecting group). In some embodiments, $R^3$ is —C(O)$NHR^8$. In certain embodiments, $R^3$ is —C(O)$NH_2$. In certain embodiments, $R^3$ is —C(O)NH(alkyl).

In some embodiments, $R^2$ is hydrogen and $R^3$ is optionally substituted aliphatic, —$OR^9$, —$N(R^8)_2$, or —C(O)$NHR^8$. In some embodiments, $R^3$ is hydrogen and $R^2$ is optionally substituted aliphatic, —$OR^9$, —$N(R^8)_2$, or —C(O)$NHR^8$. In certain embodiments, $R^2$ is hydrogen and $R^3$ is —OH. In other embodiments, $R^3$ is hydrogen and $R^2$ is —OH.

As defined generally above, W is —O— or —NH—, and $R^4$ is hydrogen, a hydroxyl protecting group, optionally substituted aliphatic, —C(O)$R^{10}$, —C(O)$NHR^8$, —C(=$NR^8$)$NHR^8$, or —C(O)$OR^9$. In certain embodiments, W is —O—. In certain embodiments, W is —NH—. In some embodiments, $R^4$ is hydrogen. In some embodiments, $R^4$ is a hydroxyl protecting group. In some embodiments, $R^4$ is —C(O)R; wherein $R^{10}$ is optionally substituted aliphatic, optionally substituted heterocyclic, optionally substituted aryl, or optionally substituted heteroaryl. In certain embodiments, $R^4$ is —C(O)R; wherein $R^{10}$ is optionally substituted alkyl. In certain embodiments, $R^4$ is —C(O)$C_{1-6}$alkyl. In certain embodiments, $R^4$ is acetyl. In some embodiments, $R^4$ is —C(O)$OR^9$. In some embodiments, $R^4$ is —C(O)$OR^9$; wherein $R^9$ is aryl. In certain embodiments, $R^4$ is —C(O)OPh. In some embodiments, $R^4$ is —C(O)$NHR^8$. In certain embodiments, $R^4$ is —C(O)$NH_2$. In some embodiments, $R^4$ is —C(=$NR^8$)$NHR^8$. In certain embodiments, $R^4$ is —C(=NH)$NH_2$. In certain embodiments, —W—$R^4$ is —OH, —OC(O)$NH_2$, —NHC(O)$NH_2$, or —NHC(=NH)$NH_2$.

In certain embodiments, $R^1$ is —C(O)$NH_2$, $R^2$ is methyl, $R^3$ is —OH, and —W—$R^4$ is —OC(O)$NH_2$. In certain embodiments, $R^1$ is —C(O)$NH_2$, $R^2$ is hydrogen, $R^3$ is —OH, and —W—$R^4$ is —OC(O)$NH_2$. In certain embodiments, $R^1$ is —C(O)$NH_2$, $R^2$ is —OH, $R^3$ is hydrogen, and —W—$R^4$ is —OH.

As defined generally above, $R^5$ is hydrogen, an amino protecting group, optionally substituted aliphatic, or —C(O)$R^1$. In some embodiments, $R^5$ is hydrogen. In some embodiments, $R^5$ is an amino protecting group. In some embodiments, $R^5$ is optionally substituted aliphatic. In certain embodiments, $R^5$ is optionally substituted alkyl. In certain embodiments, $R^5$ is $C_{1-6}$ alkyl. In some embodiments, $R^5$ is —C(O)R. In some embodiments, $R^5$ is —C(O)R; wherein $R^{10}$ is optionally substituted alkyl. In certain embodiments, $R^5$ is —C(O)$C_{1-6}$alkyl. In certain embodiments, $R^5$ is acetyl.

As defined generally above, $R^6$ is hydrogen, —$OR^9$, or —$OR^{CX}$; wherein $R^{CX}$ is a carbohydrate moiety. In some embodiments, $R^6$ is hydrogen. In some embodiments, $R^6$ is —$OR^9$. In certain embodiments, $R^6$ is —OH. In certain embodiments, $R^6$ is —O(protecting group). In certain embodiments, $R^6$ is —OAc. In some embodiments, $R^6$ is —$OR^{CX}$. In certain embodiments, $R^6$ is —$OR^{CX}$; wherein $R^{CX}$ is of formula:

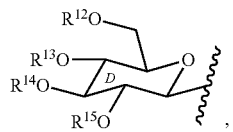

wherein $R^{12}$, $R^{13}$, $R^{14}$, and $R^{15}$ are independently hydrogen, a hydroxyl protecting group, or optionally substituted aliphatic.

As defined generally above, $R^7$ is —$OR^9$ or —$N(R^8)_2$. In some embodiments, $R^7$ is —$OR^9$. In certain embodiments, $R^7$ is —OH. In certain embodiments, $R^7$ is —O(protecting group) or —O(alkyl). In some embodiments, $R^7$ is —$N(R^8)_2$. In certain embodiments, $R^7$ is —$NH_2$. In certain embodiments, $R^7$ is —NH(protecting group), —NH(alkyl), or —N(alkyl)$_2$.

In certain embodiments, $R^6$ is —OH, $R^7$ is —OH, and $R^5$ is acetyl.

As defined generally above, $R^{11}$ is optionally substituted aliphatic, —$(CH_2)_q$—C(O)$R^{10}$, —$N(R^8)_2$, or —$OR^9$; and q is 0, 1, 2, 3, 4, 5, or 6. In certain embodiments, $R^{11}$ is —OH, —$NH_2$, —NHC(O)$C_{1-6}$ alkyl, or —NHC(O)$CH_2N_3$. In certain embodiments, $R^{11}$ is —OH. In certain embodiments, $R^{11}$ is —$NH_2$. In certain embodiments, $R^{11}$ is —NHC(O)$C_{1-6}$ alkyl. In certain embodiments, $R^{11}$ is —NHC(O)$CH_3$. In certain embodiments, $R^{11}$ is —NHC(O)$CH_2N_3$.

In certain embodiments, $R^{11}$ is optionally substituted aliphatic. In certain embodiments, $R^{11}$ is optionally substituted alkyl. In certain embodiments, $R^{11}$ is $C_{1-6}$ alkyl. In certain embodiments, $R^{11}$ is methyl. In certain embodiments, $R^{11}$ is —$(CH_2)_q$C(O)$R^{10}$. In certain embodiments, $R^{11}$ is —$CH_2$C(O)$R^{10}$. In certain embodiments, $R^{11}$ is —C(O)$R^{10}$. In certain embodiments, $R^{11}$ is —$(CH_2)_q$C(O)$R^{10}$, wherein $R^{10}$ is optionally substituted aliphatic. In certain embodiments, $R^{11}$ is —C(O)$CH_3$, —$CH_2$C(O)$CH_3$, —C(O)CH=$CH_2$, or —$CH_2$C(O)CH=$CH_2$. In certain embodiments, $R^{11}$ is —$(CH_2)_q$C(O)$R^{10}$, wherein $R^{10}$ is aliphatic substituted with halo. In certain embodiments, $R^{11}$ is —$(CH_2)_q$C(O)$R^{10}$, wherein $R^{10}$ is aliphatic substituted with chloro, bromo, or iodo. In certain embodiments, $R^{11}$ is —$(CH_2)_q$C(O)$R^{10}$, wherein $R^{10}$ is aliphatic substituted with fluoro. In certain embodiments, $R^{11}$ is —$(CH_2)_q$C(O)$CH_2$Cl, —$(CH_2)_q$C(O)$CH_2$Br, or —$(CH_2)_q$C(O)$CH_2$I. In certain embodiments, $R^{11}$ is —C(O)$CH_2$Cl, —C(O)$CH_2$Br, or —C(O)$CH_2$I. In certain embodiments, $R^{11}$ is —$CH_2$C(O)$CH_2$Cl, —$CH_2$C(O)$CH_2$Br, or —$CH_2$C(O)$CH_2$I. In certain embodiments, $R^{11}$ is —$(CH_2)_q$C(O)$CH_2CF_3$. In certain embodiments, $R^{11}$ is —C(O)$CH_2CF_3$. In certain embodiments, $R^{11}$ is —$CH_2$C(O)$CH_2CF_3$. In certain embodiments, $R^{11}$ is —$(CH_2)_q$C(O)$R^{10}$, wherein $R^{10}$ is aliphatic substituted with —$N_3$, —CN, —NC, —NCO, —OCN, —NCS, —SCN, —NO, or —$N_2$. In certain embodiments, $R^{11}$ is —$(CH_2)_q$C(O)$CH_2N_3$, —$(CH_2)_q$C(O)$CH_2$CN, —$(CH_2)_q$C(O)$CH_2$NC, —$(CH_2)_q$C(O)$CH_2$OCN, —$(CH_2)_q$C(O)$CH_2$NCO, —$(CH_2)_q$C(O)$CH_2$NCS, —$(CH_2)_q$C(O)$CH_2$SCN, —$(CH_2)_q$C(O)$CH_2$NO, or —$(CH_2)_q$C(O)$CHN_2$. In certain embodiments, $R^{11}$ is —C(O)$CH_2N_3$, —C(O)$CH_2$CN, —C(O)$CH_2$NC, —C(O)$CH_2$OCN, —C(O)$CH_2$NCO, —C(O)$CH_2$NCS, —C(O)$CH_2$SCN, —C(O)$CH_2$NO, or —C(O)$CHN_2$. In certain embodiments, $R^{11}$ is —$CH_2$C(O)$CH_2N_3$, —$CH_2$C(O)$CH_2$CN, —$CH_2$C(O)$CH_2$NC, —$CH_2$C(O)$CH_2$OCN, —$CH_2$C(O)$CH_2$NCO, —$CH_2$C(O)$CH_2$NCS, —$CH_2$C(O)$CH_2$SCN, —$CH_2$C(O)$CH_2$NO, or —$CH_2$C(O)$CH_2N_2$. In certain embodiments, $R^{11}$ is —$(CH_2)_q$C(O)$R^{10}$, wherein $R^{10}$ is aliphatic substituted with amino. In certain embodiments, $R^{11}$ is —$(CH_2)_q$C(O)$CH_2NH_2$. In certain embodiments, $R^{11}$ is —C(O)$CH_2NH_2$. In certain embodiments, $R^{11}$ is —$CH_2$C(O)$CH_2NH_2$. In certain embodiments, $R^{11}$ is —$(CH_2)_q$C(O)$R^{10}$, wherein $R^{10}$ is aliphatic substituted with hydroxy. In certain embodiments, $R^{11}$ is —$(CH_2)_q$C(O)$CH_2$OH. In certain embodiments, $R^{11}$ is —C(O)$CH_2$OH. In certain embodiments, $R^{11}$ is —$CH_2$C(O)$CH_2$OH. In certain embodiments, $R^{11}$ is —$(CH_2)_qC(O)R^{10}$, wherein $R^{10}$ is aliphatic substituted with aryl or heteroaryl. In certain embodiments, $R^{11}$ is —$(CH_2)_qC(O)R^{10}$, wherein $R^{10}$ is —$CH_2$aryl or —$CH_2$heteroaryl. In certain embodiments, $R^{11}$ is —$(CH_2)_qC(O)R^{10}$, wherein $R^{10}$ is aliphatic substituted with optionally substituted heterocyclyl. In certain embodiments, $R^{11}$ is —$(CH_2)_qC(O)R^{10}$, wherein $R^{10}$ is aliphatic substituted with

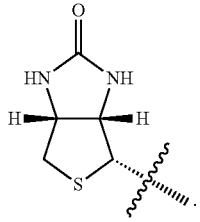

In certain embodiments, $R^{11}$ is —$N(R^8)_2$. In certain embodiments, $R^{11}$ is —$NH_2$. In certain embodiments, $R^{11}$ is —$NHC(O)R^{10}$. In certain embodiments, $R^{11}$ is —$NHC(O)R^{10}$, wherein $R^{10}$ is optionally substituted aliphatic. In certain embodiments, $R^{11}$ is —$NHC(O)CH_3$, or —$NHC(O)CH=CH_2$. In certain embodiments, $R^{11}$ is —$NHC(O)R^{10}$, wherein $R^{10}$ is aliphatic substituted with halo. In certain embodiments, $R^{11}$ is —$NHC(O)R^{10}$, wherein $R^{10}$ is aliphatic substituted with chloro, bromo, or iodo. In certain embodiments, $R^{11}$ is —$NHC(O)R^{10}$, wherein $R^{10}$ is aliphatic substituted with fluoro. In certain embodiments, $R^{11}$ is —$NHC(O)CH_2Cl$, —$NHC(O)CH_2Br$, or —$NHC(O)CH_2I$. In certain embodiments, $R^{11}$ is —$NHC(O)CH_2CF_3$. In certain embodiments, $R^{11}$ is —$NHC(O)R^{10}$, wherein $R^{10}$ is aliphatic substituted with —$N_3$, —$CN$, —$NC$, —$NCO$, —$OCN$, —$NCS$, —$SCN$, —$NO$, or —$N_2$. In certain embodiments, $R^{11}$ is —$NHC(O)CH_2N_3$, —$NHC(O)CH_2CN$, —$NHC(O)CH_2NC$, —$NHC(O)CH_2OCN$, —$NHC(O)CH_2NCO$, —$NHC(O)CH_2NCS$, —$NHC(O)CH_2SCN$, —$NHC(O)CH_2NO$, or —$NHC(O)CHN_2$. In certain embodiments, $R^{11}$ is —$NHC(O)R^{10}$, wherein $R^{10}$ is aliphatic substituted with amino. In certain embodiments, $R^{11}$ is —$NHC(O)CH_2NH_2$. In certain embodiments, $R^{11}$ is —$NHC(O)R^{10}$, wherein $R^{10}$ is aliphatic substituted with hydroxy. In certain embodiments, $R^{11}$ is —$NHC(O)CH_2OH$. In certain embodiments, $R^{11}$ is —$NHC(O)R^{10}$, wherein $R^{10}$ is aliphatic substituted with aryl or heteroaryl. In certain embodiments, $R^{11}$ is —$NHC(O)R^{10}$, wherein $R^{10}$ is —$CH_2$aryl or —$CH_2$heteroaryl. In certain embodiments, $R^{11}$ is —$NHC(O)R^{10}$, wherein $R^{10}$ is aliphatic substituted with optionally substituted heterocyclyl. In certain embodiments, $R^{11}$ is —$NHC(O)R^{10}$, wherein $R^{10}$ is aliphatic substituted with

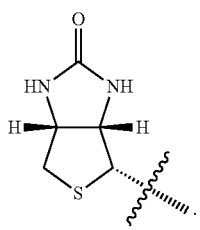

In certain embodiments, $R^{11}$ is

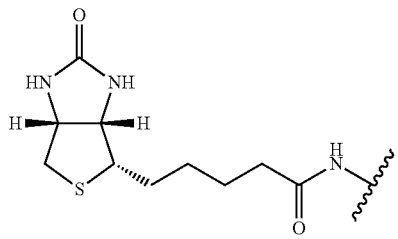

In certain embodiments, $R^{11}$ is —$OR^9$. In certain embodiments, $R^{11}$ is —$OH$. In certain embodiments, $R^{11}$ is —$O$(protecting group). In certain embodiments, $R^{11}$ is —$OAc$. In certain embodiments, $R^{11}$ is —$OC(O)R^{10}$. In certain embodiments, $R^{11}$ is —$OC(O)R^{10}$, wherein $R^{10}$ is optionally substituted aliphatic. In certain embodiments, $R^{11}$ is —$OC(O)CH_3$, or —$OC(O)CH=CH_2$. In certain embodiments, $R^{11}$ is —$OC(O)R^{10}$, wherein $R^{10}$ is aliphatic substituted with halo. In certain embodiments, $R^{11}$ is —$OC(O)R^{10}$, wherein $R^{10}$ is aliphatic substituted with chloro, bromo, or iodo. In certain embodiments, $R^{11}$ is —$OC(O)R^{10}$, wherein $R^{10}$ is aliphatic substituted with fluoro. In certain embodiments, $R^{11}$ is —$OC(O)CH_2Cl$, —$OC(O)CH_2Br$, or —$OC(O)CH_2I$. In certain embodiments, $R^{11}$ is —$OC(O)CH_2CF_3$. In certain embodiments, $R^{11}$ is —$OC(O)R^{10}$, wherein $R^{10}$ is aliphatic substituted with —$N_3$, —$CN$, —$NC$, —$NCO$, —$OCN$, —$NCS$, —$SCN$, —$NO$, or —$N_2$. In certain embodiments, $R^{11}$ is —$OC(O)CH_2N_3$, —$OC(O)CH_2CN$, —$OC(O)CH_2NC$, —$OC(O)CH_2OCN$, —$OC(O)CH_2NCO$, —$OC(O)CH_2NCS$, —$OC(O)CH_2SCN$, —$OC(O)CH_2NO$, or —$OC(O)CHN_2$. In certain embodiments, $R^{11}$ is —$OC(O)R^{10}$, wherein $R^{10}$ is aliphatic substituted with amino. In certain embodiments, $R^{11}$ is —$OC(O)CH_2NH_2$. In certain embodiments, $R^{11}$ is —$OC(O)R^{10}$, wherein $R^{10}$ is aliphatic substituted with hydroxy. In certain embodiments, $R^{11}$ is —$OC(O)CH_2OH$. In certain embodiments, $R^{11}$ is —$OC(O)R^{10}$, wherein $R^{10}$ is aliphatic substituted with aryl or heteroaryl. In certain embodiments, $R^{11}$ is —$OC(O)R^{10}$, wherein $R^{10}$ is —$CH_2$aryl or —$CH_2$heteroaryl. In certain embodiments, $R^{11}$ is —$OC(O)R^{10}$, wherein $R^{10}$ is aliphatic substituted with optionally substituted heterocyclyl. In certain embodiments, $R^{11}$ is —$OC(O)R^{10}$, wherein $R^{10}$ is aliphatic substituted with

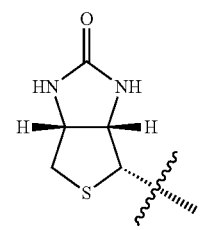

As defined generally above, $R^{12}$ is hydrogen, a hydroxyl protecting group, or optionally substituted aliphatic. In some embodiments, $R^{12}$ is hydrogen. In some embodiments, $R^{12}$ is a hydroxyl protecting group. In some embodiments, $R^{12}$ is optionally substituted aliphatic. In certain embodiments, $R^{12}$ is $C_{1-6}$ alkyl. In certain embodiments, $R^{12}$ is methyl.

As defined generally above, $R^{13}$ is hydrogen, a hydroxyl protecting group, or optionally substituted aliphatic. In some embodiments, $R^{13}$ is hydrogen. In some embodiments, $R^{13}$ is a hydroxyl protecting group. In some embodiments, $R^{13}$ is optionally substituted aliphatic. In certain embodiments, $R^{13}$ is $C_{1-6}$ alkyl. In certain embodiments, $R^{13}$ is methyl.

As defined generally above, $R^{14}$ is hydrogen, a hydroxyl protecting group, or optionally substituted aliphatic. In some embodiments, $R^{14}$ is hydrogen. In some embodiments, $R^{14}$ is a hydroxyl protecting group. In some embodiments, $R^{14}$ is optionally substituted aliphatic. In certain embodiments, $R^{14}$ is $C_{1-6}$ alkyl. In certain embodiments, $R^{14}$ is methyl.

As defined generally above, $R^{15}$ is hydrogen, a hydroxyl protecting group, or optionally substituted aliphatic. In some embodiments, $R^{15}$ is hydrogen. In some embodiments, $R^{15}$ is a hydroxyl protecting group. In some embodiments, $R^{15}$ is optionally substituted aliphatic. In certain embodiments, $R^{15}$ is $C_{1-6}$ alkyl. In certain embodiments, $R^{15}$ is methyl.

In certain embodiments, $R^{12}$, $R^{13}$, $R^{14}$, and $R^{15}$ are all hydrogen.

As defined generally above, $R^a$ is hydrogen or a hydroxyl protecting group. In certain embodiments, $R^a$ is hydrogen. In certain embodiments, $R^a$ is a hydroxyl protecting group.

As defined generally above, $R^b$ is hydrogen or a hydroxyl protecting group. In certain embodiments, $R^b$ is hydrogen. In certain embodiments, $R^b$ is a hydroxyl protecting group.

As defined generally above, G is an optionally substituted $C_{1-30}$ aliphatic group, wherein 0 to 10 methylene units are optionally replaced with —O—, —NR$^x$—, —S—, —C(O)—, —C(=NR$^x$)—, —S(O)—, —SO$_2$—, —N=N—, —C=N—, —N—O—, an optionally substituted arylene, an optionally substituted heterocyclylene, or an optionally substituted heteroarylene; or G is a group of Formula (a), (b), or (c):

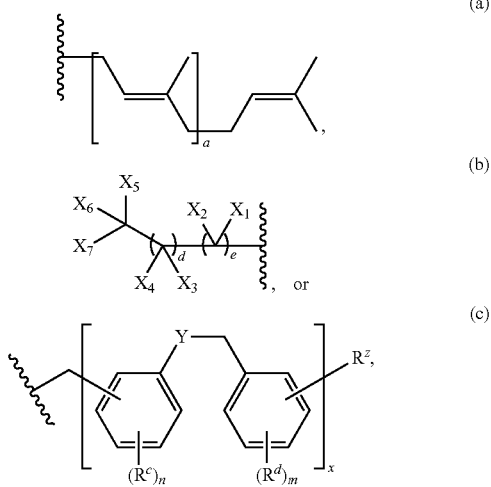

wherein a, $X_1$, $X_2$, $X_3$, $X_4$, $X_5$, $X_6$, $X_7$, d, e, Y, $R^c$, $R^d$, $R^z$, x, m, and n are as described herein.

In certain embodiments, G is an optionally substituted $C_{1-30}$ aliphatic group, wherein 0 to 10 methylene units are optionally replaced with —O—, —NR$^x$—, —S—, —C(O)—, —C(=NR$^x$)—, —S(O)—, —SO$_2$—, —N=N—, —C=N—, —N—O—, an optionally substituted arylene, an optionally substituted heterocyclylene, or an optionally substituted heteroarylene. In certain embodiments, G is an optionally substituted $C_{1-10}$, $C_{5-20}$, $C_{10-20}$, $C_{12-18}$, or $C_{15-20}$ aliphatic group, wherein 0, 1, 2, 3, 4, 5, 6, 7, 8, 9, or 10 methylene units are optionally replaced with —O—, —NR$^x$—, —S—, —C(O)—, —C(=NR$^x$)—, —S(O)—, —SO$_2$—, —N=N—, —C=N—, —N—O—, an optionally substituted arylene, an optionally substituted heterocyclylene, or an optionally substituted heteroarylene.

Exemplary aliphatic moieties include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), hexadecyl ($C_{16}$), heptadecyl ($C_{17}$), octadecyl ($C_{18}$), nonadecyl ($C_{19}$), eicosyl ($C_{20}$), and so on, up to ($C_{30}$). In certain embodiments, the aliphatic moiety is a straight chain alkyl moiety, including, but not limited to, methyl ($C_1$), ethyl ($C_2$), n-propyl ($C_3$), n-butyl ($C_4$), n-pentyl ($C_5$), n-hexyl ($C_6$), n-heptyl ($C_7$), n-octyl ($C_8$), n-nonyl ($C_9$), n-decyl ($C_{10}$), n-undecyl ($C_{11}$), n-dodecyl ($C_{12}$), n-tridecyl ($C_{13}$), n-tetradecyl ($C_{14}$), n-pentadecyl ($C_{15}$), n-hexadecyl ($C_{16}$), n-heptadecyl ($C_{17}$), n-octadecyl ($C_{18}$), n-nonadecyl ($C_{19}$), n-eicosyl ($C_{20}$), and so on, up to ($C_{30}$).

Exemplary substituents include are described throughout, and include optionally substituted aliphatic (e.g., alkyl, alkenyl, alkynyl), optionally substituted heteroaliphatic, optionally substituted aryl, optionally substituted heteroaryl, halogen, —OR$^v$, —N(R$^v$)$_2$, —SR$^v$, —NO$_2$, —NC, —CN, —N$_3$, —N(R$^v$)=NR$^v$, —CHO, —C(=O)R$^v$, —C(=S)R$^v$, —C(=NR$^v$)R$^v$, —C(=O)OR$^q$, —C(=NR$^q$)OR$^q$, —C(=NR$^v$)N(R$^v$)$_2$, —C(=O)N(R$^v$)$_2$, —C(=S)OR$^v$, —C(=O)SR$^v$, —C(=S)SR$^v$, —P(=O)(OR$^v$)$_2$, —P(=O)$_2$(OR$^v$), —S(=O)(OR$^v$), —S(=O)$_2$(OR$^v$), —P(=O)N(R$^v$)$_2$, —P(=O)$_2$N(R$^v$)$_2$, —S(=O)N(R$^v$)$_2$, or —S(=O)$_2$N(R$^v$)$_2$; wherein each instance of R$^v$ is H, optionally substituted aliphatic, optionally substituted heteroaliphatic, optionally substituted aryl, optionally substituted heteroaryl or a protecting group. In certain embodiments, the G hydrocarbon chain is substituted with one or more optionally substituted aliphatic moieties, optionally substituted heteroaliphatic moieties, optionally substituted aryl moieties, optionally substituted heteroaryl moieties, halogen moieties, —OR$^v$ moieties, —N(R$^v$)$_2$ moieties, or —SR$^v$ moieties. In certain embodiments, the G hydrocarbon chain is substituted with one or more optionally substituted aliphatic moieties or —OR$^v$ moieties. In certain embodiments, the G hydrocarbon chain is substituted with one or more optionally substituted aliphatic moieties. In certain embodiments, the G hydrocarbon chain is substituted with one or more optionally substituted $C_{1-6}$ alkyl moieties. In certain embodiments, the G hydrocarbon chain is substituted with one or more —CH$_3$ moieties.

In certain embodiments, G is an optionally substituted, optionally unsaturated, $C_{5-20}$ hydrocarbon chain, wherein 0 to 10 methylene units are optionally replaced with —O—, —NR$^x$—, —S—, —C(O)—, —C(=NR$^x$)—, —S(O)—, —SO$_2$—, —N=N—, —C=N—, —N—O—, an optionally substituted arylene, an optionally substituted heterocyclylene, or an optionally substituted heteroarylene.

In certain embodiments, G is an optionally substituted, optionally unsaturated, $C_{10-20}$ hydrocarbon chain, wherein 0 to 8 methylene units are optionally replaced with —O—, —NR$^x$—, —S—, —C(O)—, —C(=NR$^x$)—, —S(O)—, —SO$_2$—, —N=N—, —C=N—, —N—O—, an optionally substituted arylene, an optionally substituted heterocyclylene, or an optionally substituted heteroarylene.

In certain embodiments, G is an optionally substituted, optionally unsaturated, C10-18 hydrocarbon chain, wherein 0 to 6 methylene units are optionally replaced with —O—, —NR$^x$—, —S—, —C(O)—, —C(=NR$^x$)—, —S(O)—, —SO$_2$—, —N=N—, —C=N—, —N—O—, an optionally substituted arylene, an optionally substituted heterocyclylene, or an optionally substituted heteroarylene.

In certain embodiments, G is an unsubstituted, optionally unsaturated hydrocarbon chain.

In certain embodiments, G is an unsubstituted and saturated hydrocarbon chain. In certain embodiments, G is an unsubstituted hydrocarbon and saturated hydrocarbon chain wherein 0 to 10 methylene units are replaced with —O—, —NR$^x$—, —S—, —C(=O)—, —C(=NR$^x$)—, —S(=O)—, —S(=O)$_2$— or —N—O—.

In certain embodiments, G is an unsubstituted and unsaturated hydrocarbon chain. In certain embodiments, G is an unsubstituted hydrocarbon and unsaturated hydrocarbon chain, wherein 1 to 10 methylene units are replaced with —O—, —NR$^x$—, —S—, —C(O)—, —C(=NR$^x$), —S(O)—, —SO$_2$—, —N=N—, —C=N—, —N—O—, an optionally substituted arylene, an optionally substituted heterocyclylene, or an optionally substituted heteroarylene.

In certain embodiments, G is a substituted and saturated hydrocarbon chain. In certain embodiments, G is a substituted and saturated hydrocarbon chain, wherein 0 to 10 methylene units are replaced with —O—, —NR$^x$—, —S—, —C(=O)—, —C(=NR$^x$)—, —S(=O)—, —S(=O)$_2$— or —N—O—.

In certain embodiments, G is a substituted, optionally unsaturated hydrocarbon chain. In certain embodiments, G is a substituted and unsaturated hydrocarbon chain. In certain embodiments, G is a substituted hydrocarbon and unsaturated hydrocarbon chain wherein 1 to 10 methylene units are replaced with —O—, —NR$^x$—, —S—, —C(O)—, —C(=NR$^x$), —S(O)—, —SO$_2$—, —N=N—, —C=N—, —N—O—, an optionally substituted arylene, an optionally substituted heterocyclylene, or an optionally substituted heteroarylene.

In certain embodiments, G is an optionally substituted, optionally unsaturated, $C_{10}$-$C_{16}$ aliphatic moiety. In certain embodiments, G is an optionally substituted, $C_8$-$C_{16}$ alkyl moiety. In certain embodiments, G is an optionally substituted, $C_{10}$-$C_{14}$ alkyl moiety.

In certain embodiments, G is:

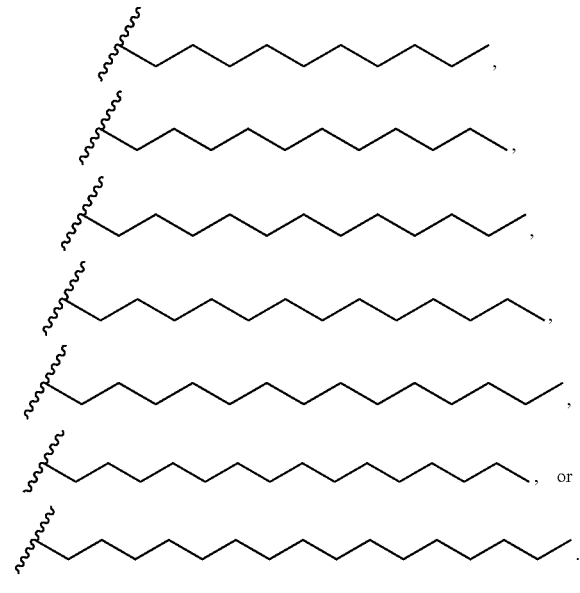

In certain embodiments, G is:

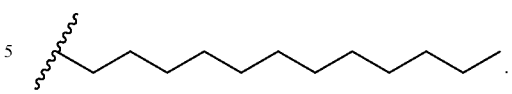

In certain embodiments, G is fluorinated. G may be perfluorinated or partially fluorinated. In certain embodiments, all the hydrogen atoms of G are replaced with fluorine atoms. In certain embodiments, only a portion of the hydrogen atoms of G are replaced with fluorine atoms. In certain embodiments, at least 10%, at least 20%, at least 30%, at least 40%, at least 50%, at least 60%, at least 70%, at least 80%, or at least 80% of the hydrogen atoms are replaced with fluorine atoms. In certain embodiments, G comprises at least 1, 2, 3, 4, 5, 6, 7, 8, 9, 10, 15, 20, or more fluorine atoms. In certain embodiments, G may include substituents that are or are not fluorinated. In certain embodiments, G is a fluorinated, optionally unsaturated, $C_{10}$-$C_{16}$ aliphatic moiety. In certain embodiments, G is a perfluorinated, optionally unsaturated, $C_{10}$-$C_{16}$ aliphatic moiety. In certain embodiments, G is a partially fluorinated, optionally unsaturated, $C_{10}$-$C_{16}$ aliphatic moiety. In certain embodiments, G is a fluorinated, $C_8$-$C_{16}$ alkyl moiety. In certain embodiments, G is a perfluorinated, $C_8$-$C_{16}$ alkyl moiety. In certain embodiments, G is a partially fluorinated, $C_8$-$C_{16}$ alkyl moiety. In certain embodiments, G is a fluorinated, $C_{10}$-$C_{14}$ alkyl moiety. In certain embodiments, G is a perfluorinated, $C_{10}$-$C_{14}$ alkyl moiety. In certain embodiments, G is a partially fluorinated, $C_{10}$-$C_{14}$ alkyl moiety.

In certain embodiments, G is a perfluorinated, optionally unsaturated $C_{10}$-$C_{16}$ alkyl moiety. In certain embodiments, G is:

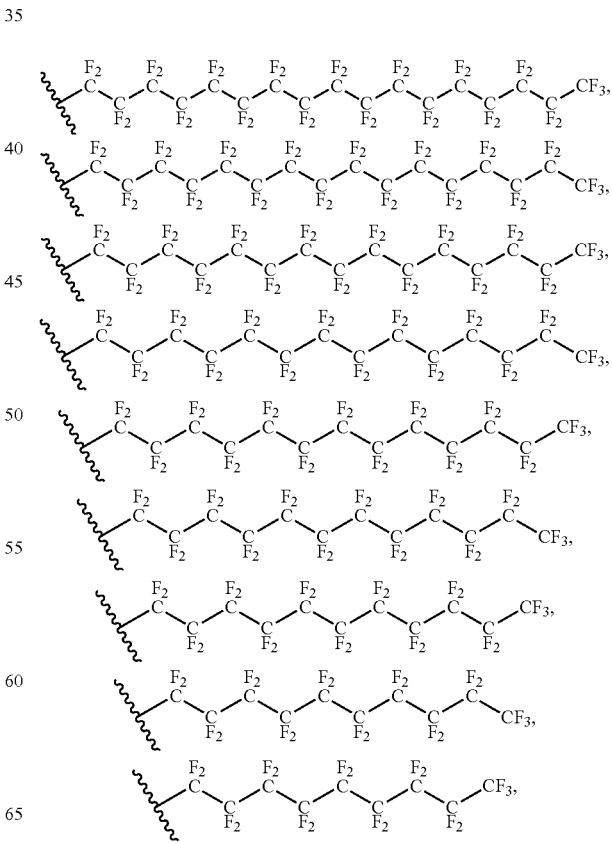

-continued

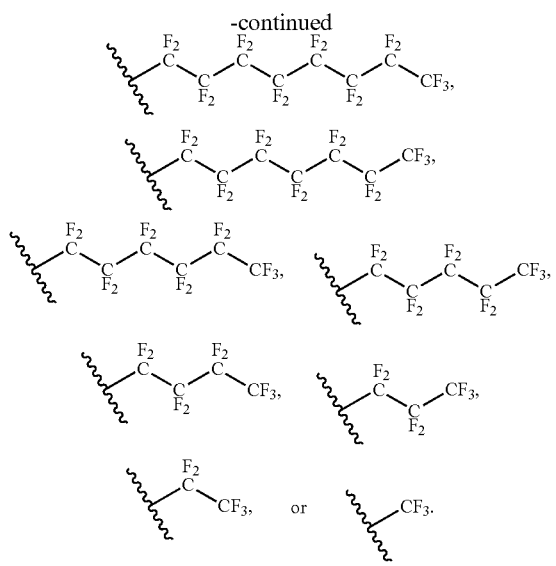

In certain embodiments, G is:

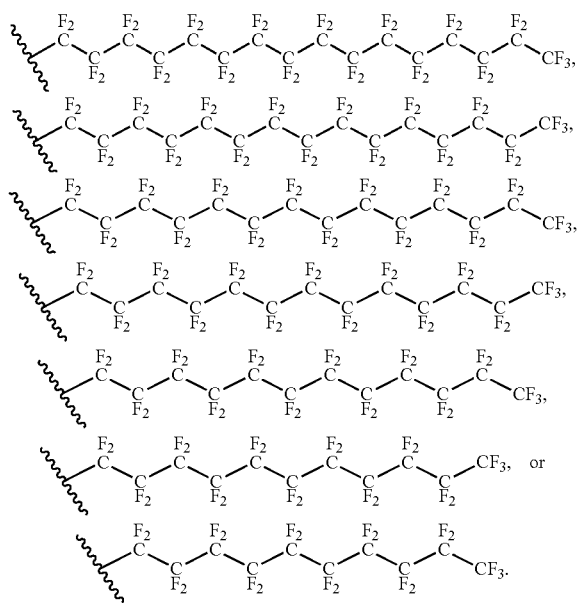

In certain embodiments, G is:

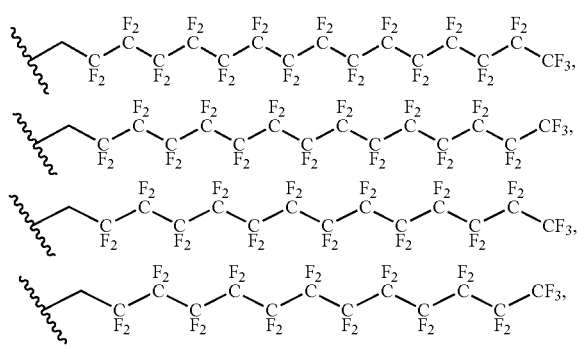

-continued

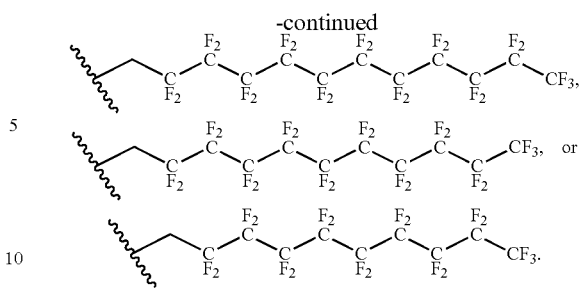

In certain embodiments, G is a substituted or unsubstituted optionally unsaturated $C_{2-30}$ hydrocarbon chain of the formulae:

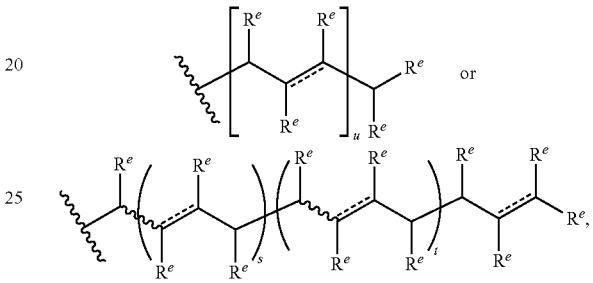

wherein ⌇ is a single or double bond, and each instance of $R^e$ is, independently, H, optionally substituted aliphatic, optionally substituted heteroaliphatic, optionally substituted aryl, optionally substituted heteroaryl, halogen, —$OR^v$, —$N(R^v)_2$, —$SR^v$, —$NO_2$, —NC, —CN, —$N_3$, —$N(R^v)$=$NR^v$, —CHO, —C(=O)$R^v$, —C(=S)$R^v$, —C(=$NR^v$)$R^v$, —C(=O)$OR^q$, —C(=$NR^q$)$OR^q$, —C(=$NR^v$)$N(R^v)_2$, —C(=O)$N(R^v)_2$, —C(=S)$OR^v$, —C(=O)$SR^v$, —C(=S)$SR^v$, —P(=O)($OR^v$)$_2$, —P(=O)$_2$($OR^v$), —S(=O)($OR^v$), —S(=O)$_2$($OR^v$), —P(=O)$N(R^v)_2$, —P(=O)$_2N(R^v)_2$, —S(=O)$N(R^v)_2$, or —S(=O)$_2N(R^v)_2$; wherein each instance of $R^v$ is H, optionally substituted aliphatic, optionally substituted heteroaliphatic, optionally substituted aryl, optionally substituted heteroaryl or a protecting group; and each instance of u, s and t is, independently, 0, 1, 2, 3, 4, or 5.

In certain embodiments, $R^e$ is, independently, H or optionally substituted aliphatic, optionally substituted heteroaliphatic, optionally substituted aryl, optionally substituted heteroaryl, halogen, —$OR^v$ or —$N(R^v)_2$. In certain embodiments, $R^e$ is, independently, H, optionally substituted aliphatic, optionally substituted heteroaliphatic, optionally substituted aryl or optionally substituted heteroaryl. In certain embodiments, $R^e$ is, independently, optionally substituted aliphatic or optionally substituted heteroaliphatic. In certain embodiments, $R^e$ is, independently, H or optionally substituted aliphatic. In certain embodiments, $R^e$ is, independently, H or —$CH_3$.

In certain embodiments, G is a fully saturated hydrocarbon group of the formula:

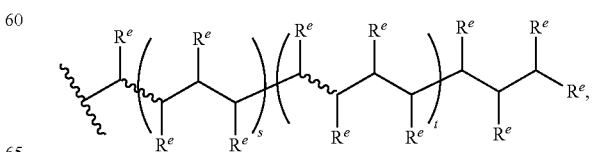

wherein $R^e$, s and t are as defined above and herein.

In certain embodiments, G is a fully saturated hydrocarbon group of the formulae:

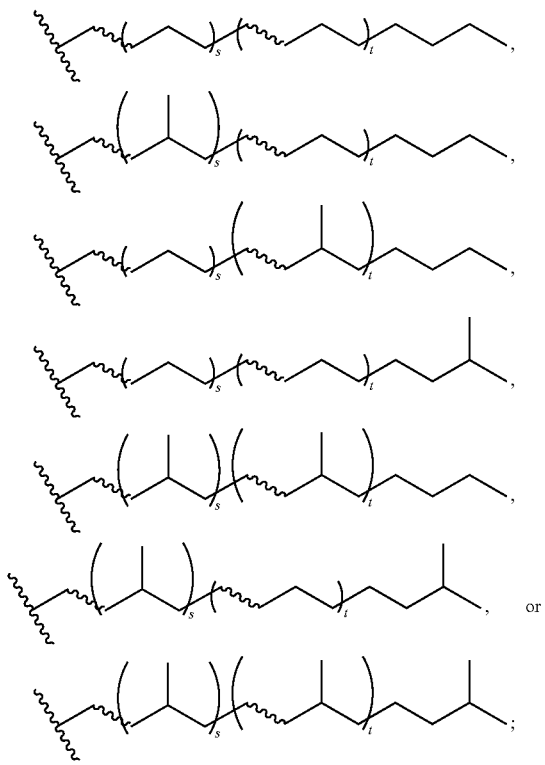

wherein s and t are as defined above and herein.

In certain embodiments, G is an unsaturated group of the formulae:

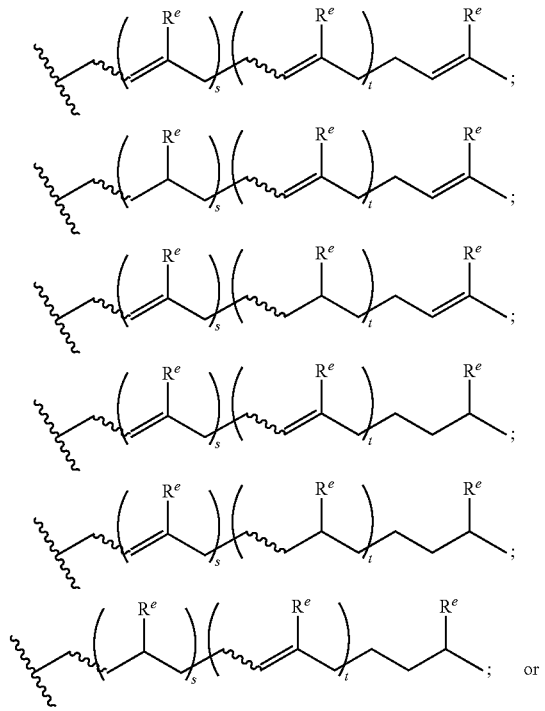

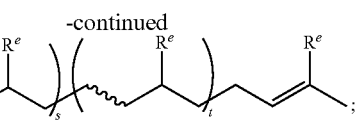

wherein $R^e$, s, and t are as defined herein.

In certain embodiments, G is a group of the formula:

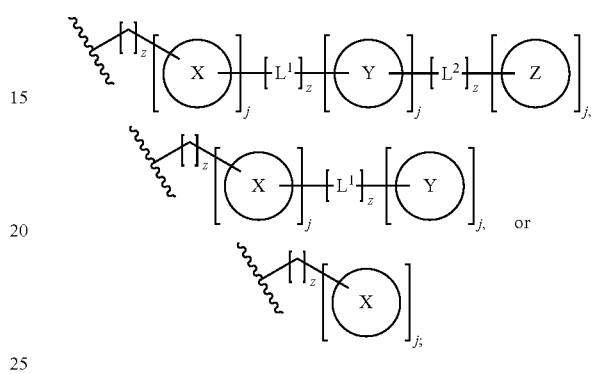

wherein Ring X, Ring Y and Ring Z are, independently, an optionally substituted arylene or an optionally substituted heteroarylene moiety;

z is 0 to 3;

each instance of j is, independently, 1 or 2; and each instance of $L^1$ and $L^2$ are, independently, —(C($R^o$)$_2$)—, —O—, —NR$^x$—, —S—, —C(=O)—, —C(=O)O—, —C(=O)NR$^x$—, —C(=O)S—, —C(=NR$^x$)—, —C(=NR$^x$)O—, —C(=NR$^x$)NR$^x$—, —C(=NR$^x$)S—, —S(=O)—, —S(=O)$_2$—, —N=N—, —C=N—, —C($R^y$)=C($R^y$)—, or —N—O—, wherein $R^o$ is H, optionally substituted aliphatic, optionally substituted heteroaliphatic, optionally substituted aryl, optionally substituted heteroaryl, each instance of $R^x$ is, independently, H, optionally substituted aliphatic, optionally substituted heteroaliphatic, optionally substituted aryl, optionally substituted heteroaryl or an amino protecting group, and each instance of $R^y$ is, independently, H, optionally substituted aliphatic, optionally substituted heteroaliphatic, optionally substituted aryl, or optionally substituted heteroaryl.

Exemplary optionally substituted arylene groups include, but are not limited to:

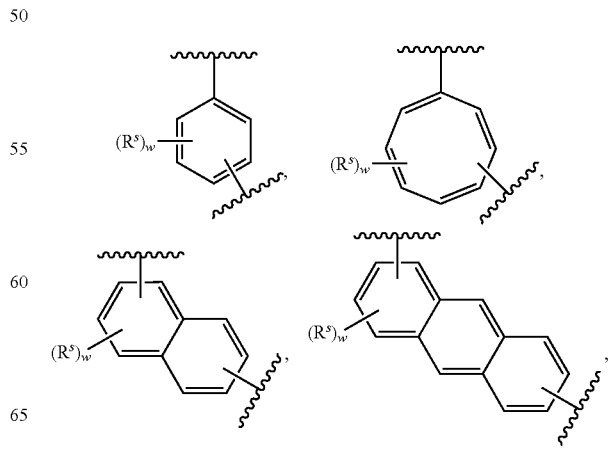

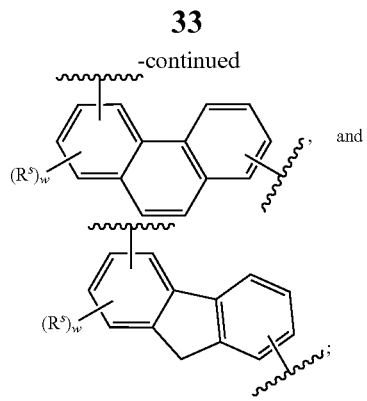

wherein each instance of $R^s$ is, independently, optionally substituted aliphatic, optionally substituted heteroaliphatic, optionally substituted aryl, optionally substituted heteroaryl, halogen, $-OR^v$, $-N(R^v)_2$, $-SR^v$, $-NO_2$, $-NC$, $-CN$, $-N_3$, $-N(R^v)=NR^v$, $-CHO$, $-C(=O)R^v$, $-C(=S)R^v$, $-C(=NR^v)R^v$, $C(=O)OR^q$, $C(=NR^q)OR^q$, $-C(=NR^v)N(R^v)_2$, $-C(=O)N(R^v)_2$, $-C(=S)OR^v$, $-C(=O)SR^v$, $-C(=S)SR^v$, $-P(=O)(OR^v)_2$, $-P(=O)_2(OR^v)$, $-S(=O)(OR^v)$, $-S(=O)_2(OR^v)$, $-P(=O)N(R^v)_2$, $-P(=O)_2N(R^v)_2$, $-S(=O)N(R^v)_2$, or $-S(=O)_2N(R^v)_2$; wherein each instance of $R^v$ is H, optionally substituted aliphatic, optionally substituted heteroaliphatic, optionally substituted aryl, optionally substituted heteroaryl or a protecting group; and w is an integer between 0 to 10, inclusive.

Exemplary optionally substituted heteroarylene groups include, but are not limited to:

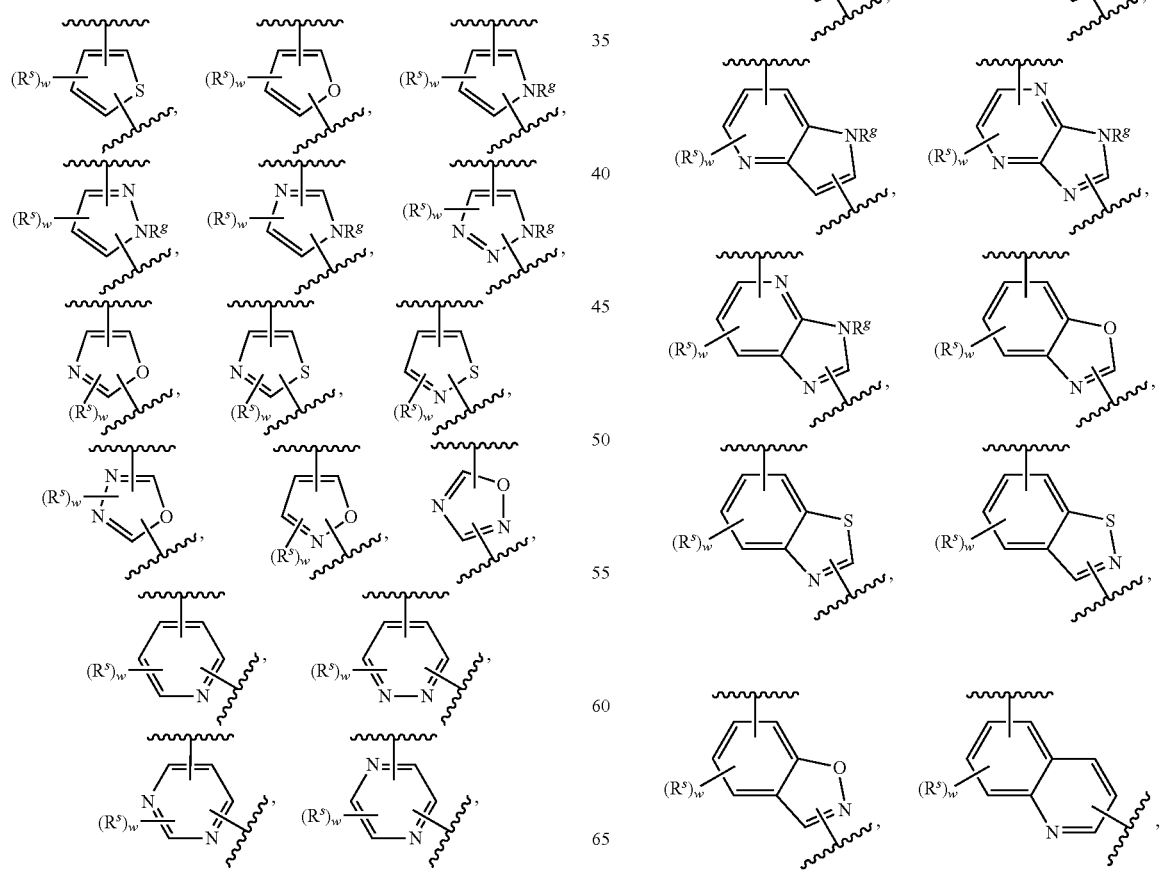

-continued

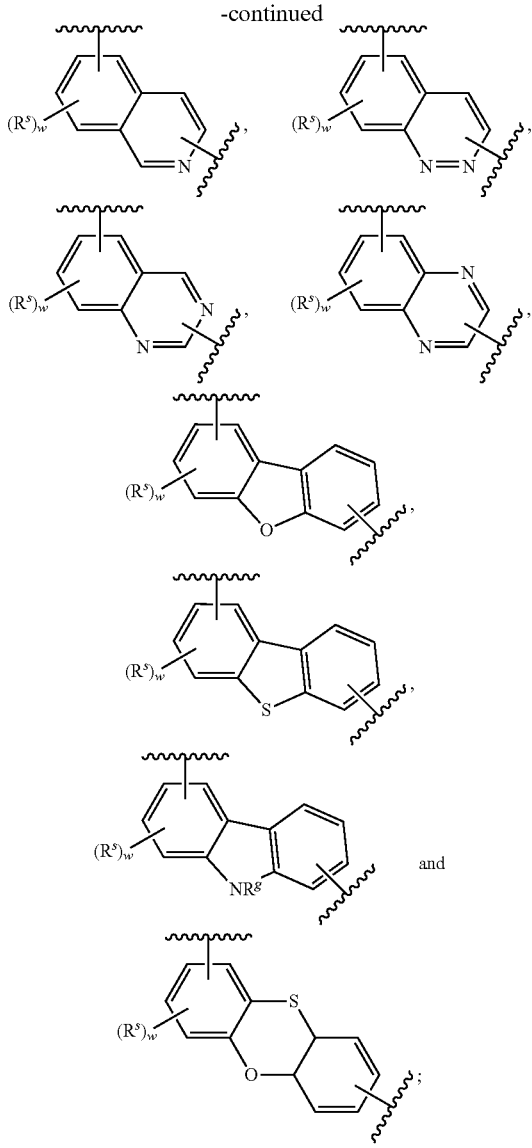

wherein each instance of $R^s$ is, independently, optionally substituted aliphatic, optionally substituted heteroaliphatic, optionally substituted aryl, optionally substituted heteroaryl, halogen, —$OR^v$, —$N(R^v)_2$, —$SR^v$, —$NO_2$, —NC, —CN, —$N_3$, —$N(R^v)$=$NR^v$, —CHO, —C(=O)$R^v$, —C(=S)$R^v$, —C(=$NR^v$)$R^v$, —C(=O)$OR^q$, —C(=$NR^q$)$OR^q$, —C(=$NR^v$)$N(R^v)_2$, —C(=O)$N(R^v)_2$, —C(=S)$OR^v$, —C(=O)$SR^v$, —C(=S)$SR^v$, —P(=O)$(OR^v)_2$, —P(=O)$_2$(O$R^v$), —S(=O)(O$R^v$), —S(=O)$_2$(O$R^v$), —P(=O)$N(R^v)_2$, —P(=O)$_2N(R^v)_2$, —S(=O)$N(R^v)_2$, or —S(=O)$_2N(R^v)_2$; wherein each instance of $R^v$ is H, optionally substituted aliphatic, optionally substituted heteroaliphatic, optionally substituted aryl, optionally substituted heteroaryl or a protecting group; and w is an integer between 0 to 10, inclusive; and each instance of $R^g$ is, independently, H, optionally substituted aliphatic, optionally substituted heteroaliphatic, optionally substituted aryl, optionally substituted heteroaryl or an amino protecting group.

In certain embodiments, Ring X, Ring Y and Ring Z are, independently, an optionally substituted arylene moiety. In certain embodiments, Ring X, Ring Y and Ring Z are, independently, an optionally substituted phenylene moiety. For example, in certain embodiments, G is an group of the formulae:

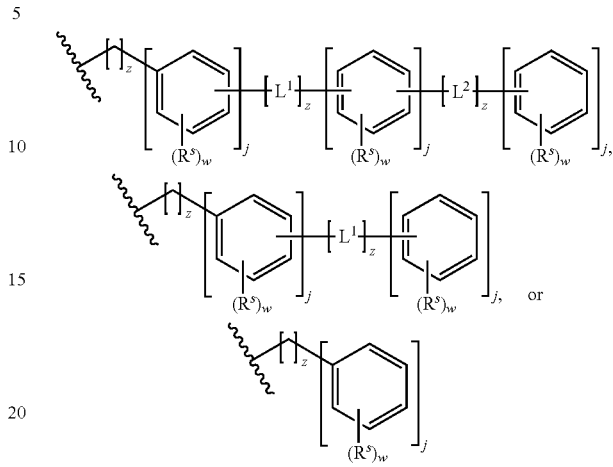

wherein z, w, j, $L^1$, $L^2$, and $R^s$ are as defined above and herein.

In certain embodiments, G is of one of the formulae:

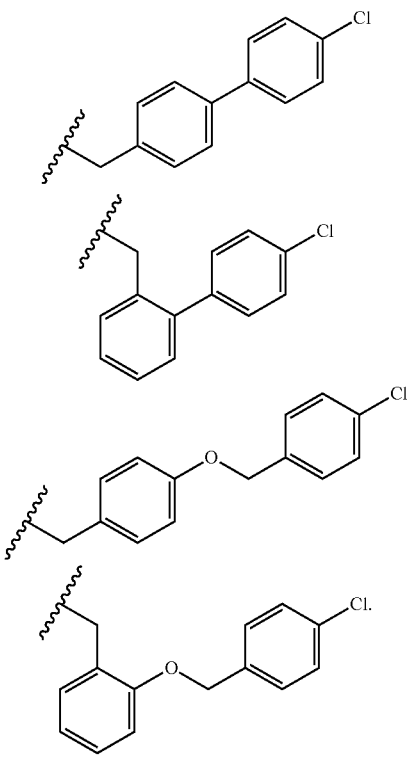

In certain embodiments, G is any one of the following groups:

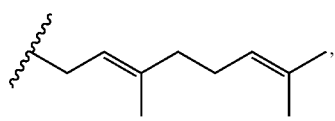

-continued

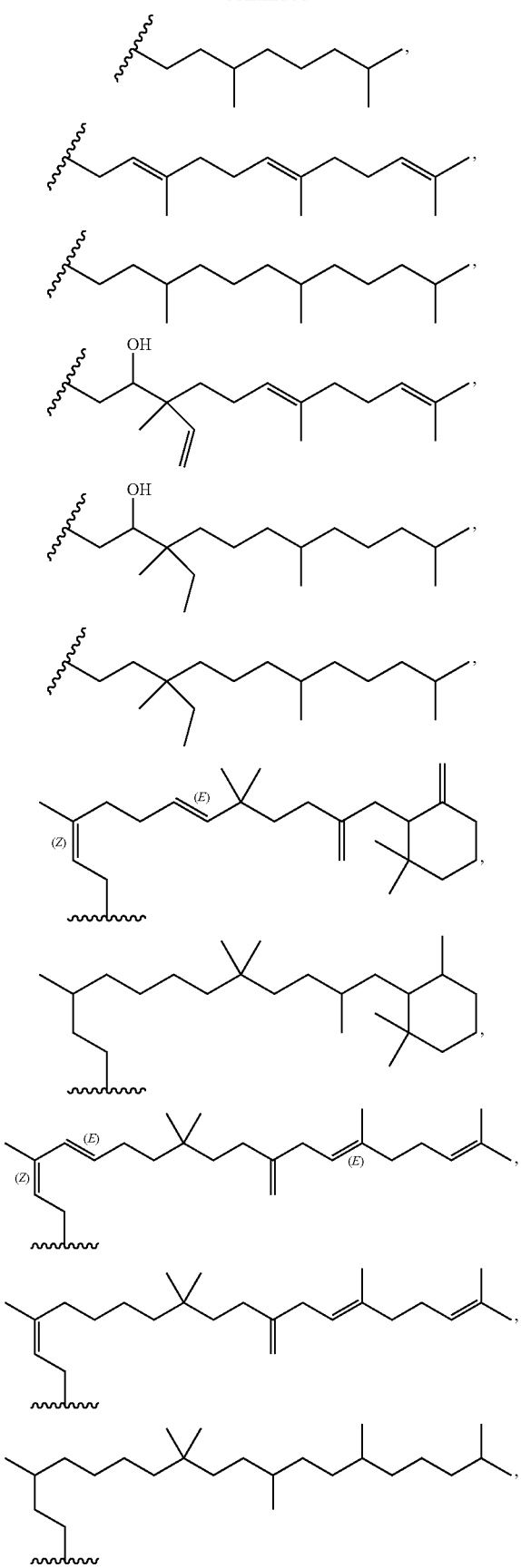

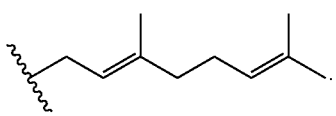 [SMILES: *C/C=C(\C)CCC=C(C)C]

and

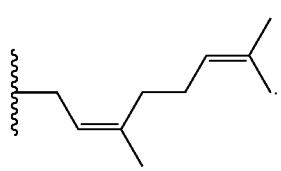

In certain embodiments, G is the geranyl group:

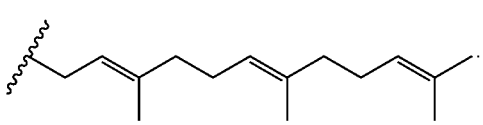 [SMILES: *C/C=C(\C)CC/C=C(\C)CCC=C(C)C]

In certain embodiments, G is the farnesyl group:

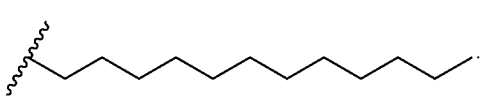 [SMILES: *CCCCCCCCCCCC]

In certain embodiments, G is $C_{12}$ alkyl of the formula:

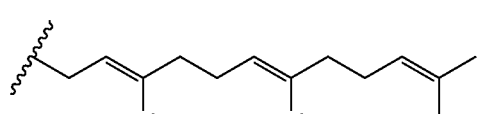

In certain embodiments, G is the nerolyl group:

In certain embodiments, G is of the formula:

wherein each occurrence of $R^e$ is independently hydrogen or an optionally substituted aliphatic moiety. In certain embodiments, $R^e$ is hydrogen or $C_1$-$C_6$ aliphatic. In certain embodiments, Re is hydrogen, $C_1$-$C_6$ alkyl, or $C_1$-$C_6$ alkenyl. In certain embodiments, $R^e$ is vinyl. In certain embodiments, $R^e$ is allyl. In certain embodiments, $R^e$ is isopropyl. In certain embodiments, $R^e$ is n-propyl. In certain embodiments, $R^e$ is isobutyl. In certain embodiments, $R^e$ is n-butyl. In certain embodiments, $R^e$ is t-butyl. In certain embodiments, $R^e$ is n-pentyl. In certain embodiments, $R^e$ is isopentyl. In certain embodiments, $R^e$ is neopentyl. In certain embodiments, $R^e$ is 3-methyl-but-2-enyl. Exemplary G groups include:
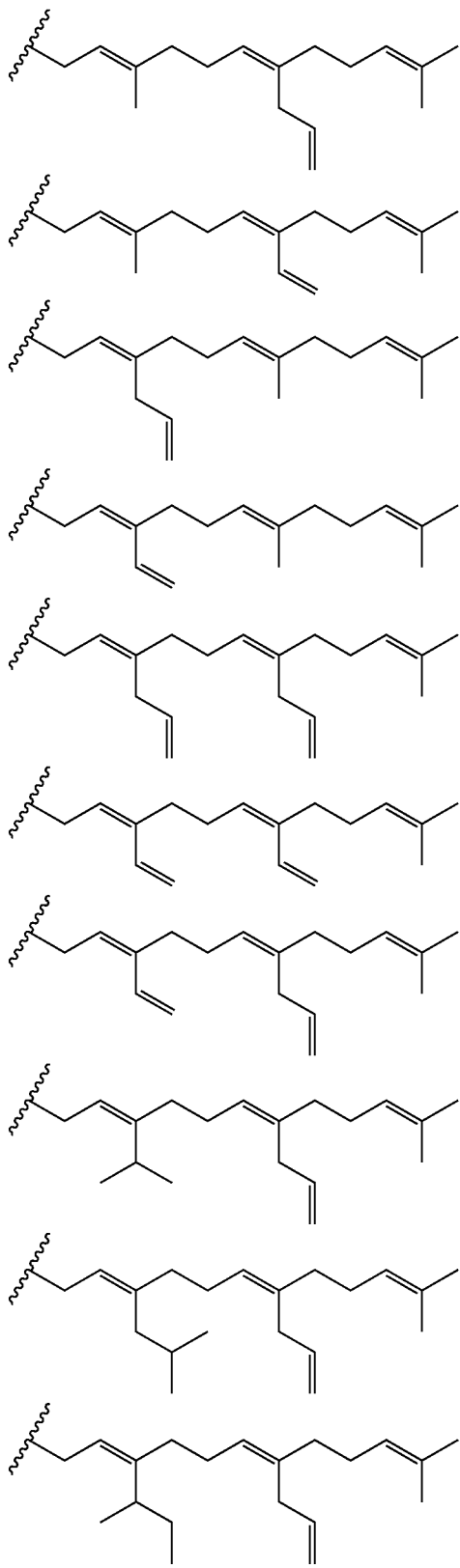
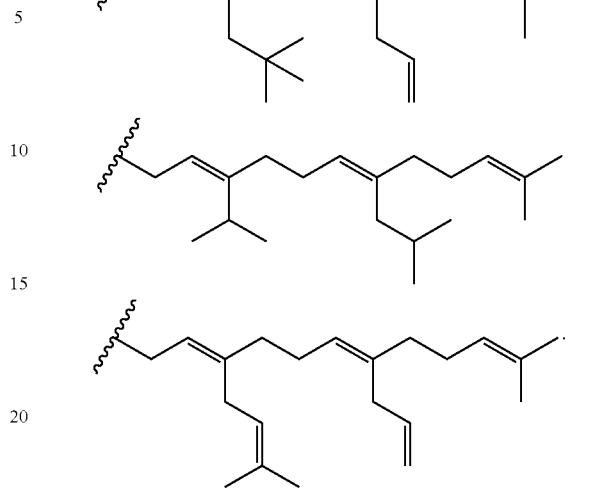
In certain embodiments, G is of the formula:
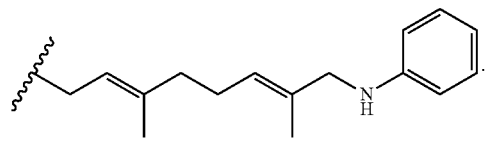 [SMILES: *C/C=C(\C)CC/C=C(\C)CNc1ccccc1]
In some embodiments, G is of Formula (a):
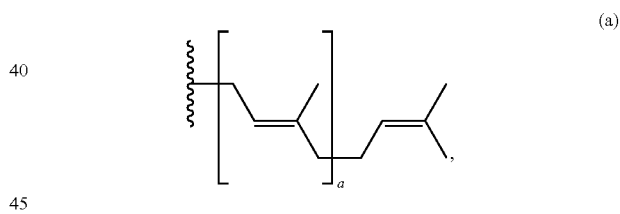
wherein a is 3, 4, or 5.
For example, in certain embodiments, G is:
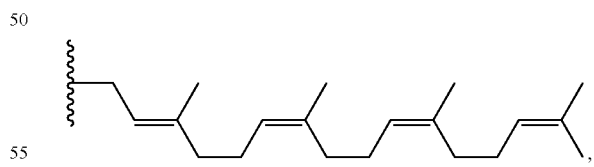
wherein a is 3;
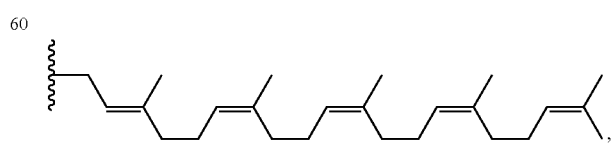
wherein a is 4; or

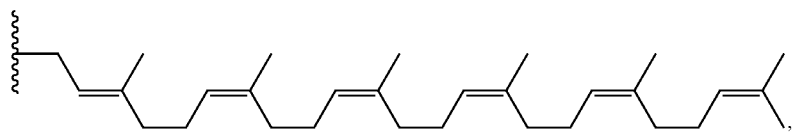

wherein a is 5.

In some embodiments, G is of Formula (b):

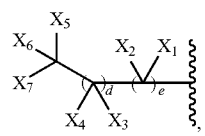

(b)

wherein:

$X_1$, $X_2$, $X_3$, $X_4$, $X_5$, $X_6$, and $X_7$ are each independently hydrogen or halogen;

d is an integer between 1 and 25, inclusive; and e is an integer of between 2 and 25, inclusive;

provided the sum of d and e is greater than 16.

In certain embodiments, e is 2, 3, 4, 5, 6, 7, 8, 9, 10, 11, 12, 13, 14, 15, 16, 17, 18, 19, 20, 21, 22, 23 24, or 25. In certain embodiments, d is 1, 2, 3, 4, 5, 6, 7, 8, 9, 10, 11, 12, 13, 14, 15, 16, 17, 18, 19, 20, 21, 22, 23 24, or 25. Any particular combination of e or d is contemplated, provided the sum of d and e is greater than 16.

For example, in certain embodiments, e is 16 or an integer greater than 16, and d is 1 or an integer greater than 1. In certain embodiments, e is 15, and d is 2 or an integer greater than 2. In certain embodiments, e is 14, and d is 3 or an integer greater than 3. In certain embodiments, e is 13, and d is 4 or an integer greater than 4. In certain embodiments, e is 12, and d is 5 or an integer greater than 5. In certain embodiments, e is 11, and d is 6 or an integer greater than 6. In certain embodiments, e is 10, and d is 7 or an integer greater than 7. In certain embodiments, e is 9, and d is 8 or an integer greater than 8. In certain embodiments, e is 8, and d is 9 or an integer greater than 9. In certain embodiments, e is 7, and d is 10 or an integer greater than 10. In certain embodiments, e is 6, and d is 11 or an integer greater than 11. In certain embodiments, e is 5, and d is 12 or an integer greater than 12. In certain embodiments, e is 4, and d is 13 or an integer greater than 13. In certain embodiments, e is 3, and d is 14 or an integer greater than 14. In certain embodiments, e is 2, and d is 15 or an integer greater than 15. In certain embodiments, e is 10, and d is 7 or an integer greater than 7, e.g., d is 7, 8, 9, 10, 11, 12, 13, 14, 15, 16, 17, 18, 19, 20, 21, 22, 23 24, or 25. In certain embodiments, e is 10 and d is 7. In certain embodiments, e is 10 and d is 8. In certain embodiments, e is 10 and d is 9. In certain embodiments, e is 10 and d is 10. In certain embodiments, e is 10 and d is 11. In certain embodiments, e is 10 and d is 12. In certain embodiments, e is 10 and d is 13. In certain embodiments, e is 10 and d is 14. In certain embodiments, e is 10 and d is 15.

In certain embodiments, each instance of $X_1$ and $X_2$ is hydrogen. In certain embodiments, each instance of $X_1$ and $X_2$ is halogen, e.g., fluoro.

In certain embodiments, each instance of $X_3$ and $X_4$ is hydrogen. In certain embodiments, each instance of $X_3$ and $X_4$ is halogen, e.g., fluoro.

In certain embodiments, each instance of $X_5$, $X_6$, and $X_7$ is hydrogen. In certain embodiments, each instance of $X_5$, $X_6$, and $X_7$ is halogen, e.g., fluoro.

In certain embodiments, each instance of $X_1$, $X_2$, $X_3$, $X_4$, $X_5$, $X_6$, and $X_7$ is hydrogen, i.e., to provide an n-alkyl group. Exemplary n-alkyl groups of Formula (b) include, but are not limited to:

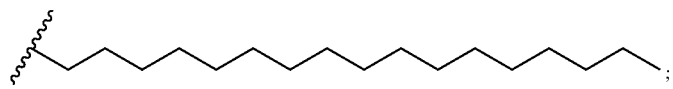

$C_{17}$-n-alkyl

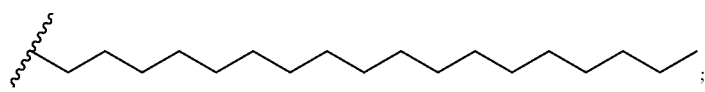

$C_{18}$-n-alkyl

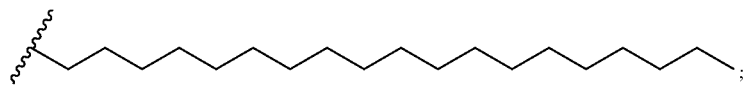

$C_{19}$-n-alkyl

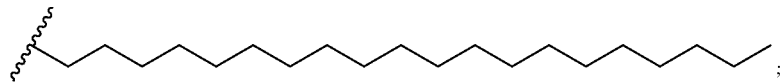

$C_{20}$-n-alkyl

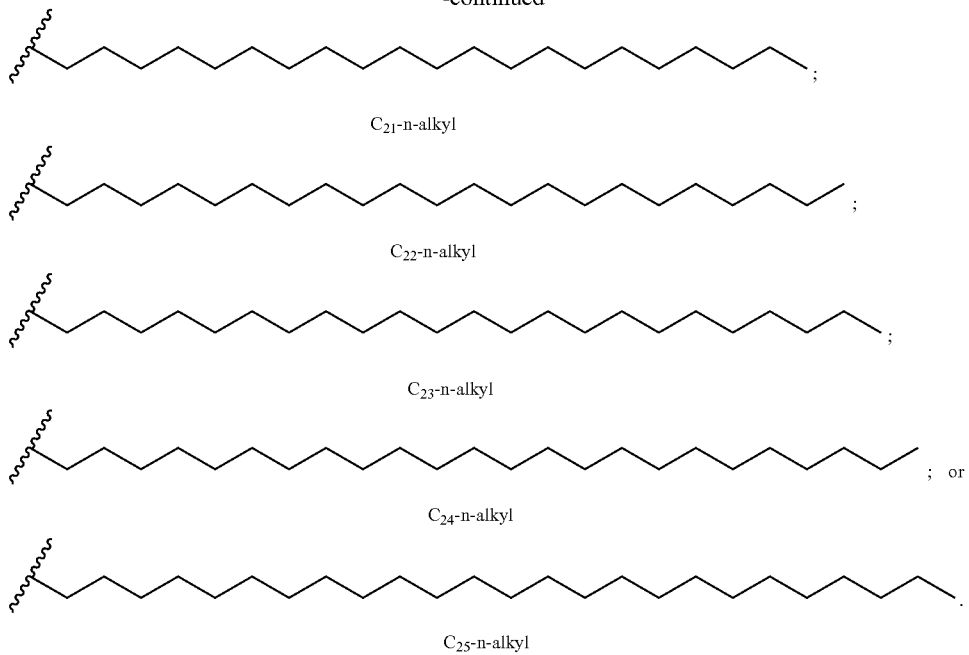

C₂₁-n-alkyl;

C₂₂-n-alkyl;

C₂₃-n-alkyl;

C₂₄-n-alkyl; or

C₂₅-n-alkyl.

In certain embodiments, each instance of $X_1$ and $X_2$ is fluoro, optionally wherein each instance of $X_3$ and $X_4$ is fluoro and/or each instance of $X_5$, $X_6$, and $X_7$ is fluoro. Alternatively, each instance of $X_3$ and $X_4$ is fluoro, optionally wherein each instance of $X_1$ and $X_2$ is fluoro and/or each instance of $X_5$, $X_6$, and $X_7$ is fluoro. In certain embodiments, $X_1$ and $X_2$ are each hydrogen, $X_3$ and $X_4$ are each fluoro, and $X_5$, $X_6$, and $X_7$ are each fluoro. In certain embodiments, $X_1$, $X_2$ are each fluoro, $X_3$ and $X_4$ are each hydrogen, and $X_5$, $X_6$, and $X_7$ are each hydrogen.

Exemplary fluoroalkyl groups of formula (b), wherein $X_1$ and $X_2$ are hydrogen and $X_3$, $X_4$, $X_5$, $X_6$, and $X_7$ are each fluoro include, but are not limited to:

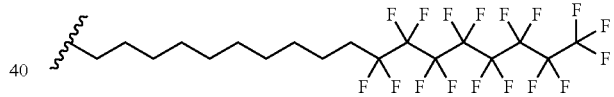

wherein e is 10, and d is 7;

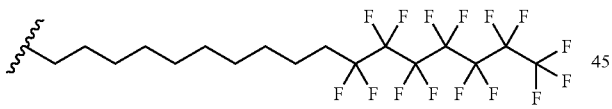

wherein e is 10, and d is 8;

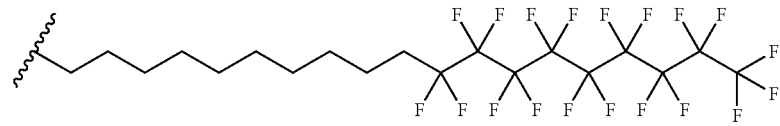

wherein e is 10, and d is 9;

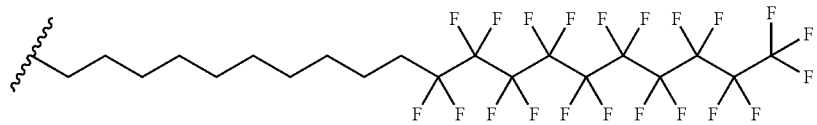

wherein e is 10, and d is 10;
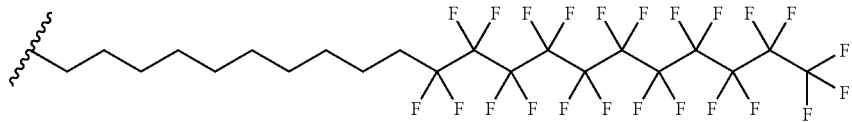
wherein e is 10, and d is 11;
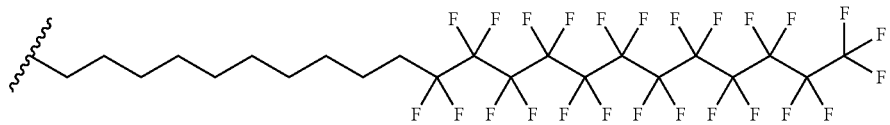
wherein e is 10, and d is 12;
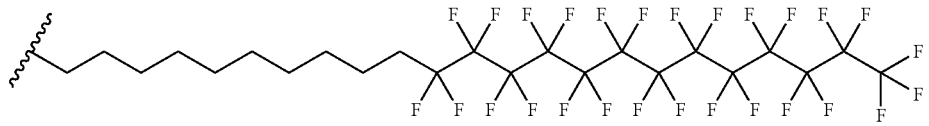
wherein e is 10, and d is 13;
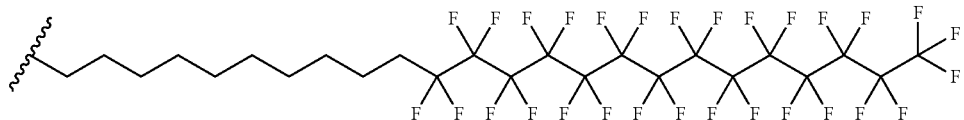
wherein e is 10, and d is 14;
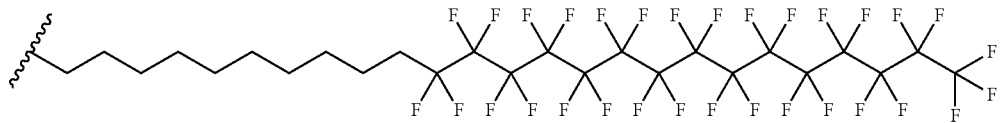
wherein e is 10, and d is 15.
Exemplary fluoroalkyl groups of formula (b), wherein each instance of $X_1$, $X_2$, $X_3$, $X_4$, $X_5$, $X_6$, and $X_7$ is fluoro, include but are not limited to:
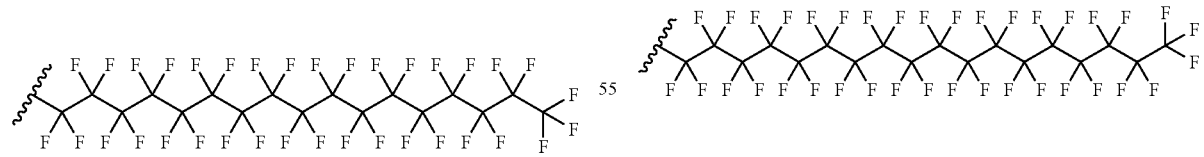
wherein e is 10, and d is 7;
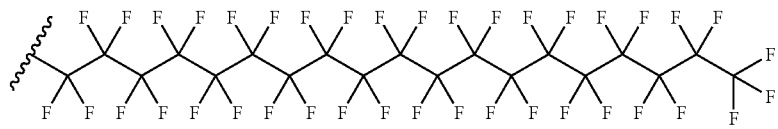
wherein e is 10, and d is 8;

wherein e is 10, and d is 9;
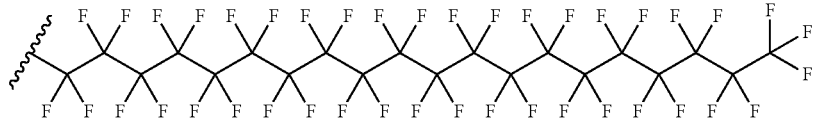
wherein e is 10, and d is 10;
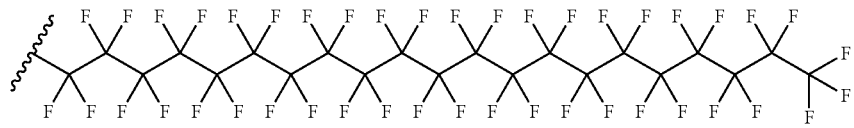
wherein e is 10, and d is 11;
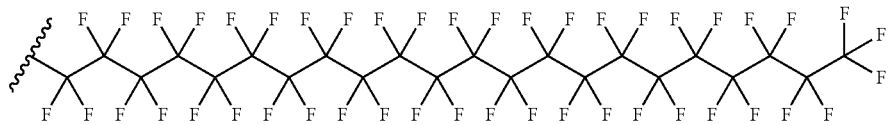
wherein e is 10, and d is 12;
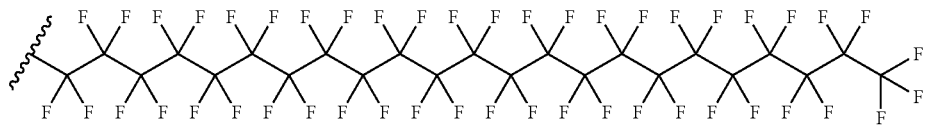
wherein e is 10, and d is 13;
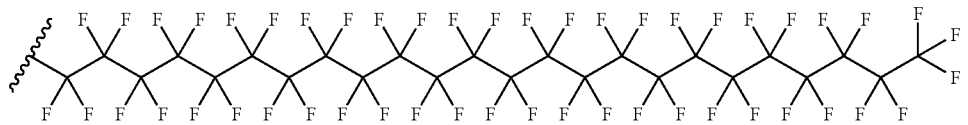
wherein e is 10, and d is 14;
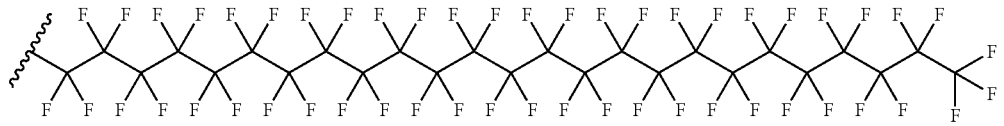
wherein e is 10, and d is 15.

In some embodiments G is of Formula (c):

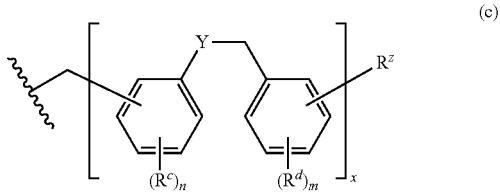

wherein:
Y is —O—, —S—, —NR$^Y$—, or an optionally substituted methylene group, wherein R$^Y$ is hydrogen, optionally substituted aliphatic, or an amino protecting group;
each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, and —N(R$^e$)$_2$, wherein each instance of R$^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^e$ groups are joined to form a 5- to 6-membered optionally substituted heterocycyl or optionally substituted heteroaryl ring;
each instance of R$^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^f$, —SR$^f$, —NHR$^f$, or —N(R$^f$)$_2$, wherein each instance of R$^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^f$ groups are joined to form a 5- to 6-membered optionally substituted heterocycyl or optionally substituted heteroaryl ring;
R$^z$ is hydrogen, —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^g$, —SR$^g$, —NHR$^g$, or —N(R$^g$)$_2$, wherein each instance of R$^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two R$^g$ groups are joined to form a 5- to 6-membered optionally substituted heterocycyl or optionally substituted heteroaryl ring;
each instance of n is, independently, 0, 1, 2, 3, or 4;
each instance of m is, independently, 0, 1, 2, 3, or 4; and
x is 1, 2, 3, 4, 5, or 6.

As generally defined above, Y is —O—, —S—, —NR$^Y$—, or an optionally substituted methylene group, wherein R$^Y$ is hydrogen, optionally substituted aliphatic, or an amino protecting group. In certain embodiments, Y is —O—. In certain embodiments, Y is —S—. In certain embodiments, Y is —NR$^Y$—. In certain embodiments, Y is an optionally substituted methylene group, e.g., —CH$_2$—.

As generally defined above, each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, or —N(R$^e$)$_2$, wherein each instance of R$^e$ is independently hydrogen, optionally substituted aliphatic, optionally substituted heteroaliphatic, optionally substituted carbocycyl, heterocycyl, optionally substituted aryl, or optionally substituted heteroaryl, or two R$^e$ groups are joined to form a 5- to 6-membered optionally substituted heterocycyl or optionally substituted heteroaryl ring; and n is 0, 1, 2, 3, or 4.

In certain embodiments, each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, or —N(R$^e$)$_2$, wherein each instance of R$^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^e$ groups are joined to form a 5- to 6-membered optionally substituted heterocycyl or optionally substituted heteroaryl ring; wherein each instance of aliphatic, heteroaliphatic, carbocycyl, heterocycyl, aryl and heteroaryl is independently unsubstituted or substituted with 1, 2, 3, 4, 5, 6, 7, 8, 9, 10, or more substituents, as defined herein. In certain embodiments, each instance of aliphatic, heteroaliphatic, carbocycyl, heterocycyl, aryl and heteroaryl is independently unsubstituted or substituted with C$_{1-6}$alkyl, C$_{1-6}$fluoroalkyl or halogen.

In certain embodiments, each instance of R$^c$ is independently —F, aliphatic, heteroaliphatic, carbocycyl, heterocycyl, aryl, or heteroaryl, wherein each instance of aliphatic, heteroaliphatic, carbocycyl, heterocycyl, aryl and heteroaryl is independently unsubstituted or substituted with C$_{1-6}$alkyl, C$_{1-6}$fluoroalkyl or halogen.

In certain embodiments, each instance of R$^c$ is independently —F or alkyl, wherein each instance of alkyl is independently unsubstituted or substituted with C$_{1-6}$alkyl, C$_{1-6}$fluoroalkyl or halogen.

In certain embodiments, n is 0 or 1. In certain embodiments, n is 0. In certain embodiments, n is 1. In certain embodiments, n is 2.

As generally defined above, each instance of R$^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^f$, —SR$^f$, —NHR$^f$, or —N(R$^f$)$_2$, wherein each instance of R$^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^f$ groups are joined to form a 5- to 6-membered optionally substituted heterocycyl or optionally substituted heteroaryl ring; and m is 0, 1, 2, 3, or 4.

In certain embodiments, each instance of R$^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^f$, —SR$^f$, —NHR$^f$, or —N(R$^f$)$_2$, wherein each instance of R$^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^f$ groups are joined to form a 5- to 6-membered optionally substituted heterocycyl or optionally substituted heteroaryl ring; wherein each instance of aliphatic, heteroaliphatic, carbocycyl, heterocycyl, aryl and heteroaryl is independently unsubstituted or substituted with 1, 2, 3, 4, 5, 6, 7, 8, 9, 10, or more substituents, as defined herein. In certain embodiments, each instance of aliphatic, heteroaliphatic, carbocycyl, heterocycyl, aryl and heteroaryl is independently unsubstituted or substituted with $C_{1-6}$alkyl, $C_{1-6}$fluoroalkyl or halogen.

In certain embodiments, each instance of $R^d$ is independently —F, aliphatic, heteroaliphatic, carbocycyl, heterocycyl, aryl, or heteroaryl, wherein each instance of aliphatic, heteroaliphatic, carbocycyl, heterocycyl, aryl, and heteroaryl is independently unsubstituted or substituted with $C_{1-6}$alkyl, $C_{1-6}$fluoroalkyl or halogen.

In certain embodiments, each instance of $R^d$ is independently —F or alkyl, wherein each instance of alkyl is independently unsubstituted or substituted with $C_{1-6}$alkyl, $C_{1-6}$fluoroalkyl, or halogen.

In certain embodiments, m is 0 or 1. In certain embodiments, m is 0. In certain embodiments, m is 1. In certain embodiments, m is 2.

In certain embodiments, $R^z$ is an ortho, meta, or para substituent to the —OCH$_2$— linking group. In certain embodiments, $R^z$ is a meta substituent.

As generally defined above, $R^z$ is hydrogen, —F, —Br, —I, —Cl, optionally substituted aliphatic, heteroaliphatic, optionally substituted carbocycyl, optionally substituted heterocycyl, optionally substituted aryl, optionally substituted heteroaryl, —OR$^g$, —SR$^g$, —NHR$^g$, or —N(R$^g$)$_2$, wherein each instance of R$^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two R$^g$ groups are joined to form a 5- to 6-membered optionally substituted heterocycyl or optionally substituted heteroaryl ring.

In certain embodiments, $R^z$ is hydrogen, —F, —Br, —I, —Cl, optionally substituted aliphatic, heteroaliphatic, optionally substituted carbocycyl, optionally substituted heterocycyl, optionally substituted aryl, optionally substituted heteroaryl, —OR$^g$, —SR$^g$, —NHR$^g$, or —N(R$^g$)$_2$, wherein each instance of R$^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two R$^g$ groups are joined to form a 5- to 6-membered optionally substituted heterocycyl or optionally substituted heteroaryl ring, wherein each instance of aliphatic, heteroaliphatic, carbocycyl, heterocycyl, aryl and heteroaryl is independently unsubstituted or substituted with 1, 2, 3, 4, 5, 6, 7, 8, 9, 10, or more substituents, as defined herein. In certain embodiments, each instance of aliphatic, heteroaliphatic, carbocycyl, heterocycyl, aryl and heteroaryl is independently unsubstituted or substituted with $C_{1-6}$alkyl, $C_{1-6}$fluoroalkyl or halogen.

In certain embodiments, $R^z$ is hydrogen, alkyl, alkenyl, alkynyl, carbocycyl, heterocycyl, aryl, heteroaryl, —OR$^g$, —SR$^g$, —NHR$^g$, or —N(R$^g$)$_2$, wherein each instance of R$^g$ is independently hydrogen, alkyl, alkenyl, alkynyl, carbocycyl, heterocycyl, aryl, heteroaryl, or two R$^g$ groups are joined to form a 5- to 6-membered heterocycyl or heteroaryl ring, and wherein each instance of alkyl, alkenyl, alkynyl, carbocycyl, heterocycyl, aryl, and heteroaryl, is independently unsubstituted or substituted with $C_{1-6}$alkyl, $C_{1-6}$fluoroalkyl or halogen.

In certain embodiments, $R^z$ is hydrogen or aryl, wherein aryl is unsubstituted or substituted with $C_{1-6}$alkyl, $C_{1-6}$fluoroalkyl or halogen.

As generally depicted above, x is 1, 2, 3, 4, 5, or 6. In certain embodiments, x is 1 or 2. In certain embodiments, x is 1. In certain embodiments, x is 2.

It will be understood by one skilled in the art that each repeat unit of formula (c), when x is greater than 1, can optionally differ from one another, arising from differences in the independent variables Y, $R^c$, $R^d$, n and m, as well as different substitution patterns on and between each repeating unit. Thus, in further defining the compounds of the present invention, it is also generally helpful to further designate Y, $R^c$, $R^d$, n and m, with a sequential number corresponding to the first, second, third, fourth, fifth or sixth sequential group from which it is formally a member, e.g., Y, $R^c$, $R^d$, n, m and x can also be referred to as $Y^1$, $R^{c1}$, $R^{d1}$, n1 and m1 for the first group in the sequence; $Y^2$, $R^{c2}$, $R^{d2}$, n2 and m2 for the second optional repeating unit in the sequence; $Y^3$, $R^{c3}$, $R^{d3}$, n3 and m3 for the third optional repeating unit in the sequence; $Y^4$, $R^{c4}$, $R^{d4}$, n4 and m4 for the fourth optional repeating unit in the sequence; $Y^5$, $R^{c5}$, $R^{d5}$, n5 and m5 for the fifth optional repeating unit in the sequence; and $Y^6$, $R^{c6}$, $R^{d6}$, n6 and m6 for the sixth optional repeating unit in the sequence.

For example, in certain embodiments, the group of Formula (c) is of the formula:

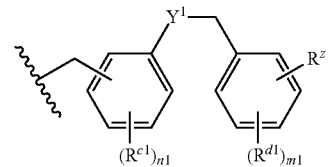

wherein x is 1;

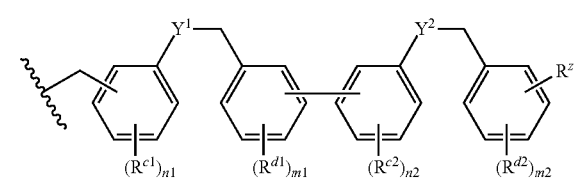

wherein x is 2;

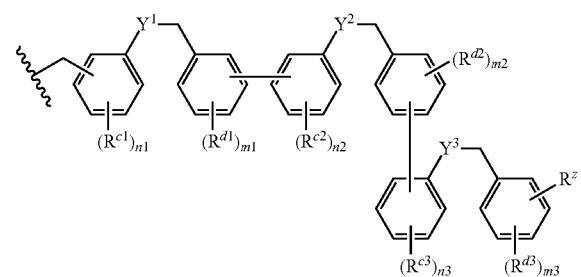

wherein x is 3;

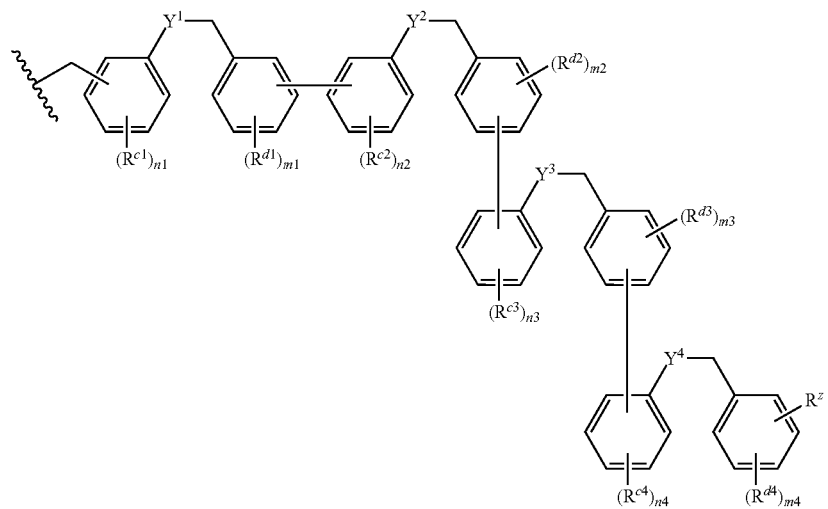
wherein x is 4;
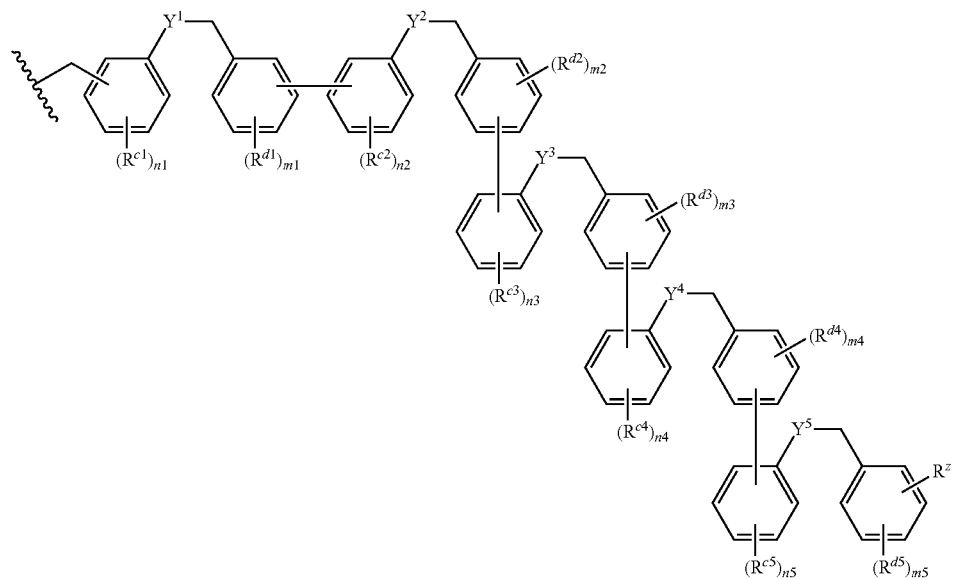
wherein x is 5;

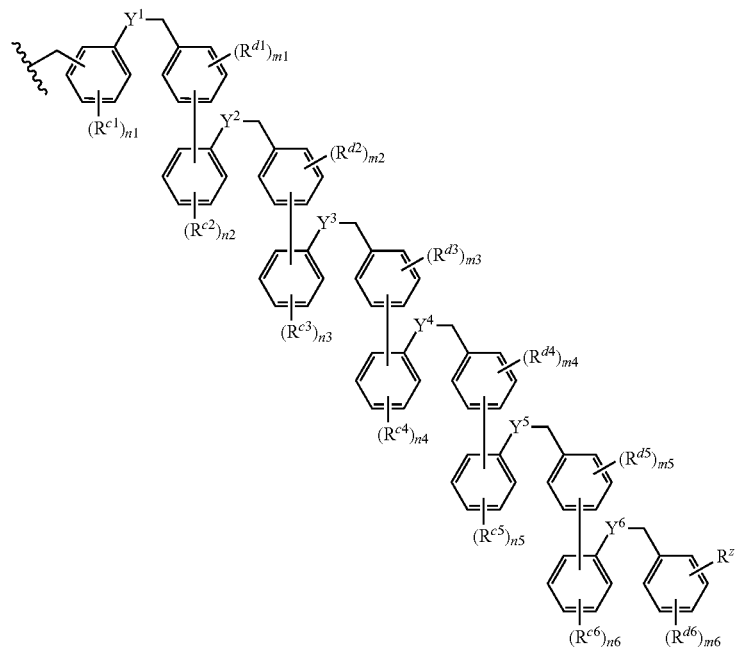

wherein x is 6;

wherein:

$R^{c1}$, $R^{c2}$, $R^{c3}$, $R^{c4}$, $R^{c5}$, and $R^{c6}$ each independently correspond to the definition and various embodiments of $R^c$;

$R^{d1}$, $R^{d2}$, $R^{d3}$, $R^{d4}$, $R^{d5}$, and $R^{d6}$ each independently correspond to the definition and various embodiments of $R^d$;

n1, n2, n3, n4, n5, and n6 each independently correspond to the definition and various embodiments of n;

m1, m2, m3, m4, m5, and m6 each independently correspond to the definition and various embodiments of m;

$Y^1$, $Y^2$, $Y^3$, $Y^4$, $Y^5$, and $Y^6$, each independently correspond to the definition and various embodiments of Y;

and $R^z$ is as defined herein.

In certain embodiments, the group of Formula (c) is of the formula:

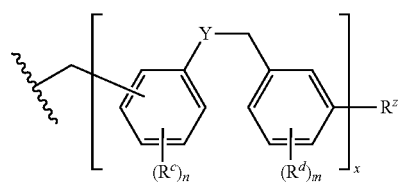

wherein Y, $R^z$, $R^c$, $R^d$, m, n, and x are as defined herein.

In certain embodiments, the group of Formula (c) is:

wherein x is 1;

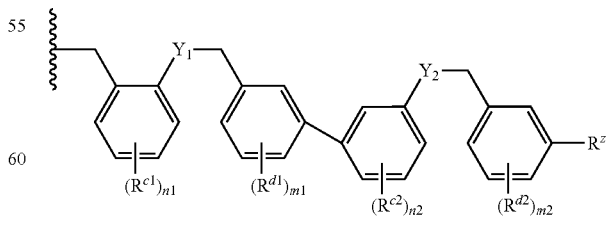

wherein x is 2;

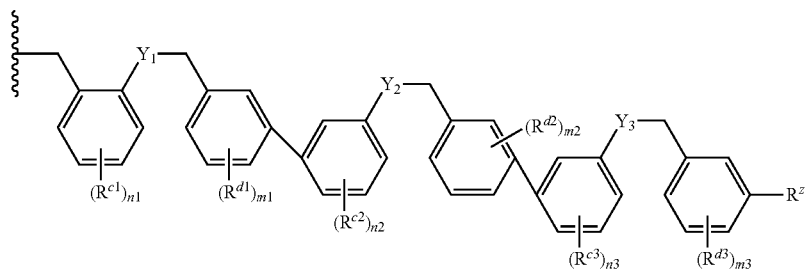
wherein x is 3;
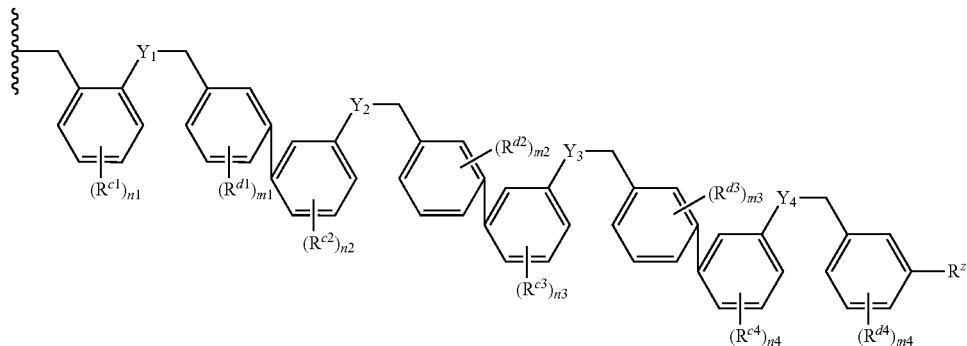
wherein x is 4;
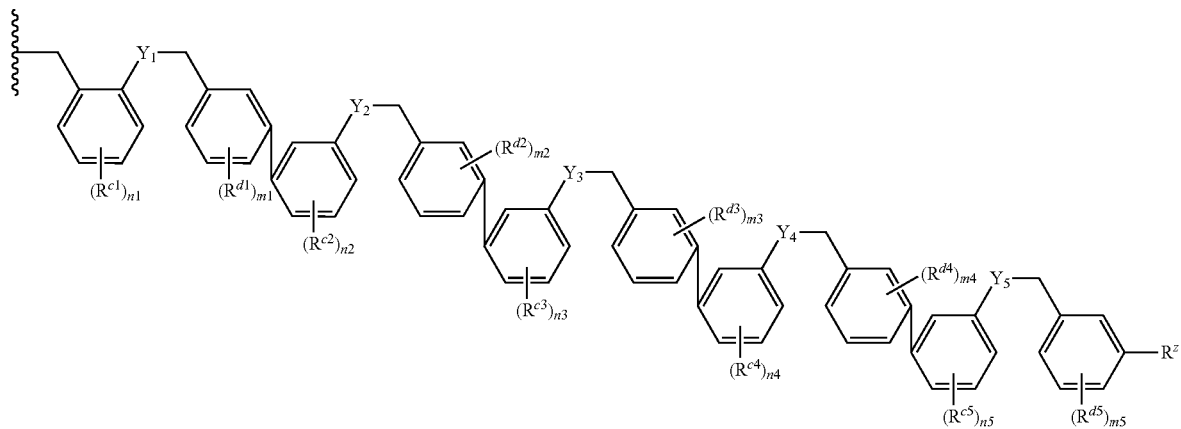
wherein x is 5;

or

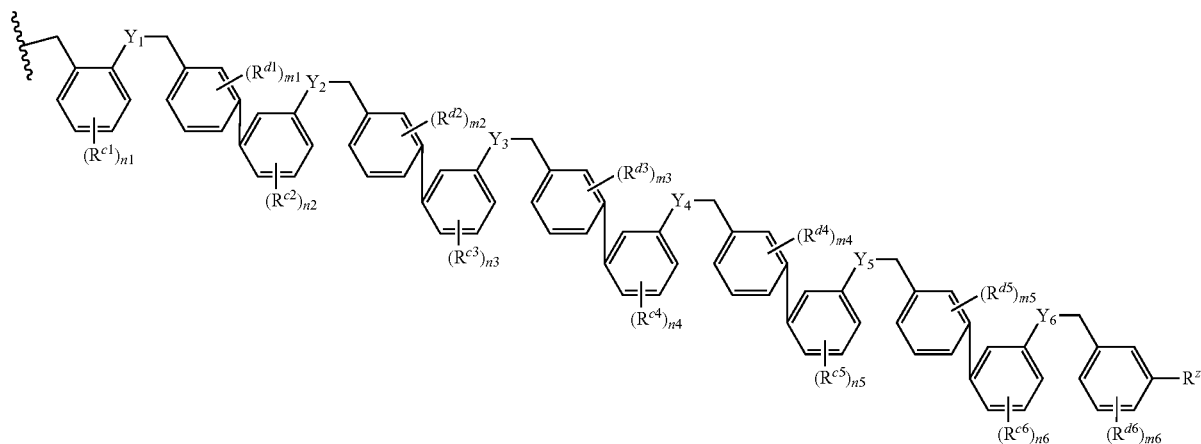

wherein x is 6;
wherein:
$R^{c1}$, $R^{c2}$, $R^{c3}$, $R^{c4}$, $R^{c5}$, and $R^{c6}$ each independently correspond to the definition and various embodiments of $R^c$;
$R^{d1}$, $R^{d2}$, $R^{d3}$, $R^{d4}$, $R^{d5}$, and $R^{d6}$ each independently correspond to the definition and various embodiments of $R^d$;
n1, n2, n3, n4, n5, and n6 each independently correspond to the definition and various embodiments of n;
m1, m2, m3, m4, m5, and m6 each independently correspond to the definition and various embodiments of m;
$Y^1$, $Y^2$, $Y^3$, $Y^4$, $Y^5$, and $Y^6$, each independently correspond to the definition and various embodiments of Y;
and $R^z$ is as defined herein.

In certain embodiments, each of n, n1, n2, n3, n4, n5, and n6 is 0.

In certain embodiments, each of m, m1, m2, m3, m4, m5, and m6 is 0.

In certain embodiments, each of Y, $Y^1$, $Y^2$, $Y^3$, $Y^4$, $Y^5$, and $Y^6$ is —O—.

In certain embodiments, $R^1$ is —C(O)NH$_2$; $R^2$ is hydrogen; $R^3$ is —OH; W is —O—; $R^4$ is hydrogen; $R^5$ is —C(O)CH$_3$; $R^6$ is —OH; $R^7$ is —OH; $R^a$ is hydrogen; and $R^b$ is hydrogen.

The reaction described above takes place in the presence of a galactosyltransferase (GalT) enzyme. In certain embodiments, the GalT is wild type. In certain embodiments, the GalT is a mutant. In certain embodiments, the GalT is GalT Y289L mutant.

Mammalian glycosyltransferases constitute a superfamily of enzymes that are involved in the synthesis of polysaccharides present in glycoproteins and glycolipids. β-1,4-Galactosyltransferase 1 (Gal-T1, EC 2.4.1.38) is a bovine enzyme present in milk that uses UDP-galactose (UDP-Gal), and Mn$^{2+}$ as cofactor, to transfer galactose to the 4-hydroxyl of N-acetylglucosamine (GlcNAc) to form a β-1,4-glycosidic bond (see Ramakrishnan et al. *J. Biol. Chem.* 2001, 276, 40, 37665 and references cited therein). This enzyme naturally shows some flexibility in the substrate requirements as it transfers glucose, 2-deoxy-glucose, arabinose, and GalNAc from the corresponding UDP-sugars, albeit in low efficiencies. Furthermore, interaction of Gal-T1 with α-lactalbumine alters the activity of the enzyme, and glucose can more efficiently be transferred to both glucose and N-acetylglucosamine. In 2002, Qasba and Ramakrishnan reported the structure based design of a mutant of Gal-T1 (i.e. Y289L) that showed both drastically enhanced activity as well as relaxed substrate requirements, with respect to the donor saccharide, while retaining β-1,4-selectivity for the acceptor sugar. This protein, a truncated version of the wild type Gal-T1, can be expressed in *E. coli* and reconstituted in vitro (Ramakrishnan et al. *J. Biol. Chem.* 2002, 277(23): 20833.). Since this seminal report, multiple applications of this enzyme have been reported in which N-acetyl galactosamine (GalNAc), its 2-carbadeoxy-analog, or N-azidoacetyl galactosamine (GalNAz) were transferred to acceptor substrates. These derivatizations allowed further downstream manipulations that facilitated identification of the acceptor substrate (see, for example, Khidekel et al. *J. Am. Chem. Soc.* 2003, 125: 16162; Tai et al. *J. Am. Chem. Soc.* 2004, 126: 10500; Hang et al. *Bioorg. Med. Chem.* 2005, 13: 5021; Hang et al. *Chem. & Biol.* 2004, 11: 337; Vocadlo et al. *Angew. Chem. Int. Ed.* 2004, 43: 5338; Vocadlo et al. *Proc. Natl. Acad. Sci. USA* 2003, 100: 9116).

In certain embodiments, the compound of Formula (III) is UDP galactose or a derivative thereof. In certain embodiments, the compound of Formula (III) is UDP-Gal. In certain embodiments, the compound of Formula (III) is UDP-GalNAc. In certain embodiments, the compound of Formula (III) is UDP-GalNAz.

In certain embodiments, the enzymatic reaction takes place in a buffer. In certain embodiments, the buffer is TRIS. In certain embodiments, the buffer is HEPES. In certain embodiments, additives are added to the reaction. In certain embodiments, the reaction takes place in the presence of an alkaline phosphatase. In certain embodiments, the reaction takes places in the presence of calf alkaline phosphatase. In certain embodiments, salts are added to the reaction. In certain embodiments, NaCl and/or MgCl$_2$ are added to the reaction. In certain embodiments, Mn$^{2+}$ is added to the reaction. In certain embodiments, MnCl$_2$ is added to the reaction.

In certain embodiments, the compound of Formula (I) is purified.

In certain embodiments, the compound of Formula (I) is further derivatized. For example, in certain embodiments when $R^{11}$ is —NHC(O)CH$_2$N$_3$, the azide group can be reduced to an amine which can then take part in other reactions, e.g., to form an amide, urea, or thiourea. In other embodiments, the azide group can take part in a cycloaddition, e.g. with an alkyne to form a 1,2,3-triazole. Other reactions include Staudinger ligation, oxime ligation or hydrazone ligation (Dirksen et al., *Biocong. Chem.* 19:2543-2548 (2008)), inverse electron demand Diels-Alder (e.g., tetrazine ligation (Blackman et al., *J. Am. Chem. Soc.* 130:13518-13519 (2008))), and [2+2+2]cycloaddition (e.g., quadricyclane ligation (Sletten et al., *J. Am. Chem. Soc.* 133:17570-17573 (2011))). Methods for such reactions are known in the art. Such further reactions allow for introduction of further diversity or e.g., introduction of a detectable moiety as described in U.S. Provisional Application entitled "Methods and Compounds for Identifying Glycosyltransferase Inhibitors," filed on the same day as the present application and incorporated herein by reference.

Additional sugars, such as D ring and/or B ring as described herein, can also be added to Formula (I). Methods for such glycosylation reactions have been described, for example, in PCT Application Publication Nos. WO 2008/021367 and WO 2009/046314, and U.S. Provisional Application entitled "Moenomycin A Analogs, Methods of Synthesis, and Uses Thereof," filed on the same day as the present application, each of which is incorporated herein by reference.

In certain embodiments, the G group of a compound of Formula (I) is removed and a different lipid tail is added. See, for example, PCT Application Publication No. WO 2009/046314, and U.S. Provisional Application entitled "Moenomycin A Analogs, Methods of Synthesis, and Uses Thereof," filed on the same day as the present application, each of which is incorporated herein by reference.

In certain embodiments, a method of present invention further comprises a deprotection step.

In some embodiments, the compound of Formula (II) is one of the following:

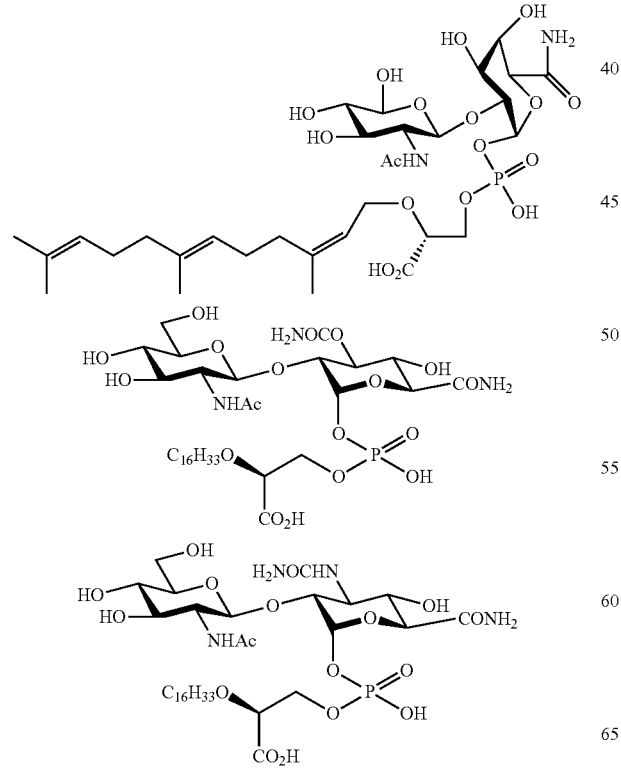

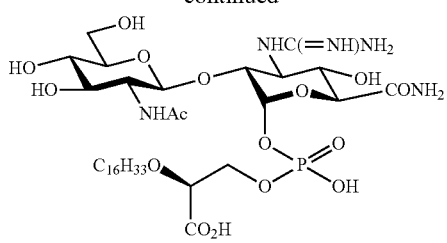

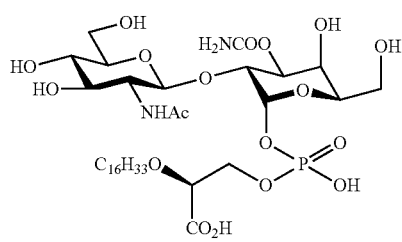

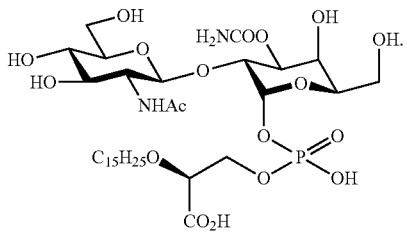

In certain embodiments, a compound of formula (I) is:

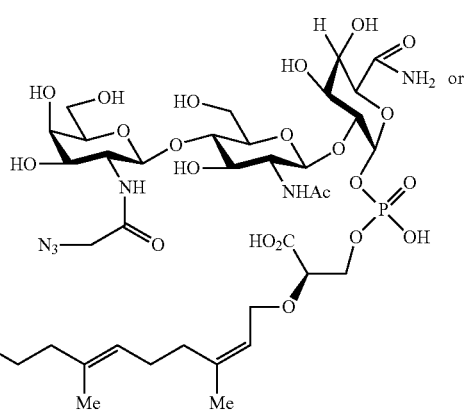

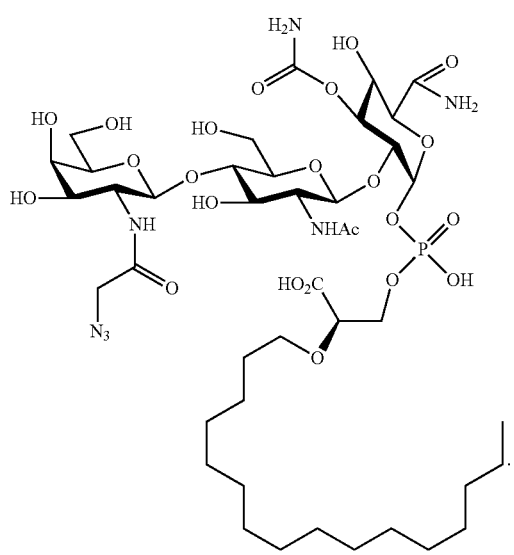

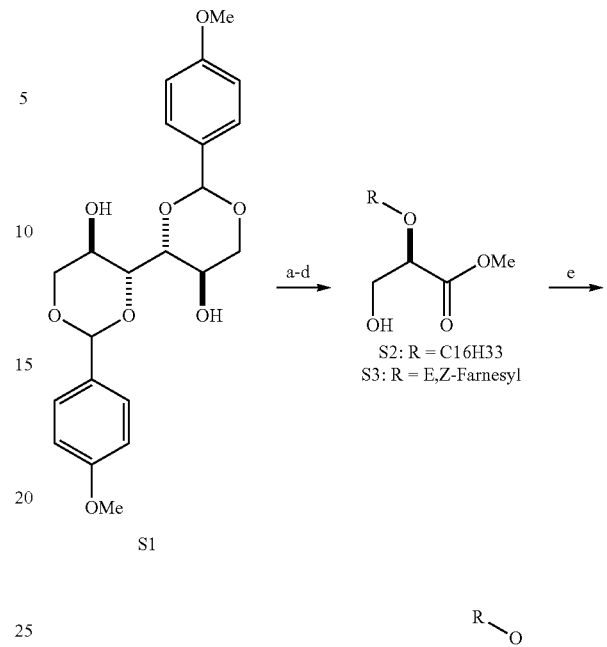

In certain embodiments, the present invention provides a kit comprising a compound of Formula (III) as described herein and a GalT enzyme. In some embodiments, a provided kit comprises a compound of Formula (III) as described herein and a GalT mutant, e.g., GalT Y289L. In certain embodiments, the compound of Formula (III) is UDP galactose or a derivative thereof. In certain embodiments, the compound of Formula (III) is UDP-Gal, UDP-GalNAc, or UDP-GalNAz. In some embodiments, the kit further comprises a buffer. In some embodiments, the kit further comprises an alkaline phosphatase. In certain embodiments, the kit further comprises a salt, e.g., NaCl and/or MgCl$_2$. In some embodiments, the kit further comprises instructions for use.

These and other aspects of the present invention will be further appreciated upon consideration of the following Examples, which are intended to illustrate certain particular embodiments of the invention but are not intended to limit its scope, as defined by the claims.

EXAMPLES

Chemical Syntheses

All reactions in non-aqueous reaction medium were carried out under an atmosphere of argon, unless otherwise noted. Commercial chemicals were used without prior purification. Solvents were dried by passage over columns filled with activated aluminum oxide (Glass Contour Solvent Systems, SG Water USA, Nashua, N.H., USA).

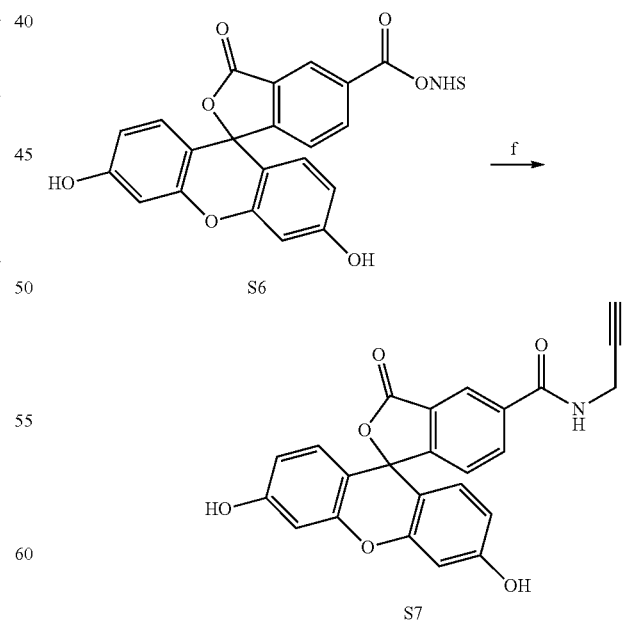

(a) R—Br, DMF, NaH then: AcOH; (b) NaIO$_4$, THF, H$_2$O; (c) NaClO$_2$, NaH$_2$PO$_4$, H$_2$O, 2-methyl-2-butene; (d) TMSCHN$_2$, MeOH, THF; (e) ClP(CEO)N$^i$Pr$_2$; (f) propargyl amine, NEt$_3$, DMF.

Synthesis of S2 and S3

General procedure for preparation of 2,5-Di-O-alkyl-D-Mannitol

To a stirred suspension of 60% NaH (3 equiv.), washed twice with petroleum ether, in anhydrous DMF (8 mL/mmol-starting material (SM)) was added 1,3:4,6-di-O,O-(4-methoxybenzylidene)-D-mannitol (1 equiv., SM) at room temperature. After being stirred for 30 min, the mixture was treated with a 1.2 M solution of alkylating reagents (2.4 equiv., Br, and methane- or p-toluene-sulfonate for R=allyl, and n-alkyl groups, respectively) in anhydrous DMF and a catalytic amount of tetrabutylammonium iodide for allyl-Br, or 15-Crown-5 for n-alkyl sulfonates. The resulting mixture was stirred for 18 h at rt for allyl-Br and 70° C. for n-alkyl sulfonates, and then poured into sat. aq. $NH_4Cl$ (8 mL/mmol-SM). The immiscible mixture was extracted twice with $Et_2O$ and the combined organic phases were washed with water, brine, dried over $MgSO_4$, and then concentrated in vacuo. The crude ether was used for the next reaction without further purification.

For allyl derivatives, a stirred solution of the residue in THF-$H_2O$ (4:1, 8 mL/mmol-SM) was treated with AcOH (170 equiv.) at room temperature. After being stirred at 55° C. for 2 d, the mixture was cooled to 0° C. and basified with 4 M aq. $K_2CO_3$ (90 equiv.). The immiscible mixture was extracted twice with $CHCl_3$ and the combined organic phases were washed with brine, dried over $MgSO_4$, and then concentrated in vacuo. The residue was purified by silica gel chromatography (petroleum ether:EtOAc=1:3 to 0:1) to give 2,5-di-O-allyl-D-mannitol.

For n-alkyl derivatives, a stirred solution of the residue in EtOH (12 mL/mmol-SM) was treated with 3 M aq. HCl (12 equiv.) at room temperature. After being stirred at 70° C. for 3 h, the mixture was cooled to room temperature and basified with 4 M aq. $K_2CO_3$ (16 equiv.). The immiscible mixture was extracted twice with $CHCl_3$ and the combined organic phases were washed with brine, dried over $MgSO_4$, and then concentrated in vacuo. The residue was purified by recrystallization from $Et_2O$/EtOAc to give 2,5-di-O-n-alkyl-D-mannitol.

Preparation of Methyl 2-O-Alkyl-D-Glycerate

To a 5.5 M solution of 2,5-di-O-alkyl-D-mannitol (1 equiv., SM) in THF-$H_2O$ (9:1) was added $NaIO_4$ (1.2 equiv.) at room temperature, and the mixture was stirred at 50° C. for 1 h. The resulting inorganic salt was removed by filtration through a pad of silica gel and washed with EtOAc. The filtrate was concentrated in vacuo and the crude aldehyde was used for the next reaction.

To a stirred solution of the residue in t-BuOH (20 mLUmmol-SM) were added 2-methyl-2-butene (100 equiv.) and a solution of 80% $NaClO_2$ (12 equiv.) and $NaH_2PO_4 \cdot H_2O$ (10 equiv.) in $H_2O$ (8 mL/mmol-SM) at 0° C. successively. The resulting yellow mixture was allowed to warm to room temperature for 6 h, during which it turned into clear. Then, the mixture was cooled to 0° C. again and treated with 2.5 M aq. $Na_2SO_3$ (25 equiv.) to reduce an excess of $NaClO_2$. The mixture was acidified with 10% aq. citric acid (10 mL/mmol-SM) and extracted twice with $CHCl_3$ and the combined organic phases were washed with brine, dried over $MgSO_4$, and then concentrated in vacuo. The crude acid was used for the next reaction without further purification.

To a stirred solution of the residue in anhydrous THF-MeOH (1:1, 10 mL/mmol-SM) was treated with 2 M TMSCHN$_2$ solution in hexanes (3.2 equiv.) at 0° C. After being stirred for 10 min, the resulting yellow mixture was decolorized by an addition of AcOH (3.2 equiv.) to consume an excess of TMSCHN$_2$. The mixture was concentrated in vacuo and the residue was purified by silica gel chromatography (petroleum ether:EtOAc=4:1 to 3:2) to give methyl 2-O-alkyl-D-glycerate.

Analytical data for S2: $^1$H-NMR (500 MHz; CDCl$_3$): δ 3.99 (dd, J=6.1, 3.8 Hz, 1H), 3.99 (dd, J=6.1, 3.8 Hz, 1H), 3.79 (d, J=14.1 Hz, 4H), 3.73 (q, J=7.9 Hz, 1H), 3.43 (t, J=11.3 Hz, 1H), 1.65-1.62 (m, 2H), 1.35-1.26 (m, 28H), 0.89 (t, J=7.0 Hz, 3H); $^{13}$C NMR (125 MHz, CDCl$_3$): δ 171.6, 79.8, 71.7, 63.7, 52.3, 32.2, 29.9 (multiple peaks), 29.8, 29.7, 29.6, 26.2, 22.9, 14.4; HRMS (ESI) calcd for $C_{20}H_{40}O_4Na^+$ [M+Na]$^+$ 367.2819. found 367.2823.

Analytical data for S3: $^1$H NMR (500 MHz; CDCl$_3$): δ 5.66 (dd, J=6.0, 2.1 Hz, 1H), 5.12-5.07 (m, 2H), 4.26-4.22 (m, 1H), 4.10 (d, J=6.5 Hz, 1H), 4.05 (m, 1H), 3.96 (m, 1H), 3.86 (m, 1H), 3.77 (s, 3H), 2.08-1.77 (m, 8H), 1.77 (s, 3H), 1.68 (s, 3H), 1.60 (s, 6H); $^{13}$C NMR (125 MHz, CDCl$_3$): δ 171.6, 142.5, 136.0, 131.6, 124.5, 123.7, 120.8, 67.2, 63.7, 52.3, 39.9, 32.7, 29.8, 29.7, 26.9, 25.7, 24.1, 23.6, 16.2; HRMS (ESI) calcd for $C_{19}H_{32}O_4Na^+$ [M+Na]$^+$ 347.2193. found 347.2206.

Preparation of 0.2 M Phosphoramidite Solution (S4 and S5)

To a 0.2 M solution of methyl 2-O-alkyl-D-glycerate (1 equiv.) in anhydrous CH$_3$CN were added N,N-diisopropylethylamine (1.5 equiv.) and ClP(OCE)Ni—Pr$_2$ (1.2 equiv.) at room temperature successively. The reaction mixture was stirred for 1 h and directly used for the next coupling reaction.

Preparation of S7

To as solution of N-hydroxysuccinimide fluorescein (S6, 15 mg, 21 μmol) in DMF (300 μL) was added NEt$_3$ (20 μL) and propargyl amine (3.0 mg, 48 μmol). After stirring the solution for 24 h the solvent was removed in vacuo and the residue was purified by column chromatography (SiO$_2$, hexane/EtOAc 2/8) to obtain S7 (11 mg, 27 μmol, 84%) as bright orange solid.

$^1$H NMR (500 MHz, CD$_3$OD) δ 8.43 (s, 1H), 8.20 (d, J=9.50 Hz, 1H), 7.31 (d, J=8.0 Hz, 1H), 6.69 (s, 1H), 6.61 (d, J=8.5 Hz, 2H), 6.54 (d, J=9.0 Hz, 2H), 4.59 (s, 1H), 4.21 (d, J=2.0 Hz, 1H), 2.65 (d, J=2.5 Hz, 1H); $^{13}$C NMR (500 MHz, CD$_3$OD) δ 169.4, 166.8, 152.9, 136.2, 134.4, 129.1, 129.0, 124.7, 123.9, 112.6, 112.2, 109.7, 102.5, 79.3, 78.1, 77.8, 71.2, 29.1.

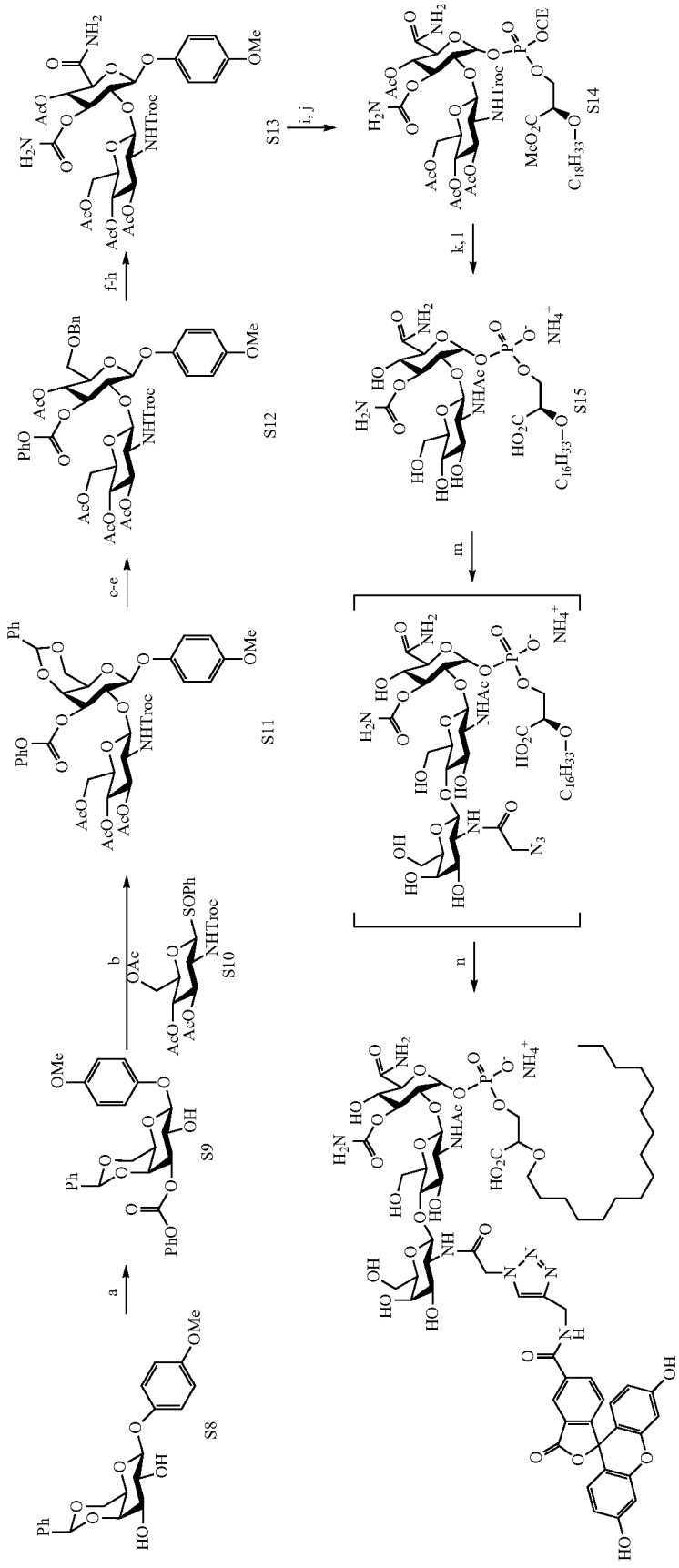
(a) ClCO$_2$Ph, Py; (b) Tf$_2$O, DTBMP, ADMB, MS-4A, DCM; (c) Et$_3$SiH, TfOH, MS-4A, DCM; (d) Tf$_2$O, Py., DCM; (e) CsOAc, 18-Crown-6, PhMe; (f) H$_2$, 10% Pd—C, MeOH; (g) TEMPO, PhI(OAc)$_2$, DCM—H$_2$O (2:1); (h) ClCO$_2$iBu, NMM, THF then NH$_3$, i-PrOH; (i) CAN, ACN—H$_2$O (4:1); (j) S2, tetrazole, MS-4A, ACN, then t-BuO$_2$H; (k) Zn, Ac$_2$O, AcOH, THF; (l) LiOH, THF—H$_2$O$_2$ (8:1); (m) UDP-GalNAz, β1,4-GalT; (n) DMF, H$_2$O, CuSO$_4$, Na-ascorbate.

Synthesis of S9

Saccharide S8 (18.7 g, 49.9 mmol, CAS: 176299-96-0) was dissolved in pyridine (160 mL) and cooled to −40° C. Phenylchlorocarbonate (11 mL) was added dropwise to the stirred solution. After 2 h, methanol (11 mL) and toluene (100 mL) were added and the solvent was removed in vacuum. The residue was taken up in EtOAc and washed with HCl (1 M) and NaCl (sat.). The organic layer was dried over $MgSO_4$ and the solvent was removed in vacuum. Recrystallization from $Et_2O$ yielded the title compound as colorless solid (18.5 g, 75%).

$^1$H NMR (500 MHz; $CDCl_3$): δ 7.54 (d, J=7.6 Hz, 2H), 7.37-3.35 (d, J=1.9 Hz, 5H), 7.22-7.21 (m, 3H), 7.07 (d, J=9.1 Hz, 2H), 6.83 (d, J=9.1 Hz, 2H), 5.55 (s, 1H), 4.91 (dd, J=10.2 Hz, 3.7 Hz, 1H), 4.85 (d, J=7.8 Hz, 1H), 4.53 (d, J=3.3 Hz, 1H), 4.34-4.31 (m, 2H), 4.05 (d, J=11.5 Hz, 1H), 3.76 (s, 3H), 3.51 (s, 1H), 2.89 (d, J=2.8 Hz, 1H); $^3$C NMR (125 MHz, $CDCl_3$): δ 155.9, 153.6, 151.3, 137.8, 129.7, 129.4, 128.4, 126.6, 126.4, 122.0, 121.3, 119.5, 114.8, 102.8, 101.1, 73.2, 69.1, 68.6, 66.5, 55.9; HRMS (ESI) calcd for $C_{27}H_{26}O_9Na^+$ [M+Na]$^+$ 517.1469. found 517.1506.

Synthesis of S10

Sulfoxide S10 was obtained by oxidation of peracyl-N-Troc-phenyl-(S,O)-glucosamine (CAS: 187022-49-7; 9.00 g, 15.1 mmol) with Selectfluor (6.00 g, 16.8 mmol) in MeCN (105 mL) and water (10.5 mL) at room temperature. The reaction was carried out in an open flask. After 1 h the solvent was removed in vacuum, and the residue was taken up in chloroform, washed with NaCl (sat.) and dried over $Na_2SO_4$. After concentration in vacuo the residue was recrystallized from EtOAc/hexane to yield sulfoxide S10 as an off-white solid (9.10 g, 15.5 mmol, 98%; 1/1 mixture of diastereomers).

Synthesis of S11

In a 100 mL round bottom flask, gylcosyl donor S10 (1.50 g, 2.55 mmol), gylcosyl acceptor S9 (840 mg, 1.70 mmol), 2,6-di-tert-butylpyridine (478 mg, 2.50 mmol), and 4-allyl-1,2-dimethoxybenzene (2.73 g, 15.3 mmol) were combined and dried by azeotropic distillation with benzene. The residue was further dried in vacuum for 30 min before dichloromethane (17 mL) and molecular sieves 4 A (ca. 500 mg) were added. The suspension was stirred at room temperature for 30 min and then cooled to −78° C. Triflic anhydride (285 μL, 479 mg, 1.70 mmol) was slowly added and the resulting green solution was stirred for 1.5 h at −78° C. $NaHCO_3$ (sat., 1 volume) was added, and the mixture was allowed to reach room temperature.

The phases were separated, and the organic phase was washed with NaCl (sat.) and dried over $Na_2SO_4$. Removal of the solvent in vacuum was followed by column chromatography ($SiO_2$, toluene/EtOAc 8/2→7/3) to yield the title compound as colorless solid (910 mg, 0.951 mmol, 56%).

$^1$H NMR (500 MHz; $CDCl_3$): δ 7.54 (d, J=7.6 Hz, 2H), 7.39-3.37 (d, J=1.9 Hz, 5H), 7.29-7.26 (m, 3H), 7.02 (d, J=9.1 Hz, 2H), 6.80 (d, J=9.1 Hz, 2H), 5.57 (s, 1H), 5.20-5.00 (m, 4H), 5.85-5.78 (m, 3H), 4.59 (br s, 1H), 4.40-4.22 (m, 3H), 4.21-4.19 (m, 1H), 4.16-4.12 (m, 1H), 3.86-3.75 (m, 2H), 3.77 (s, 3H), 3.59 (br s, 1H), 2.01 (s, 3H), 2.01 (s, 3H), 2.00 (s, 3H); $^{13}$C NMR (125 MHz, $CDCl_3$): δ 170.99, 170.88, 169.6, 155.63, 154.34, 152.75, 151.5, 151.2, 137.6, 128.9, 129.5, 128.5, 126.6, 121.3, 121.2, 118.8, 118.7, 114.7, 101.9, 101.3, 100.9, 76.2, 74.6, 72.9, 72.4, 72.0, 69.1, 68.4, 66.1, 61.8, 55.9, 20.91, 20.86; HRMS (ESI) calcd for $C_{42}H_{44}Cl_3NO_{18}Na^+$ [M+Na]$^+$ 978.1516. found 978.1472.

Synthesis of S12

Disaccharide S11 (1.06 g, 1.11 mmol) was dissolved in dichloromethane (22.2 mL) and $HSiEt_3$ (530 μL, 387 mg, 3.33 mmol) and molecular sieves 4 Å (ca. 500 mg) were added. The suspension was stirred for 30 min at room temperature and then cooled to −78° C. before triflic acid (333 μL, 566 mg, 3.77 mmol) was added dropwise. After 2.5 h at −78° C., $NaHCO_3$ (sat.) was added and the mixture was allowed to reach room temperature. The phases were parted and the aqueous layer was extracted once with dichloromethane. The combined organic layers were washed with brine and dried over $Na_2SO_4$. Removal of the solvent in vacuum provided the corresponding C6-benzyl ether of S11 in high purity, which was used in the next step without further purification.

The C6-benzyl ether previously obtained (1.15 g, 1.20 mmol) was dissolved in dichloromethane (12 mL) and pyridine (290 μL, 284 mg, 3.59 mmol), and the solution was cooled to −40° C. Triflic anhydride (242 μL, 406 mg, 1.44 mmol) was slowly added and the mixture was allowed to reach room temperature over 2 h. The reaction mixture was washed with 2 volumes of 0.5 M HCl, water, $NaHCO_3$ (sat.), and NaCl (sat), and then dried over $Na_2SO_4$. The solvent was removed in vacuum and the residue was dissolved in toluene (30 mL), and CsOAc (830 mg, 5.48 mmol) and 18-crown-6 (1.21 g, 4.58 mmol) were added. The resulting mixture was vigorously stirred for 14 h and then washed with $NaHCO_3$ (sat.) and NaCl (sat.). The residue obtained after drying of the solution over $Na_2SO_4$ and removal of the solvent in vacuum was purified by column chromatography ($SiO_2$, toluene/EtOAc 85/15) to obtain S12 as colorless solid (668 mg, 667 μmol, 55% over 3 steps).

$^1$H NMR (500 MHz; $CDCl_3$): δ 7.41-7.38 (m, 2H), 7.27 (s, 8H), 7.00 (d, J=9.0 Hz, 2H), 6.80 (d, J=8.50 Hz, 2H), 5.31 (t, J=9.6, 1H), 5.20-5.18 (m, 2H), 5.14-5.05 (m, 4H), 5.01 (d, J=8.1 Hz, 1H), 4.68 (d, J=12.0 Hz, 1H), 4.56 (d, J=11.8, 1H), 4.47 (d, J=11.9, 1H), 4.27 (d, J=12.2 Hz, 1H), 4.18 (dd, J=11.9, 3.4 Hz, 1H), 4.07 (td, J=8.2, 1.4 Hz, 1H), 3.77 (s, 3H), 3.67-3.60 (m, 3H), 3.59-3.57 (m, 1H), 2.01 (s, 3H), 2.01 (s, 3H), 2.00 (s, 3H), 1.95 (s, 3H); $^{13}$C NMR (125 MHz, $CDCl_3$): δ 170.93, 170.86, 170.11, 169.7, 155.69, 154.21, 153.32, 151.23, 151.12, 138.10, 137.91, 129.84, 129.27, 128.61, 128.46, 128.03, 127.98, 126.55, 125.52, 121.27, 118.12, 114.82, 114.79, 101.14, 100.44, 95.67, 79.60, 78.88, 74.53, 73.81, 73.22, 72.13, 72.00, 69.56, 68.81, 68.46, 61.72, 56.72, 55.91, 21.70, 20.91, 20.85, 20.81; HRMS (ESI) calcd for $C_{44}H_{48}Cl_3NO_{19}Na^+$ [M+Na]$^+$ 1022.1779. found 1022.1766.

Synthesis of S13

In a 100 ml round bottom flask, disaccharide S12 (283 mg, 283 μmol) was dissolved in methanol (20 mL), and 10% Pd/C (100 mg) was added. The atmosphere above the solution was exchanged to $H_2$, and the solution was stirred vigorously. After 45 min the suspension was filtered through Celite and the filtrate was concentrated in vacuo. The residue was dissolved in dichloromethane (3.4 mL) and water (1.7 mL), and $PhI(OAc)_2$ (237 mg, 756 μmol) and TEMPO (9.0 mg, 57 μmol) were added. After stirring the mixture for 2 h, the reaction was quenched by addition of $Na_2S_2O_3$ (sat.) and the solution was partitioned between dichloromethane and water. The organic layer was washed with NaCl (sat.) and dried over $Na_2SO_4$. The solvent was removed in vacuo, and the residue was taken up in THF (5.7 mL). This solution was cooled to −40° C., N-methylmorpholine (78 μL, 72 mg, 0.71 mmol) was added and the mixture was treated with isobutyl chloroformate (93 μL, 97 mg, 0.71 mmol). After 5 min, $NH_3$ (2.0 M in $^i$PrOH) was added and the mixture was stirred at room temperature for 24 h. Removal of the solvent in vacuum and column chromatography ($SiO_2$, $CHCl_3$/EtOH 99/1→95/5→9/1) yielded the title compound as colorless flakes (111 mg, 131 μmol, 46% over 3 steps).

$^1$H NMR (500 MHz; $CDCl_3$/$CD_3OD$ 9/1): δ 6.92 (d, J=8.9 Hz, 2H), 6.76 (d, J=9.0 Hz, 2H), 5.22 (t, J=9.9 Hz, 1H), 5.16-5.12 (m, 2H), 4.98 (dd, J=10.0 Hz, 2H), 4.90 (d, J=8.4 Hz, 1H), 4.87 (d, J=12.1 Hz, 1H), 4.49 (d, J=12.1 Hz, 1H), 4.09 (dd, J=12.3, 3.7 Hz, 1H), 3.99 (d, J=8.9 Hz, 1H), 3.88 (t, J=7.1 Hz, 1H), 3.78 (d, J=11.6 Hz, 1H), 3.71 (s, 3H), 3.62 (d, J=9.9 Hz, 1H), 3.55-3.48 (m, 5H), 2.00 (s, 3H), 1.94 (s, 3H), 1.93 (s, 3H), 1.92 (s, 3H); $^{13}$C NMR (125 MHz, $CDCl_3$/$CD_3OD$ 9/1): δ 171.20, 170.92, 170.6, 170.3, 170.0, 156.4, 155.8, 154.8, 150.7, 118.3, 114.9, 101.1, 100.1, 95.8, 79.4, 74.5, 73.9, 72.4, 71.8, 69.6, 68.7, 61.9, 56.5, 55.8, 49.7, 49.5, 49.4, 49.2, 48.9, 48.7, 20.7, 20.7; HRMS (ESI) calcd for $C_{31}H_{38}Cl_3N_3O_{18}Na^+$ $[M+Na]^+$ 868.1109. found 868.1067.

Synthesis of S14

Disaccharide S13 (167 mg, 187 μmol) was dissolved in MeCN (8 mL) and water (2 mL), and cerium(IV) ammonium nitrate (542 mg, 989 μmol) was added. The mixture was stirred at room temperature for 1.5 h and then concentrated in vacuo. Purification of the residue by column chromatography ($SiO_2$, $CHCl_3$/EtOH 9/1→4/1) gave the lactol of S13 as colorless solid (115 mg, 79%). This lactol (42.9 mg, 57.9 μmol) was further dried by azeotropic distillation with toluene (2×), dissolved in tetrazole solution (0.34 M in MeCN, 1.0 mL), and stirred with molecular sieves 4 Å for 30 min at room temperature and 30 min at 0° C. A solution of S4 (0.2 M in MeCN, 0.58 mL) was added and the mixture was stirred at 0° C. for 2 h before $^t$BuOOH (5.5 M in decane, 127 μL, 699 μmol) was added. After 1 h at 0° C. $P(OMe)_3$ (82 μL, 86 mg, 695 μmol) was added and the suspension was filtered through a pad of Celite. Evaporation of the solvent in vacuo and column chromatographic purification (C18, gradient 30-100% MeCN/$H_2O$) of the residue gave phosphoglycerate S14 (32.5 mg, 27.1 μmol, 47%) as colorless solid as a 1/1 mixture of phosphate diastereomers.

Analytical data for one diastereomer: $^1$H NMR (500 MHz; $CD_3OD$): δ 6.03 (dd, J=6.3, 3.2 Hz, 1H), 5.27-5.20 (m, 3H), 5.07 (t, J=9.7 Hz, 1H), 5.02 (d, J=12.3 Hz, 1H), 4.78 (d, J=8.5 Hz, 1H), 4.61 (d, J=12.3 Hz, 1H), 4.46-4.42 (m, 4H), 4.45-4.41 (m, 4H), 4.22 (dd, J=12.3, 2.2 Hz, 1H), 4.00 (dd, J=6.9, 3.3 Hz, 1H), 3.87-3.83 (m, 2H), 3.82 (s, 3H), 3.72-3.65 (m, 2H), 3.59-3.55 (m, 1H), 3.01 (t, J=6.0 Hz, 2H), 2.10 (s, 3H), 2.04 (s, 3H), 2.01 (s, 3H), 1.96 (s, 3H), 1.66 (t, J=7.2 Hz, 2H), 1.30 (m, 28H), 0.91 (t, J=7.0 Hz, 3H); HSQC ($^{13}$C signals, 125 MHz, $CD_3OD$): δ 102.7, 97.2; 77.9, 77.6, 74.2, 74.1, 72.2, 72.0, 71.5, 71.4, 70.4, 70.3, 69.5, 68.8, 68.2, 68.1, 63.6, 61.9, 61.8, 55.6, 51.8, 48.1, 31.6, 29.6 (multiple peaks), 25.8, 22.5, 19.6, 19.3, 19.3, 19.3, 18.9, 13.2; $^{31}$P (162 MHz; $CD_3OD$): δ −3.16; HRMS (ESI) calcd for $C_{47}H_{74}Cl_3N_4O_{23}PNa^+$ $[M+Na]^+$ 1223.3410. found 1223.3337.

Synthesis of S15

To a solution of phosphoglycerate S14 (113 mg, 94.2 μmol) in THF (3 mL), $Ac_2O$ (1 mL), and AcOH (2 mL) was added activated Zn (653 mg, 9.99 mmol), and the solution was stirred at room temperature for 10 h. The slurry was filtered through a pad of $SiO_2$ and the residue was thoroughly washed with $CHCl_3$/EtOH 2/1 (100 mL). The filtrate was concentrated, and the residue was dissolved in THF (19 mL), $H_2O_2$ (30%, 4.8 mL) and aqueous LiOH solution (1 M, 1.9 mL). After stirring the solution at 0° C. for 2 h, DOWEX50WX2-100 resin (HPy+ form, 0.8 g) was added, and the mixture was stirred for 2 h. The resin was filtered off by passing the reaction mixture through a cotton plug. Chromatographic purification (C18, gradient 20-50% MeCN in 0.2% $NH_4HCO_3$ aq.) of the residue obtained after concentration of the filtrate yielded disaccharide S15 (50.7 mg, 61.0 μmol, 63%).

HPLC/MS retention time: 11.9 min (Phenomenex Luna, 3u-C18 50×2 $mm^2$ 3 micron, 0.3 ml/min, gradient 30-75% MeCN+0.1% $HCO_2H$ in $H_2O$+0.1% $HCO_2H$ over 6 min, then to 99% MeCN+0.1% $HCO_2H$ over 5 min) LRMS (ESI) calcd for $C_{34}H_{61}N_3O_{18}P^-$ $[M-H]^-$ 830.4. found 830.3; $^1$H NMR (500 MHz; $CD_3OD$): δ 5.98 (dd, J=7.1, 3.1 Hz, 1H), 5.05 (t, J=9.7 Hz, 1H), 4.58 (d, J=8.4 Hz, 1H), 4.36 (d, J=10.0 Hz, 1H), 4.26-4.22 (m, 1H), 4.18-4.08 (m, 1H), 4.00-3.96 (m, 1H), 3.87-3.84 (m, 1H), 3.76-3.71 (m, 3H), 3.71 (s, 3H), 3.68-3.64 (m, 3H), 3.53-3.47 (m, 3H), 3.36-3.29 (m, 4H), 2.04 (s, 3H), 1.66-1.64 (m, 2H), 1.30 (m, 28H), 0.91 (t, J=7.0 Hz, 3H); $^{13}$C NMR (125 MHz, $CD_3OD$): δ; 175.6, 173.0, 158.2, 103.0, 95.5, 79.6, 76.9, 74.5, 73.2, 71.4, 70.8, 70.6, 70.5, 70.2, 66.9, 66.8, 61.6, 61.1, 59.9, 56.1, 31.9, 29.6, 29.6, 29.5, 29.3, 26.0, 22.6, 22.2, 13.3; $^{31}$P (162 MHz; $D_6$-DMSO): δ −2.31; HRMS (ESI) calcd for $C_{34}H_{63}N_3O_{18}P^+[M+H]^+$ 832.3839. found 832.7735.

Synthesis of S16 (CMG121)

To a solution of TRIS (50 mM in $H_2O$, pH=8.0, 2.5 mL) were sequentially added $MnCl_2$ (50 mM in $H_2O$, 2.5 mL), $H_2O$ (5 mL), GalT Y289L (Ramakrishanan et al. *J. Biol Chem.* 2002, 277, 20833; 1 mg/mL in 50 mM TRIS buffer, pH=8.0, 1.88 mL,), UDP-N-azidoacetylgalactosamine (UDP-GalNAz, prepared according to Hang et al. *J. Am. Chem. Soc.* 2003, 126, 6; 20 mM in $H_2O$, 500 μL), disaccharide S15 (10 mM in $H_2O$, 125 μL), and calf intestinal alkaline phosphatase (CIP, 1000 U, 25 L, Roche Diagnostics GmbH, Mannheim, Germany). The mixture was gently mixed and kept at 37° C. for 60 h. MeOH (7.5 mL) was added, and the mixture was vortexed and centrifuged (15 min at 5000×g) to pellet precipitated proteins. The supernatant was concentrated in vacuo, and the residue obtained was loaded onto a Phenomenex Strata C-18 column pre-equilibrated with $H_2O$. The column was eluted with $H_2O$ to obtain unreacted UDP-GalNAz. Elusion with $H_2O$/MeOH 1/9 provided the desired trisaccharide in near quantitative yield.

HPLC retention time: 11.0 min (Phenomenex Luna, 3u-C18 50×2 $mm^2$ 3 micron, 0.3 mL/min, gradient 30-75% MeCN+0.1% $HCO_2H$ in $H_2O$+0.1% $HCO_2H$ over 6 min, then to 99% MeCN+0.1% $HCO_2H$ over 5 min) LRMS (ESI) calcd for $C_{42}H_{73}N_7O_{23}P^-$ $[M-H]^-$ 1074.5. found 1074.3.

The GalNAz-trisaccharide previously obtained (4.0 mg, 3.8 μmol) was dissolved in DMF (400 μL) and $CuSO_4$ (0.9 M in $H_2O$, 4.0 μL, 3.6 μmol) and Na-ascorbate (1.8 M in $H_2O$, 4.0 μL, 7.2 μmol) were added. The mixture was stirred at room temperature, and after 24 h another portion of $CuSO_4$ (0.9 M in $H_2O$, 4.0 μL, 3.6 μmol) and Na-ascorbate (1.8 M in $H_2O$, 4.0 μL, 7.2 μmol) was added. After 48 h the solution was concentrated in vacuo and the residue was purified by column chromatography (C-18, gradient 30-90% MeOH in H$_2$O; then 10% 2 M NH$_3$ in MeOH to elute the product) to obtain the title compound (4.9 mg, 3.3 μmol, 87%).

HPLC/MS retention time: 10.8 min (Phenomenex Luna, 3u-C18 50×2 mm$^2$ 3 micron, 0.3 mL/min, gradient 30-75% MeCN+0.1% HCO$_2$H in H$_2$O+0.1% HCO$_2$H over 6 min, then to 99% MeCN+0.1% HCO$_2$H over 5 min); LRMS (ESI) calcd for C$_{66}$H$_{88}$N$_8$O$_{29}$P$^-$ [M–H]$^-$ 1487.5. found 1487.3; $^1$H NMR (600 MHz; CD$_3$OD): δ 8.51 (s, 1H), 8.28-8.27 (m, 1H), 8.11 (s, 1H), 7.35 (d, J=7.5 Hz, 1H), 6.72 (m, 2H), 6.65 (d, J=8.5 Hz, 2H), 6.60-6.59 (m, 2H), 6.01 (br s, 1H), 5.29 (br s, 1H), 5.05 (t, J=6.8 Hz, 1H), 4.77 (m, 2H), 4.61-4.56 (m, 2H), 4.38 (d, J=7.5 Hz, 1H), 4.29-4.25 (m, 2H), 4.15-4.05 (m, 2H), 4.05-3.99 (m, 2H), 3.86-3.76 (m, 4H), 3.76-3.60 (m, 13H), 3.48 (br s, 1H), 2.02 (s, 3H), 1.65-1.64 (m, 6H), 1.48-1.42 (m, 12H), 1.31 (m, 38H), 0.92 (t, J=5.4 Hz, 3H); HSQC ($^{13}$C signals, 125 MHz, CD$_3$OD): δ 129.1, 124.1, 112.9, 102.4, 102.3, 79.5, 75.8, 75.0, 73.3, 73.0, 71.5, 71.2, 70.5, 70.0, 68.3, 67.0, 61.2, 53.4, 52.0, 35.1, 31.8, 29.5, 26.0, 23.5, 22.6, 21.9, 13.1; HRMS (ESI) calcd for C$_{66}$H$_{90}$N$_8$O$_{29}$P$^+$ [M+H]$^+$ 1489.5546. found 1489.5420.

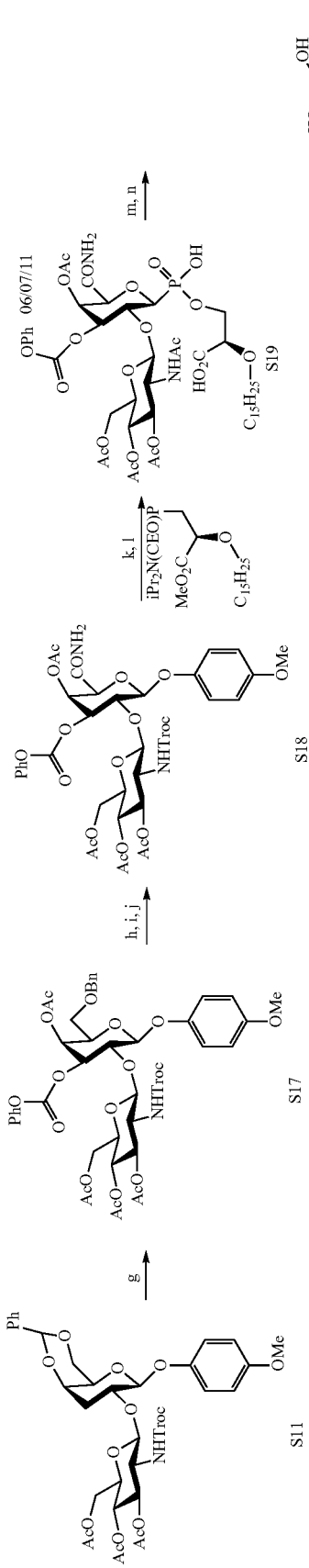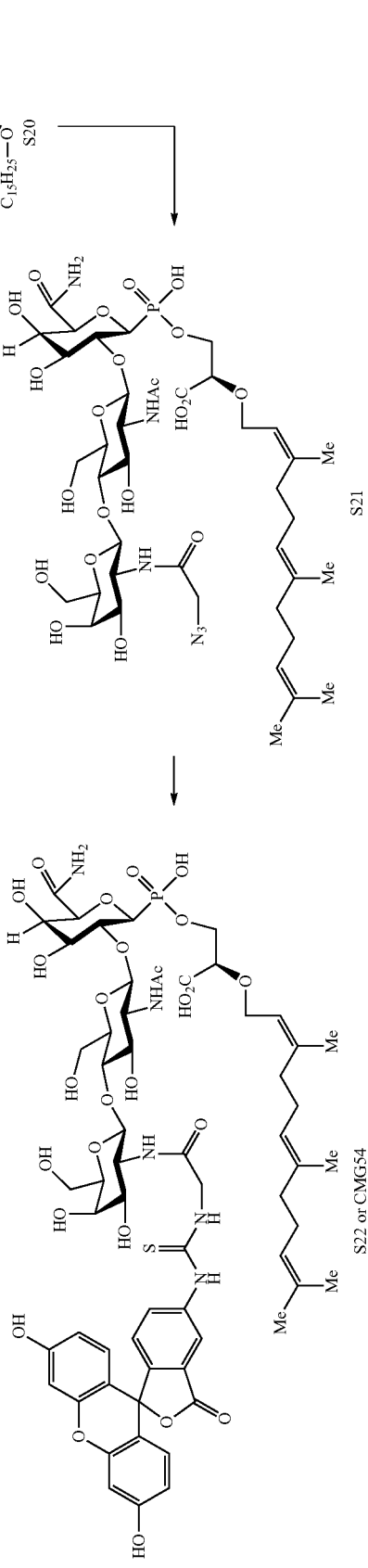
(g) Et$_3$SiH, triflic acid, then: Ac$_2$O, Py,, cat. DMAP, DCM; (h) H$_2$, 10% Pd—C, 1 wt % Cl$_3$CCO$_2$H/MeOH; (i) TEMPO, PhI(OAc)$_2$, DCM—H$_2$O (2:1); (j) ClCO$_2$iBu, NMM, THF then NH$_3$, i-PrOH; (k) CAN, ACN—H$_2$O (4:1); (l) S5, tetrazole, MS-3A, ACN, then t-BuOH$_2$H; (m) Zn, Ac$_2$O, AcOH, THF; (n) LiOH,THF—MeOH—H$_2$O (3:3:1); (o) UDP-GalNAz, β1,4-GalT; (p) Pd(OH)$_2$/C, MeOH, H$_2$; (q) fluoresceinisothiocyanate

Synthesis of S17

Disaccharide S11 (650 mg, 679 μmol) was dissolved in dichloromethane (13.6 mL) and HSiEt$_3$ (325 μL, 237 mg, 2.04 mmol) and molecular sieves 3 Å (ca. 250 mg) were added. The suspension was stirred for 30 min at room temperature and then cooled to −78° C. before triflic acid (204 μL, 347 mg, 2.31 mmol) was added dropwise. After 2.5 h at −78° C., NaHCO$_3$ (sat.) was added and the mixture was allowed to reach room temperature. The phases were parted and the aqueous layer was extracted once with dichloromethane. The combined organic layers were washed with brine and dried over Na$_2$SO$_4$. Removal of the solvent in vacuo provided the corresponding C6-benzyl ether of S11 in high purity, which was dissolved in dichloromethane (3.4 mL), and pyridine (164 μL, 161 mg, 2.04 mmol), DMAP (8.3 mg, 0.07 mmol), and Ac$_2$O (94 μL, 104 mg, 1.02 mmol) were added. After 3 h at room temperature the reaction was diluted with dichloromethane and washed with HCl (1 M), H$_2$O, NaHCO$_3$ (sat.), and NaCl (sat.). The organic layers were dried over Na$_2$SO$_4$ and then concentrated in vacuo. Purification of the residue yielded acetate S17 (539 mg, 538 μmol, 79% over 2 steps) as colorless solid.

$^1$H NMR (500 MHz; CDCl$_3$): δ 7.39 (t, J=7.8 Hz, 2H), 7.34-7.25 (m, 8H), 7.01 (d, J=9.0 Hz, 2H), 6.79 (d, J=9.0 Hz, 2H), 5.64 (d, J=2.5 Hz, 1H), 5.26 (t, J=10.1 Hz, 1H), 5.14-5.10 (m, 2H), 5.01 (d, J=7.2 Hz, 1H), 4.90-4.88 (m, 2H), 4.81 (d, J=12.2 Hz, 1H), 4.56 (d, J=12.0 Hz, 1H), 4.44 (d, J=12.0 Hz, 1H), 4.29 (d, J=12.2 Hz, 1H), 4.23 (dd, J=12.2, 3.3 Hz, 1H), 4.11 (dd, J=9.8, 7.7 Hz, 1H), 3.94 (t, J=6.4 Hz, 1H), 3.90-3.86 (m, 2H), 3.77 (s, 3H), 3.70-3.66 (m, 2H), 3.59-3.55 (m, 2H), 2.11 (s, 3H), 2.03 (s, 3H), 2.02 (s, 3H), 2.01 (s, 3H); $^{13}$C NMR (125 MHz, CDCl$_3$): δ 171.1, 170.9, 170.5, 169.6, 155.7, 154.2, 152.7, 151.5, 151.2, 138.1, 137.7, 129.8, 129.3, 128.7, 128.5, 128.2, 128.1, 126.6, 125.6, 121.5, 118.3, 114.8, 101.9, 100.8, 95.7, 74.5, 73.8, 72.1, 72.0, 68.4, 67.7, 67.2, 61.8, 56.9, 55.9, 21.0, 20.9, 20.8, 20.8; HRMS (ESI) calcd for C$_{44}$H$_{48}$Cl$_3$NO$_{19}$Na$^+$ [M+Na]$^+$ 1022.1779. found 1022.1707.

Synthesis of S18

In a 10 mL round bottom flask S17 (56.4 mg, 56.3 μmol) was dissolved in a solution of 1% trichloroacetic acid in methanol (2.8 mL, 2.4 equiv. of TCA), 10% Pd/C (11.9 mg) was added and the atmosphere above the solution was exchanged to H$_2$. After stirring for 15 min the solution was filtered through a pad of Celite and poured into NaHCO$_3$ (sat.). The mixture was extracted with EtOAc (2×), washed with NaCl (sat.), and dried over MgSO$_4$. Evaporation of the solvent in vacuum yielded the free C6-alcohol in quantitative yield.

The alcohol previously obtained (51.3 mg, 56.3 μmol) was dissolved in dichloromethane (0.2 mL) and water (0.1 mL). After addition of TEMPO (1.8 mg, 1.2 μmol) and diacetoxy iodobenzene (45.0 mg, 140 μmol) the mixture was stirred at room temperature for 1.5 h. Na$_2$S$_2$O$_3$ (sat.) solution was added, and the reaction mixture was extracted with EtOAc (2×). The combined organic layers were washed with NaCl (sat.) and dried over MgSO$_4$. The residue obtained after concentration of the solution in vacuum was purified by column chromatography (SiO$_2$, petroleum ether/EtOAc/1% AcOH 2/1→1/4) to obtain pure C6-carboxylic acid (36.8 mg, 39.8 μmol, 71% over 2 steps).

The C6-carboxylic acid (22.0 mg, 23.8 μmol) was dissolved in THF (0.6 mL) and N-methyl-morpholine (5.2 μL, 47 μmol), and the solution was cooled to −30° C. before isobutylchloroformate (6.2 μL, 47 μmol) was added. After 30 min the turbid mixture was treated with 7 M NH$_3$ solution in MeOH (14 μL) and stirred at 0° C. for another 30 min. The mixture was poured into NH$_4$Cl and extracted with EtOAc (2×). The organic layers were washed with NaCl (sat.) and dried over MgSO$_4$ before they were concentrated in vacuo. Column chromatographic purification of the residue (SiO$_2$, petroleum ether/EtOAc 2/1→1/4) gave S18 as colorless solid (21.8 mg, 23.6 μmol, 99%).

Synthesis of S19

Deprotection of the PMP group was achieved by treatment of a solution of S18 (21.8 mg, 23.8 μmol) in MeCN (1.2 mL) and water (0.3 mL) with cerium (IV) ammonium nitrate (40.2 mg, 73.3 μmol). After stirring at room temperature for 1 h the mixture was concentrated in vacuo, and the residue was purified by column chromatography (SiO$_2$, CHCl$_3$/MeOH 98/2→95/5) to give the free lactol as colorless solid (12.8 mg, 15.6 μmol, 66%). This material was dried by azeotropic distillation with toluene (2×), dissolved in a solution of tetrazole in MeCN (0.34 M, 0.28 mL), and molecular sieves 3 Å (43 mg) were added. The mixture was stirred at room temperature for 15 min and then cooled to 0° C. before a solution of S5 was added (0.2 M in MeCN, 0.15 mL). After 1 h at 0° C., $^t$BuOOH (5.5 M in decane, 23 L) was added, and the suspension was stirred for another hour before P(OMe)$_3$ (22 μL, 186 μmol) was added. The mixture was filtered over Celite, and the residue was concentrated in vacuo. Purification of the residue by column chromatography (SiO$_2$, CHCl$_3$/MeOH 97/3→96/4) gave S19 as colorless solid as a mixture of phosphate diastereomers (16.0 mg, 12.7 μmol, 81%).

Synthesis of S20

Phosphoglycerate S19 (7.6 mg, 6.0 μmol) was dissolved in a mixture of THF (0.3 mL), Ac$_2$O (0.1 mL), and AcOH (0.2 mL) and activated zinc (70.1 mg) was added in portions over the course of 1.5 d. The suspension was filtered through a pad of Celite, concentrated in vacuo, and subjected to column chromatography (SiO$_2$, CHCl$_3$/MeOH 96/4). The product obtained was dissolved in a mixture of THF (0.66 mL), MeOH (0.22 mL), and H$_2$O (0.22 mL) and LiOH (1 M in H$_2$O, 66 L, 66 μmol) was added. After stirring at room temperature for 1.5 h, AcOH (4 μL, 7 μmol) was added, and the solution was concentrated in vacuo. Purification of the residue by column chromatography (C18, gradient 25-75% MeOH in H$_2$O+0.1% AcOH) gave S20 (3.3 mg, 4.3 μmol, 71% over 2 steps) as colorless solid.

Synthesis of S21

To a solution (2 mL) containing HEPES (50 mM, pH=7.5), NaCl (100 mM), MnCl$_2$ (1 mM), S20 (1 mM), UDP-N-azidoacetylgalactosamine (UDP-GalNAz, prepared according to Hang et al. *J. Am. Chem. Soc.* 2003, 126, 6; 2 mM) were added calf intestinal alkaline phosphatase (1000 U, 5 μL, Roche Diagnostics GmbH, Mannheim, Germany) and GalT Y289L (Ramakrishanan et al. *J. Biol Chem.* 2002, 277, 20833, 150 μg), and the mixture was incubated at 37° C. for 2 h. The reaction was quenched by precipitation of the proteins by addition of MeOH (4 mL), was centrifuged, and the supernatant was passed over a 30 mg Strata-X C18 column (Phenomenex). The column was eluted with water (2 mL) to rinse off salts, UMP, and UDP-GalNAz, and the desired trisaccharide S21 was eluted with MeOH/H₂O 8/2. The material obtained was directly used in the next reaction.

Synthesis of S22

Azide S21 (3.8 mg, 3.8 μmol) was dissolved in a mixture of MeOH (210 μL), water (10 μL), and HOAc (2 M, 2 μL) and Pd(OH)₂/C (1 mg) was added. The atmosphere above the solution was exchanged for H₂, and the mixture was stirred vigorously for 48 h. The mixture was filtered over a plug of Celite, the residue was thoroughly washed with MeOH/H₂O 4/1, and the filtrate was concentrated in vacuo. The residue obtained was suspended in DMF (76 μL) and treated with diisopropylethylamine (5.3 μL) and fluorescein isothiocyanate (1.7 mg, 4.6 μmol). After 16 h at room temperature, the solution was concentrated in vacuum, and the residue was purified by column chromatography (SiO₂, CHCl₃/MeOH+0.1% AcOH 9/1→8/2; then CHCl₃/MeOH/H₂O 60/40/8) to obtain the title compound (2.0 mg, 1.5 μmol, 40% over 2 steps) as orange solid.

HPLC/MS retention time: 11.6 min (Phenomenex Luna, 3u-C18 50×2 mm² 3 micron, 0.3 mL/min, gradient 25-45% MeCN+0.1% HCO₂H in H₂O+0.1% HCO₂H over 6 min, then to 99% MeCN+0.1% HCO₂H over 6.5 min); LRMS (ESI) calcd for $C_{61}H_{77}N_5O_{27}PS^-$ [M–H]⁻ 1374.4. found 1374.3; HRMS (ESI) calcd for $C_{61}H_{79}N_5O_{27}PS^+$ [M+H]⁺ 1376.4416. found 1376.4224.

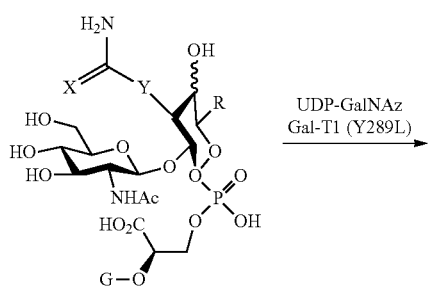

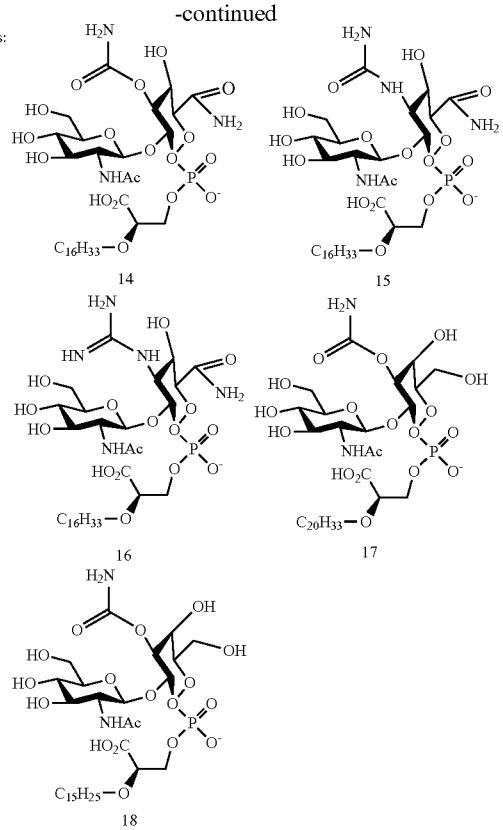

Substrates: 14, 15, 16, 17, 18

All small scale (20 uL) reactions of GalT(Y289L) were run in 50 mM HEPES pH=7.5, 100 mM NaCl, 1 mM MnCl₂ with 0.2 μL calf alkaline phosphatase, 40 μM disaccharide, and 100 μM UDP-GalNAz. The reaction was initiated by the addition of 1.5 μg of GalT(Y289L), incubated at 37° C. for 2 h, and quenched with 2 volumes of MeOH. After centrifuging at 10 k rpm for 2 minutes, the reaction was analyzed by LC-MS QTOF.

For scale up of the GalT(Y289L) reactions, 2 mL reactions were set up in 50 mM HEPES pH=7.5, 100 mM NaCl, 1 mM MnCl₂ with 5 μL of calf alkaline phosphatase, 1 mM disaccharide, and 2 mM UDP-GalNAz. These reactions were initiated by the addition of 0.15 mg of GalT(Y289L), incubated at 37° C. for 2 h, and stored at −20° C. until purification. The resultant trisaccharide was purified by revered phase chromatography. Each 2 mL reaction was centrifuged and loaded onto a 30 mg Strata-X C18 column (Phenomenex). The protein pellet was washed with 2 mL water, which was then also run on the column. The column was further washed with another 2 ml of water, then, the trisaccharide was eluted in 80% methanol. Reactions were analyzed by LC-MS QTOF:

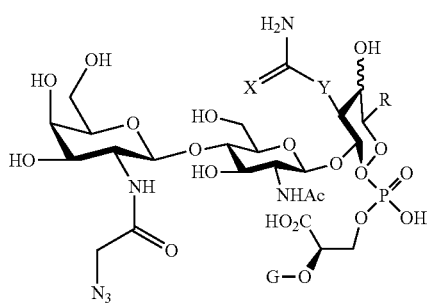

| Compound | substrate (M − H)− | | | product (M − H)− | | | % conversion |
|---|---|---|---|---|---|---|---|
| | expected | observed | Δppm | expected | observed | Δppm | |
| 14 | 830.3693 | 830.3670 | −2.79 | 1074.4500 | 1074.4457 | −3.07 | 85% |
| 15 | 829.3853 | 829.3844 | −1.09 | 1073.4660 | 1073.4648 | −1.12 | 67% |
| 16 | 828.4012 | 828.4005 | −0.85 | 1072.4820 | 1072.4825 | 0.47 | 52% |
| 17 | 865.3740 | 865.3707 | −3.81 | 1109.4548 | 1109.4515 | −3.05 | 88% |
| 18 | 797.3115 | 797.3071 | −5.48 | 1041.3922 | 1041.3919 | −0.37 | 100% |

OTHER EMBODIMENTS

This application refers to various issued patents, published patent applications, journal articles, books, manuals, and other publications, all of which are incorporated herein by reference.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:
1. A method of synthesizing a compound of Formula (I):

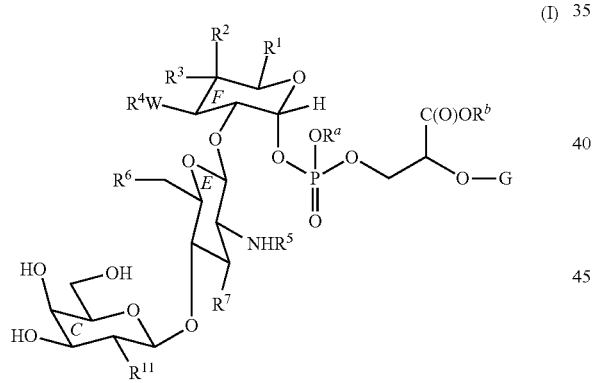

wherein
$R^1$ is —C(O)NHR$^8$, —CH$_2$OR$^9$, or —C(O)OR$^9$;
$R^2$ and $R^3$ are independently hydrogen, optionally substituted aliphatic, —OR$^9$, —N(R$^8$)$_2$, or —C(O)NHR$^8$;
W is —O— or —NH—;
$R^4$ is hydrogen, a hydroxyl protecting group, optionally substituted aliphatic, —C(O)R$^{10}$, —C(O)NHR$^8$, —C(=NR$^8$)NHR$^8$, or —C(O)OR$^9$;
$R^5$ is hydrogen, an amino protecting group, optionally substituted aliphatic, or —C(O)R$^{10}$;
$R^6$ is hydrogen, —OR$^9$, or —OR$^{CX}$; wherein R$^{CX}$ is a carbohydrate moiety;
$R^7$ is —OR$^9$ or —N(R$^8$)$_2$;
$R^8$ is hydrogen, an amino protecting group, —C(O)R$^{10}$, optionally substituted aliphatic, optionally substituted aryl, optionally substituted heterocyclyl, or optionally substituted heteroaryl;
$R^9$ is hydrogen, a hydroxyl protecting group, —C(O)R$^{10}$, optionally substituted aliphatic, optionally substituted aryl, optionally substituted heterocyclyl, or optionally substituted heteroaryl;
$R^{10}$ is optionally substituted aliphatic, optionally substituted heterocyclyl, optionally substituted aryl, or optionally substituted heteroaryl;
$R^{11}$ is —N(R$^8$)$_2$;
q is 0, 1, 2, 3, 4, 5, or 6;
$R^a$ and $R^b$ are independently hydrogen or a hydroxyl protecting group;
G is an optionally substituted C$_{1-30}$ aliphatic group, wherein 0 to 10 methylene units are optionally replaced with —O—, —NR$^x$—, —S—, —C(O)—, —C(=NR$^x$), —S(O)—, —SO$_2$—, —N=N—, —C=N—, —N—O—, an optionally substituted arylene, an optionally substituted heterocyclylene, or an optionally substituted heteroarylene; or
G is a group of Formula (a), (b), or (c):

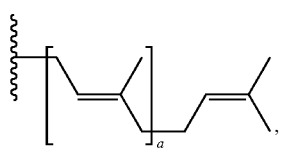

wherein a is 3, 4, or 5;

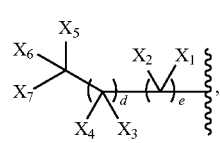

wherein
$X_1$, $X_2$, $X_3$, $X_4$, $X_5$, $X_6$, and $X_7$ are each independently hydrogen or halogen;
d is an integer between 1 and 25, inclusive; and
e is an integer of between 2 and 25, inclusive;
provided the sum of d and e is greater than 16; or

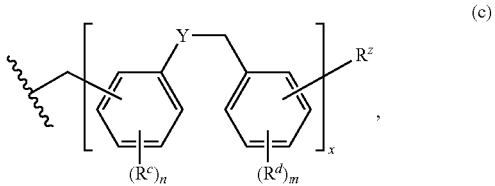

wherein
Y is —O—, —S—, —NR$^Y$—, or an optionally substituted methylene group, wherein R$^Y$ is hydrogen, optionally substituted aliphatic, or an amino protecting group;

each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, or —N(R$^e$)$_2$, wherein each instance of R$^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^e$ groups are joined to form a 5- to 6-membered optionally substituted heterocycyl or optionally substituted heteroaryl ring;

each instance of R$^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^f$, —SR$^f$, —NHR$^f$, or —N(R$^f$)$_2$, wherein each instance of R$^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^f$ groups are joined to form a 5- to 6-membered optionally substituted heterocycyl or optionally substituted heteroaryl ring;

R$^z$ is hydrogen, —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^g$, —SR$^g$, —NHR$^g$, or —N(R$^g$)$_2$, wherein each instance of R$^g$ is independently hydrogen, optionally substituted aliphatic, optionally substituted heteroaliphatic, optionally substituted carbocyclyl, optionally substituted heterocyclyl, optionally substituted aryl, or optionally substituted heteroaryl or two R$^g$ groups are joined to form a 5- to 6-membered optionally substituted heterocycyl or optionally substituted heteroaryl ring;

each instance of n is, independently, 0, 1, 2, 3, or 4;
each instance of m is, independently, 0, 1, 2, 3, or 4; and
x is 1, 2, 3, 4, 5, or 6;

comprising:
(i) providing a compound of Formula (II):

(II)

and
(ii) reacting the compound of Formula (II) in the presence of a galactosyltransferase enzyme (GalT) with a UDP-sugar of Formula (III):

(III)

to yield a compound of Formula (I).

2. The method of claim 1, wherein R$^{10}$ is optionally substituted aliphatic.

3. The method of claim 2, wherein R$^{10}$ is methyl or —CH=CH$_2$.

4. The method of claim 2, wherein R$^{10}$ is substituted with halo —N$_3$, —CN, —NC, —NCO, —OCN, —NCS, —SCN, —NO, —N$_2$, an amino group, a hydroxyl group, aryl, heteroaryl, or optionally substituted heterocyclyl.

5. The method of claim 1, wherein R$^{10}$ is —CH$_2$aryl or —CH$_2$heteroaryl.

6. The method of claim 1, wherein R$^{11}$ is

7. The method of claim 1, wherein the compound of Formula (III) is UDP-GalNAz, UDP-galactosamine, or UDP-GalNAc.

8. The method of claim 1, wherein
R$^1$ is —C(O)NH$_2$;
R$^2$ is hydrogen;
R$^3$ is —OH;
W is —O—;
R$^4$ is hydrogen;
R$^5$ is —C(O)CH$_3$;
R$^6$ is —OH;
R$^7$ is —OH;
R$^a$ is hydrogen; and
R$^b$ is hydrogen.

9. The method of claim 1, wherein G is

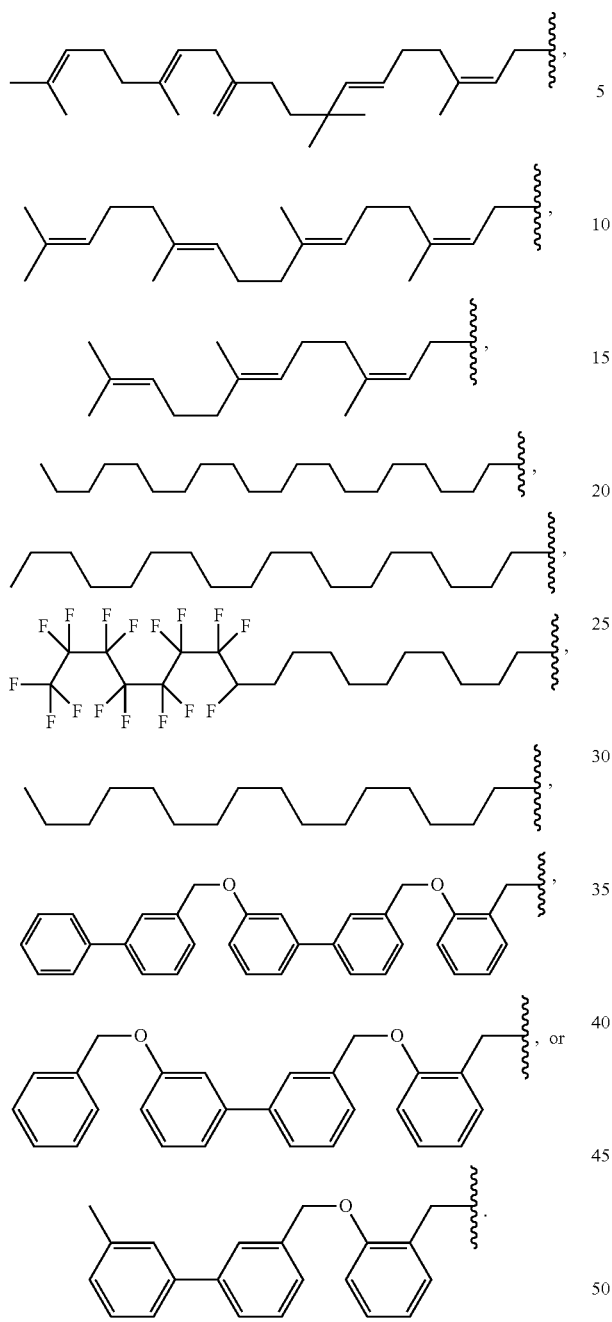

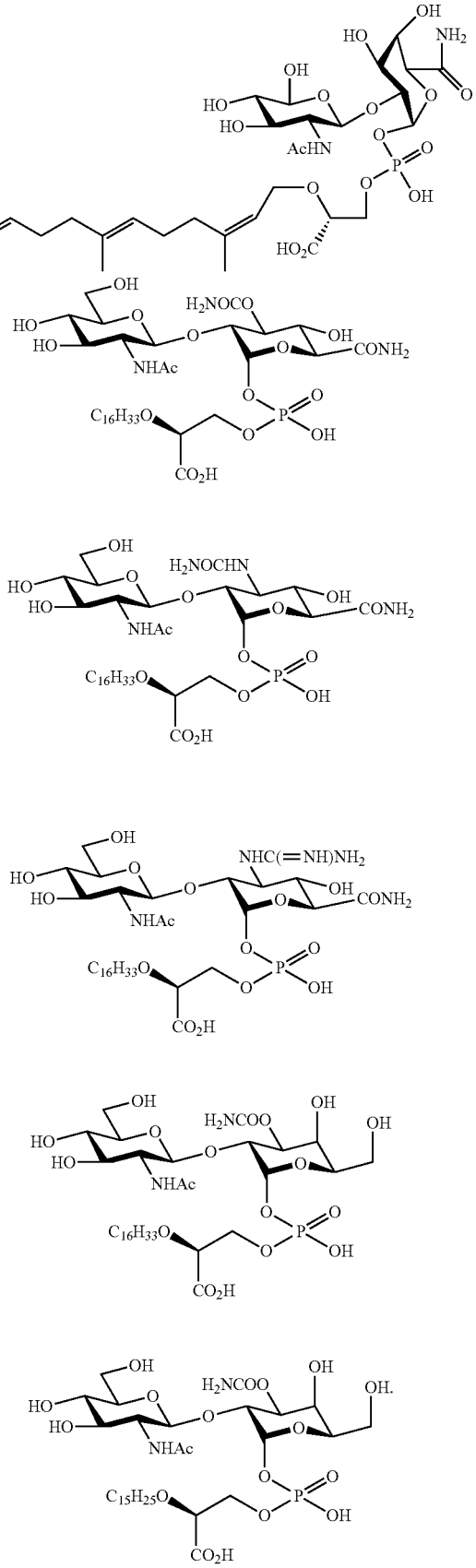

10. The method of claim 1, wherein $R^1$ is —C(O)NH$_2$ or —CH$_2$OH.

11. The method of claim 1, wherein $R^2$ is hydrogen; and $R^3$ is —OH; or $R^3$ is hydrogen; and $R^2$ is —OH.

12. The method of claim 1, wherein —W—$R^4$ is —OH, —NHC(O)NH$_2$, —OC(O)NH$_2$ or —NHC(=NH)NH$_2$.

13. The method of claim 1, wherein $R^5$ is —C(O)CH$_3$.

14. The method of claim 1, wherein $R^6$ is —OH or —OR$^{CX}$; wherein R$^{CX}$ is a carbohydrate moiety.

15. The method of claim 1, wherein $R^7$ is —OH.

16. The method of claim 1, wherein the compound of Formula (II) is one of the following:

17. The method of claim 1, wherein the compound of Formula (I) is one of the following:
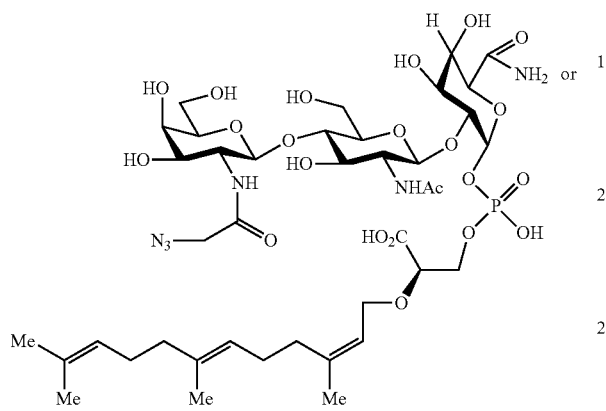 or 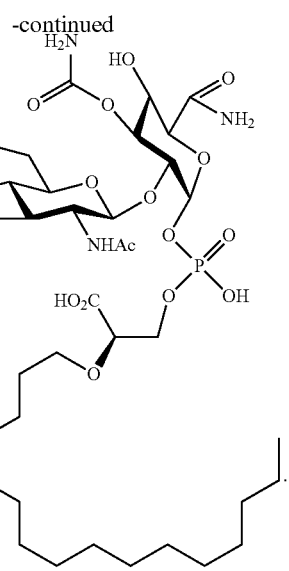
18. The method of claim 1, wherein $R^{11}$ is —NHC(O)$R^{10}$.
19. The method of claim 18, wherein $R^{10}$ is optionally substituted aliphatic.
20. The method of claim 19, wherein $R^{10}$ is substituted with —N$_3$.
21. The method of claim 20, wherein $R^{10}$ —CH$_2$N$_3$.
* * * * *